United States Patent
Tajima

(10) Patent No.: US 10,842,457 B2
(45) Date of Patent: Nov. 24, 2020

(54) RADIOGRAPHIC IMAGING SYSTEM, CONTROL METHOD FOR RADIOGRAPHIC IMAGING SYSTEM, AND NON-TRANSITORY COMPUTER READABLE MEDIUM STORING A CONTROL PROGRAM FOR RADIOGRAPHIC IMAGING SYSTEM

(71) Applicant: FUJIFILM Corporation, Tokyo (JP)

(72) Inventor: Takashi Tajima, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 16/665,787

(22) Filed: Oct. 28, 2019

(65) Prior Publication Data

US 2020/0054301 A1 Feb. 20, 2020

Related U.S. Application Data

(63) Continuation of application No. 15/673,681, filed on Aug. 10, 2017, now Pat. No. 10,492,750, which is a
(Continued)

(30) Foreign Application Priority Data

Feb. 24, 2015 (JP) .................................. 2015-034497

(51) Int. Cl.
G03G 13/05 (2006.01)
A61B 6/00 (2006.01)
A61B 6/12 (2006.01)

(52) U.S. Cl.
CPC .................. *A61B 6/52* (2013.01); *A61B 6/00* (2013.01); *A61B 6/12* (2013.01); *A61B 6/461* (2013.01);
(Continued)

(58) Field of Classification Search
CPC .. A61B 6/52; A61B 6/548; A61B 6/56; A61B 6/467; A61B 6/00; A61B 6/54; A61B 6/461; A61B 6/12
See application file for complete search history.

(56) References Cited

U.S. PATENT DOCUMENTS

| 2004/0088193 A1 | 5/2004 | Moriyama |
| 2004/0190780 A1 | 9/2004 | Shiibashi |

(Continued)

FOREIGN PATENT DOCUMENTS

| JP | 2004290316 A | 10/2004 |
| JP | 2004313757 A | 11/2004 |

(Continued)

OTHER PUBLICATIONS

International Search Report of PCT/JP2016/053321, dated May 17, 2016. [PCT/ISA/210].
(Continued)

*Primary Examiner* — Kiho Kim
(74) *Attorney, Agent, or Firm* — Sughrue Mion, PLLC

(57) ABSTRACT

A radiographic imaging system includes a portable information terminal 16 and a console 18 which are plural control devices of which each one performs a control relating to imaging of a radiographic image and of which at least one is selectively used; and a terminal control unit 30 of the portable information terminal 16 and a control unit 50 of the console 18 that respectively function as a setting unit that sets, with respect to at least one of usage control devices which is control device to be selectively used, control content based on one usage control device in a case where the number of usage control devices is one, and sets control content based on a combination of plural usage control devices in a case where the number of usage control devices is plural.

20 Claims, 55 Drawing Sheets

Related U.S. Application Data continuation of application No. PCT/JP2016/053321, filed on Feb. 4, 2016.

(52) U.S. Cl.
CPC ............... *A61B 6/467* (2013.01); *A61B 6/54* (2013.01); *A61B 6/548* (2013.01); *A61B 6/56* (2013.01)

(56) References Cited

U.S. PATENT DOCUMENTS

| | | |
|---|---|---|
| 2007/0273697 A1 | 11/2007 | Zaman |
| 2011/0077960 A1* | 3/2011 | Kiuchi ............... G06Q 10/10 705/2 |
| 2013/0321284 A1 | 12/2013 | Bello |
| 2013/0329860 A1 | 12/2013 | Nonaka |

FOREIGN PATENT DOCUMENTS

| | | |
|---|---|---|
| JP | 2007313310 A | 12/2007 |
| JP | 2013111402 A | 6/2013 |
| JP | 2013244409 A | 12/2013 |
| JP | 2014012120 A | 1/2014 |
| JP | 2014183963 A | 10/2014 |
| JP | 2014211764 A | 11/2014 |

OTHER PUBLICATIONS

Written Opinion from the International Searching Authority dated May 17, 2016, in counterpart International Application No. PCT/JP2016/053321.

International Preliminary Report on Patentability dated Aug. 29, 2017, in counterpart International Application No. PCT/JP2016/053321.

* cited by examiner

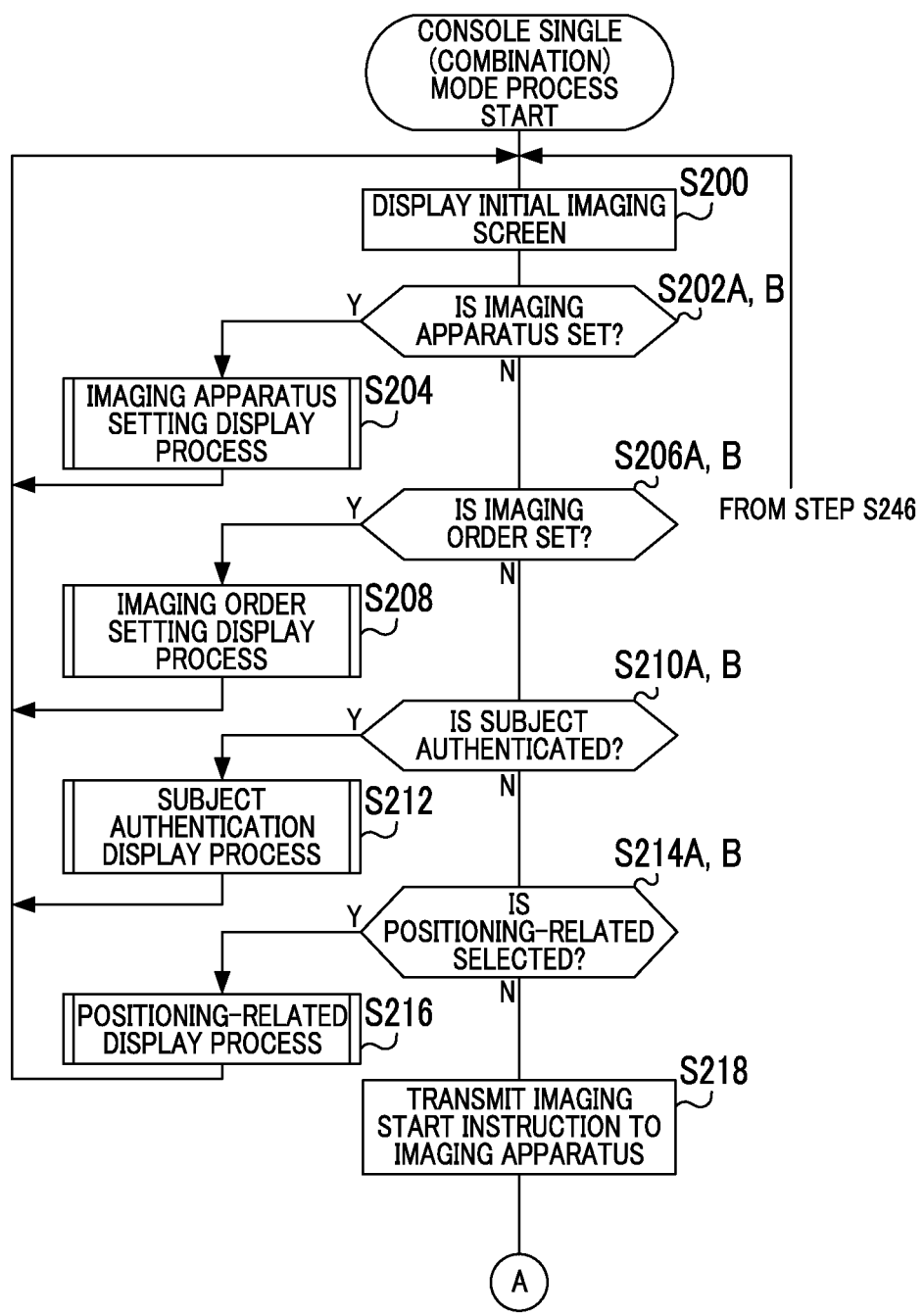

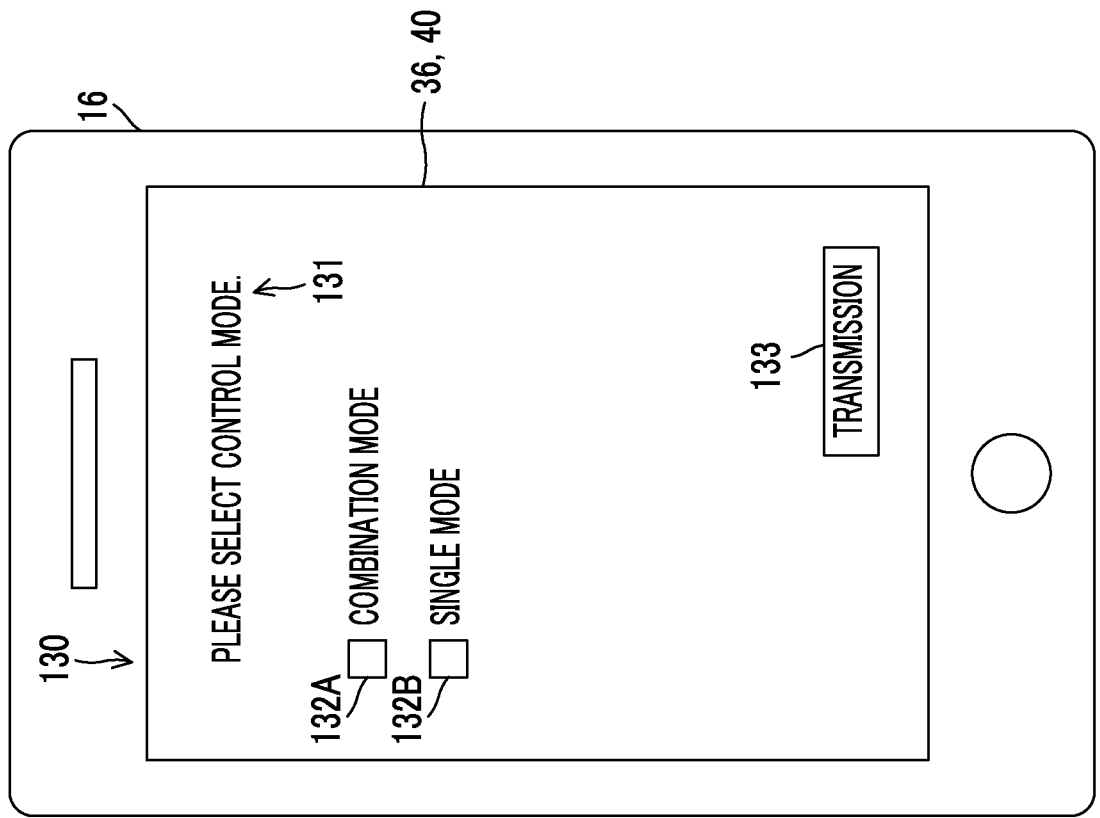

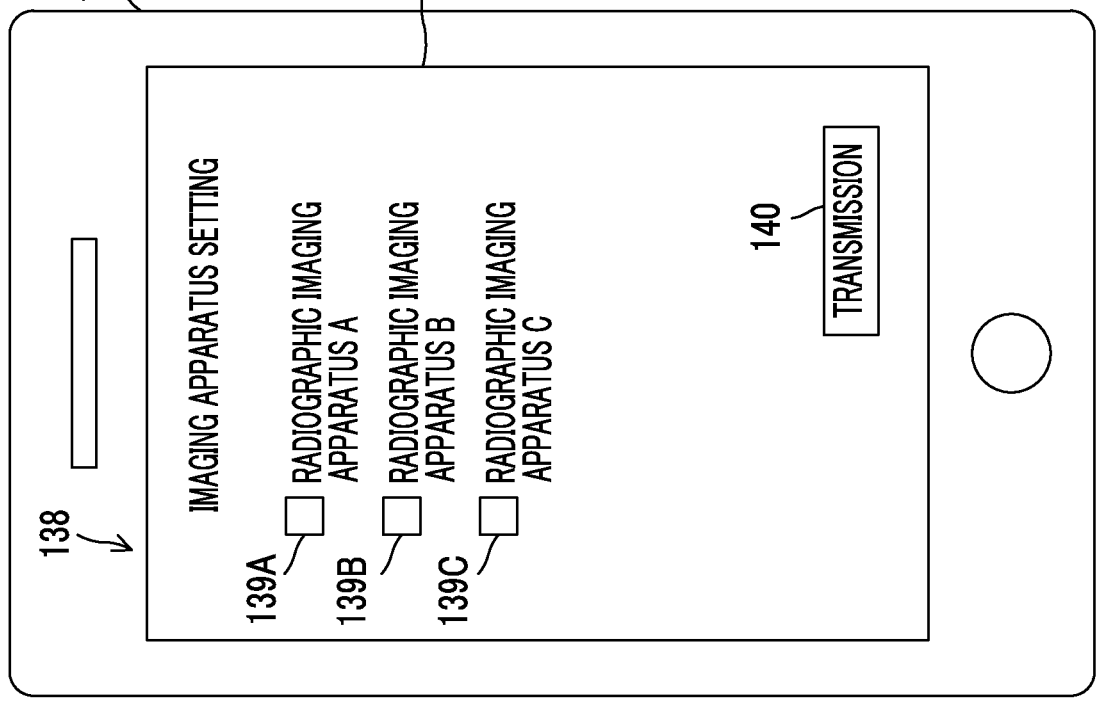
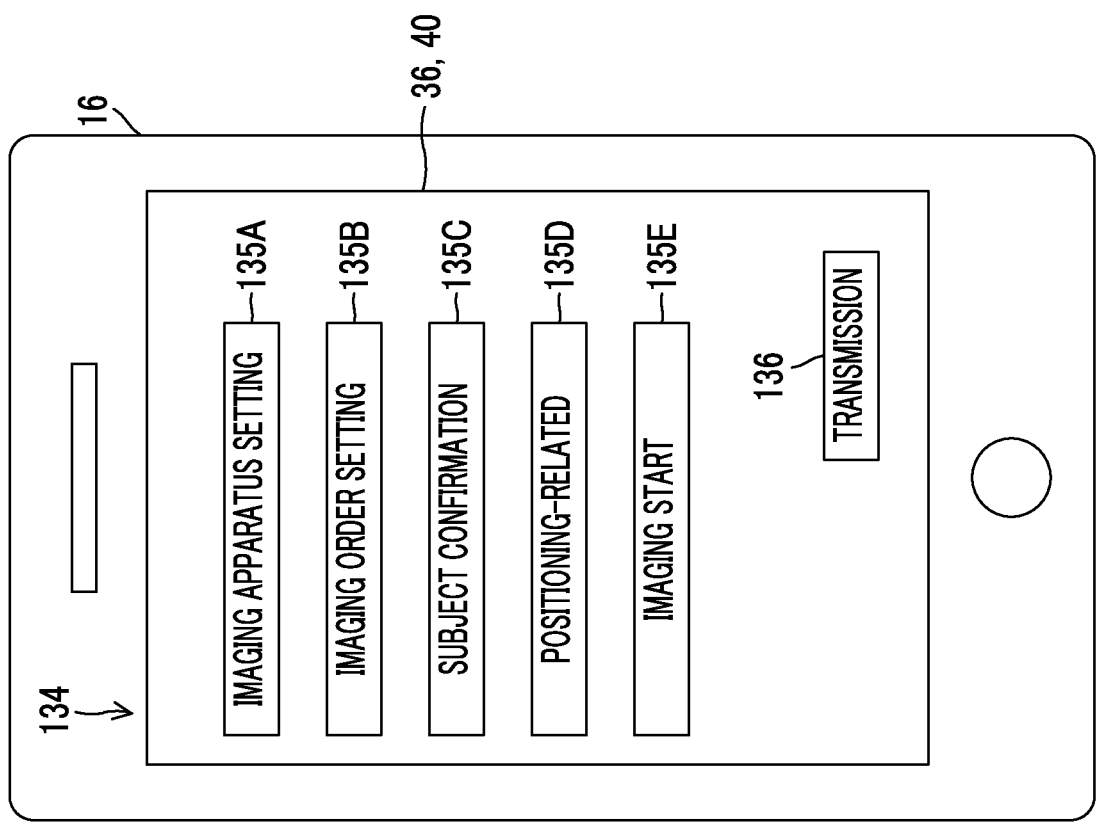

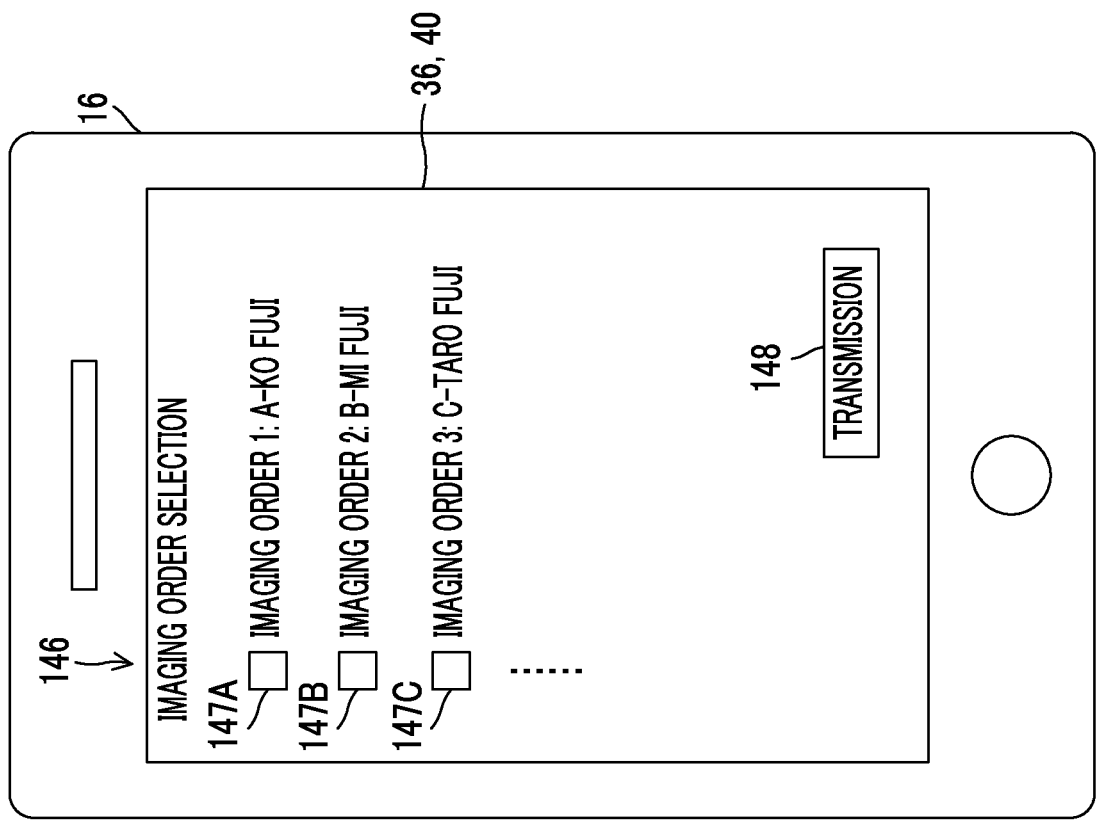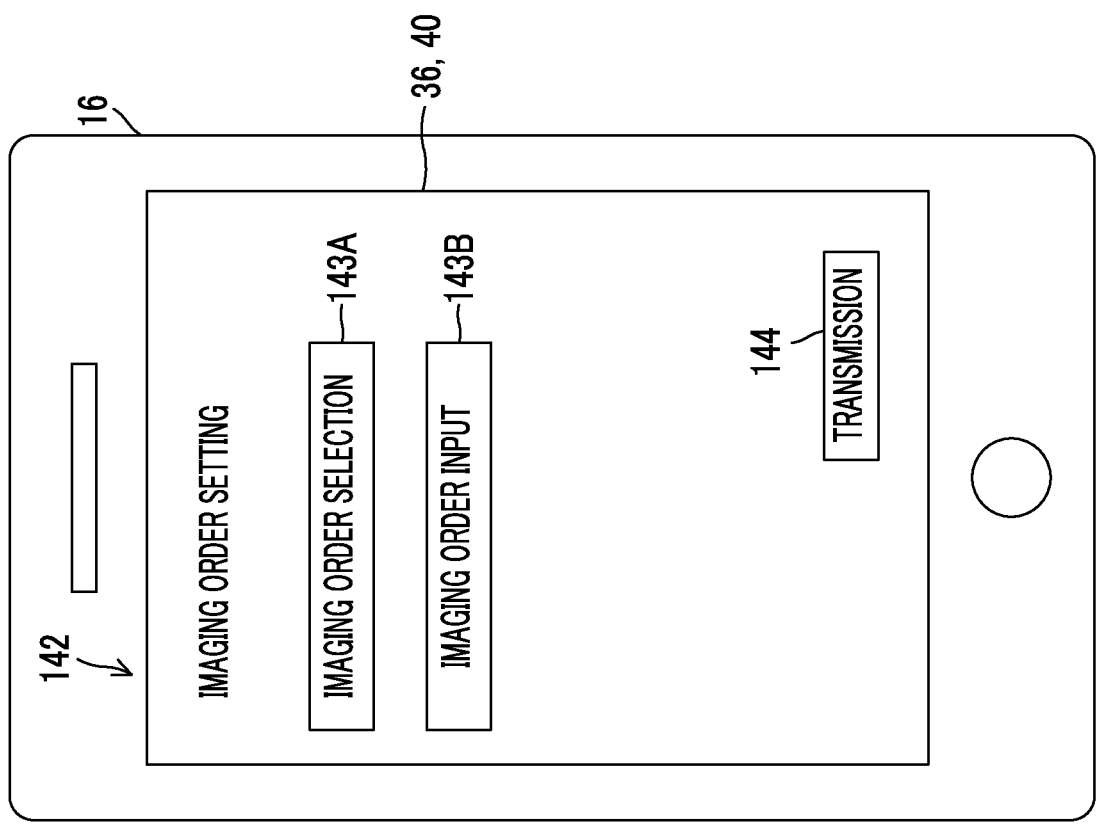

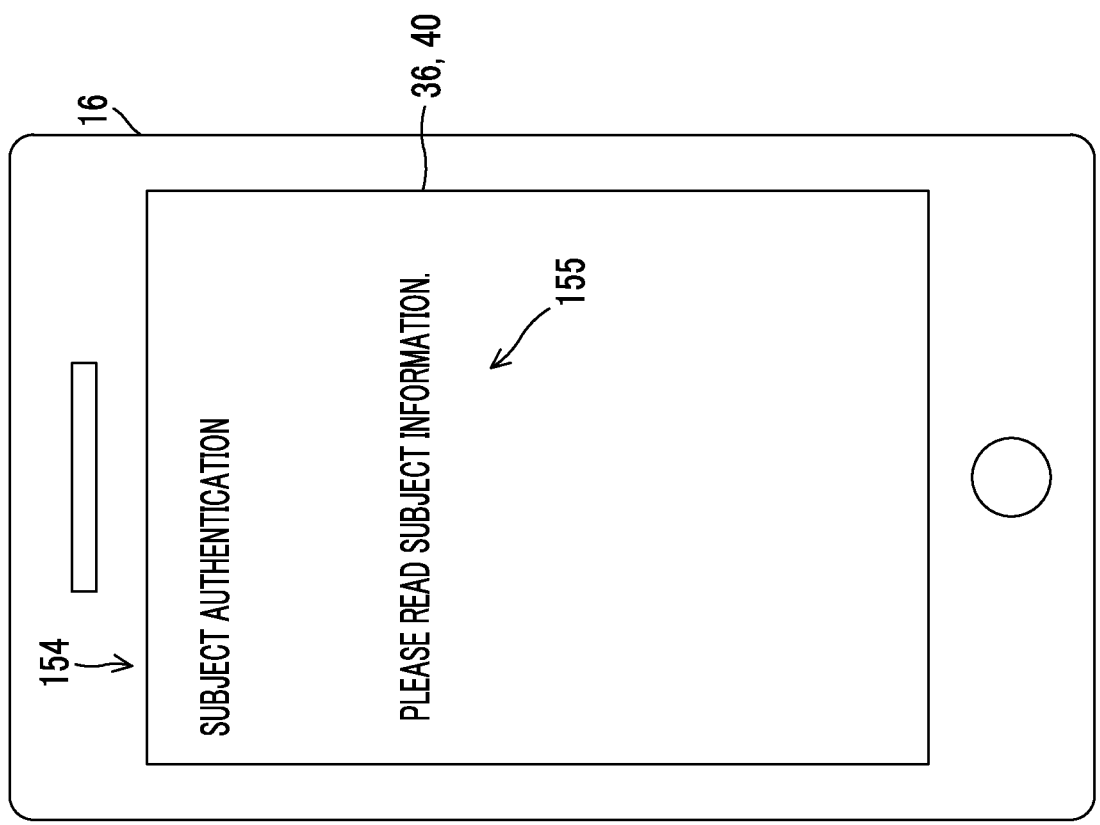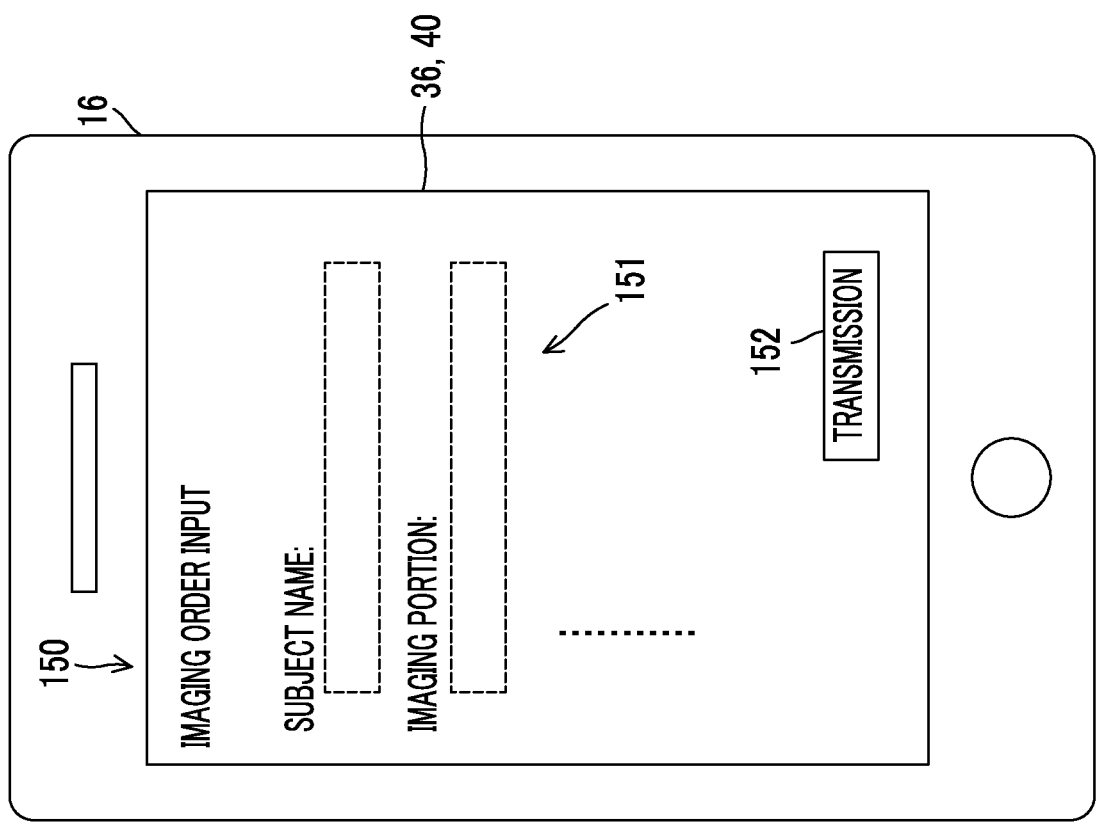

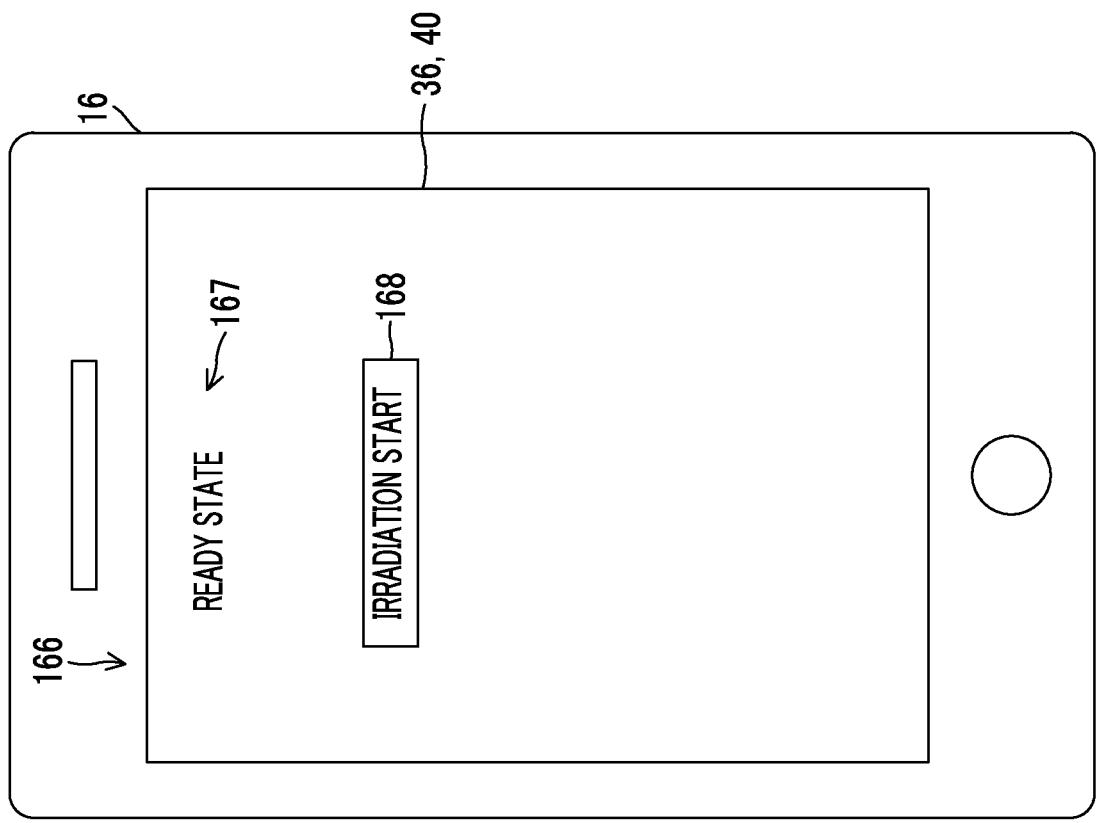
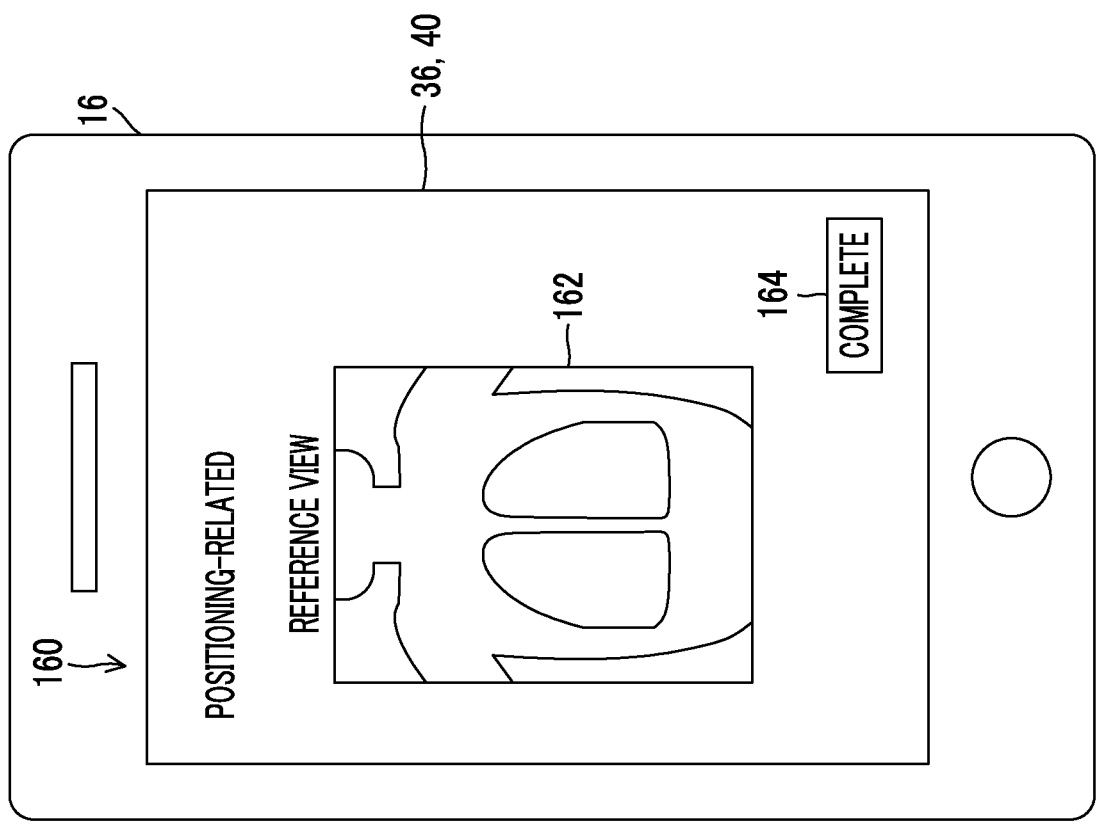

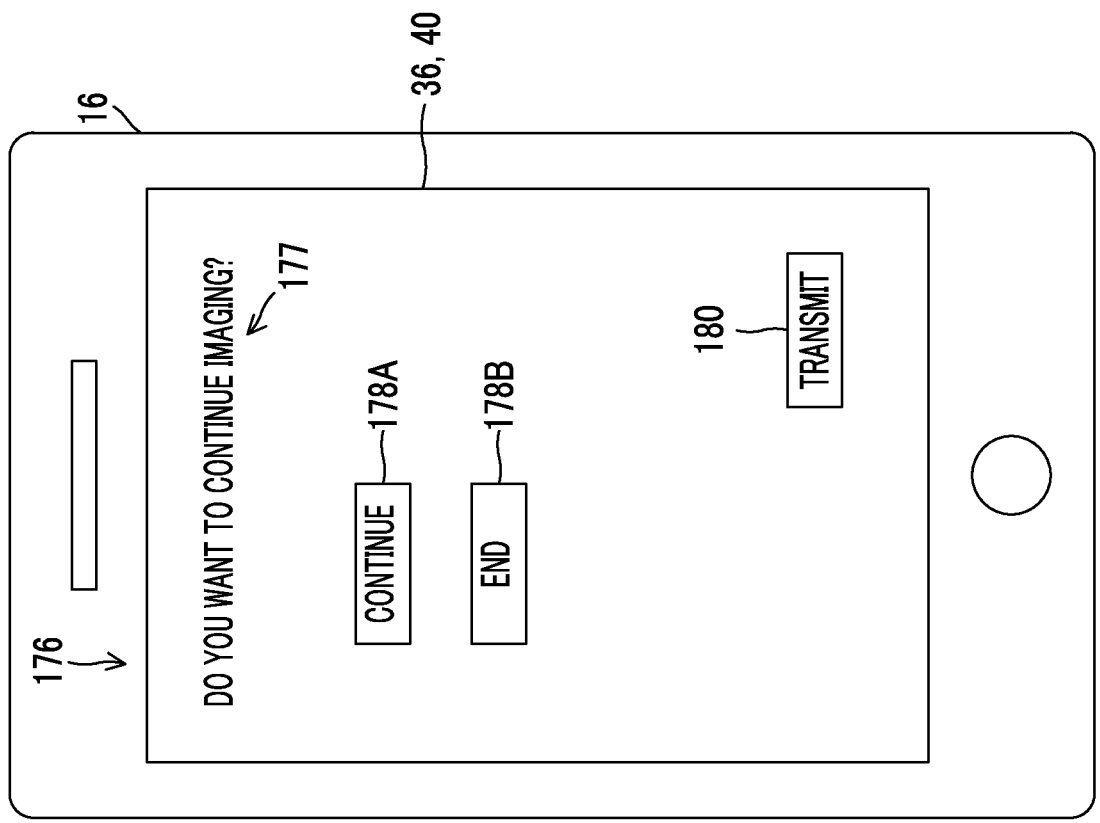
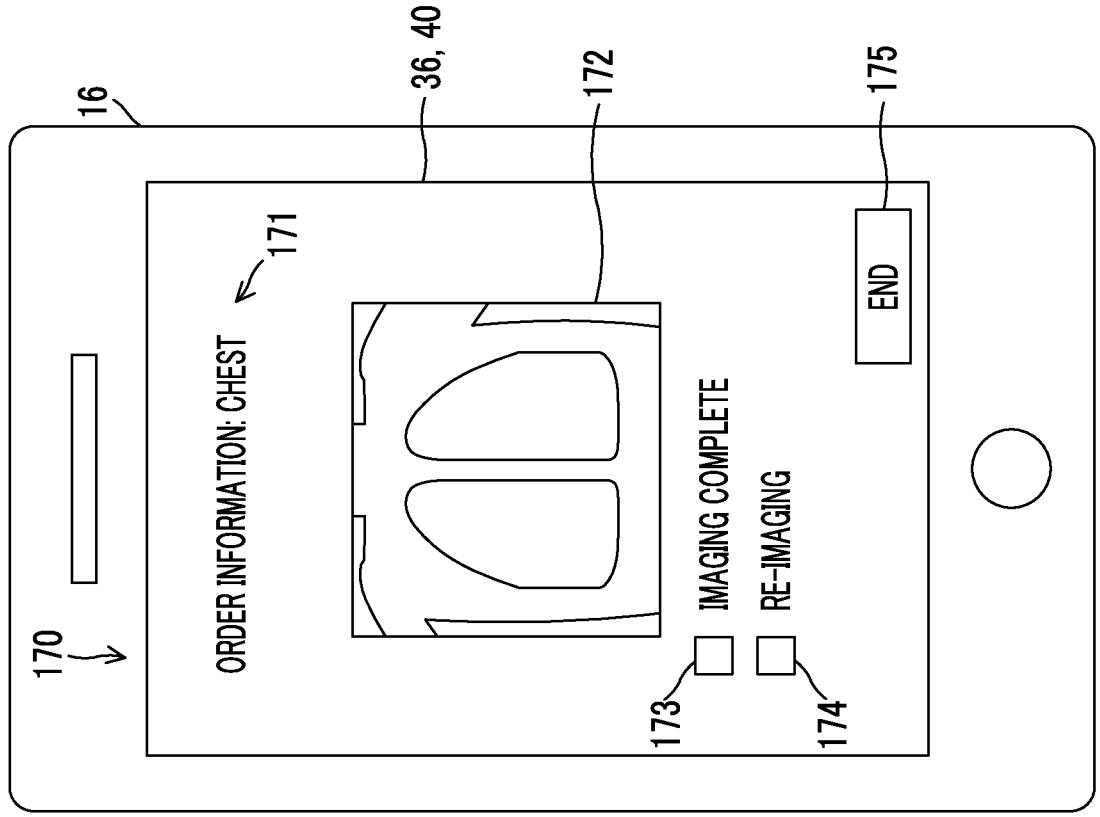

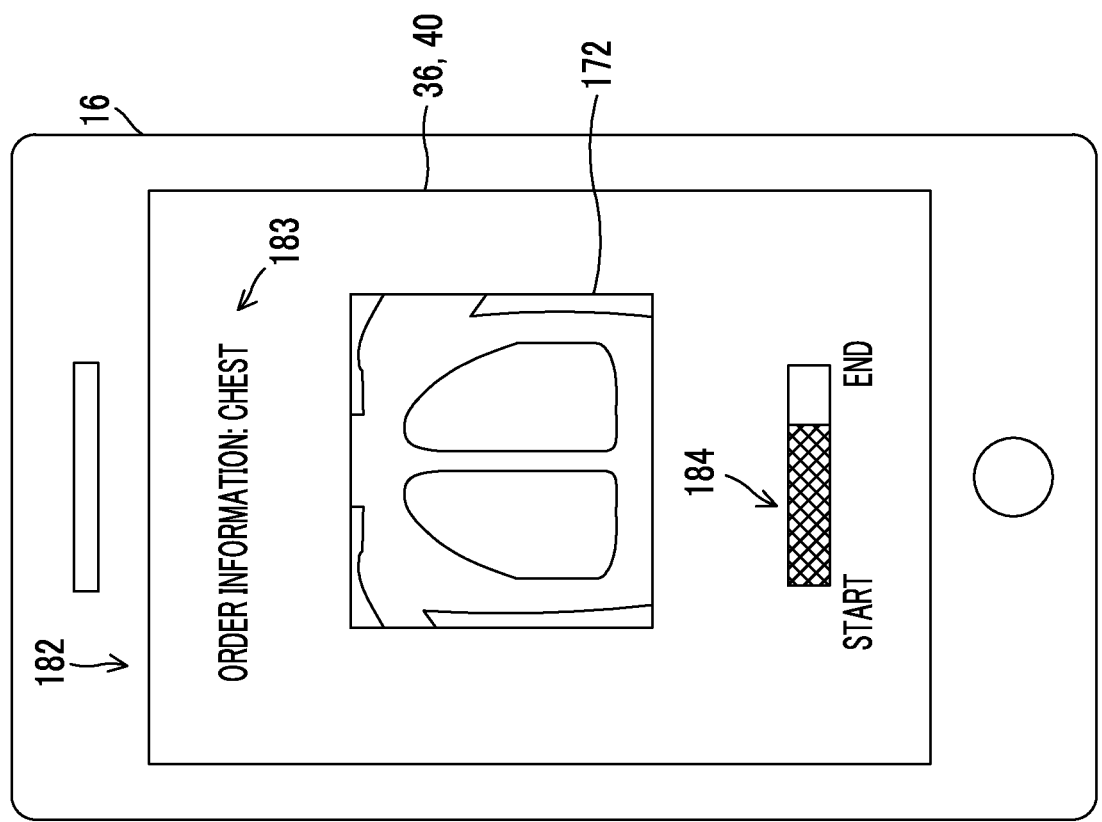

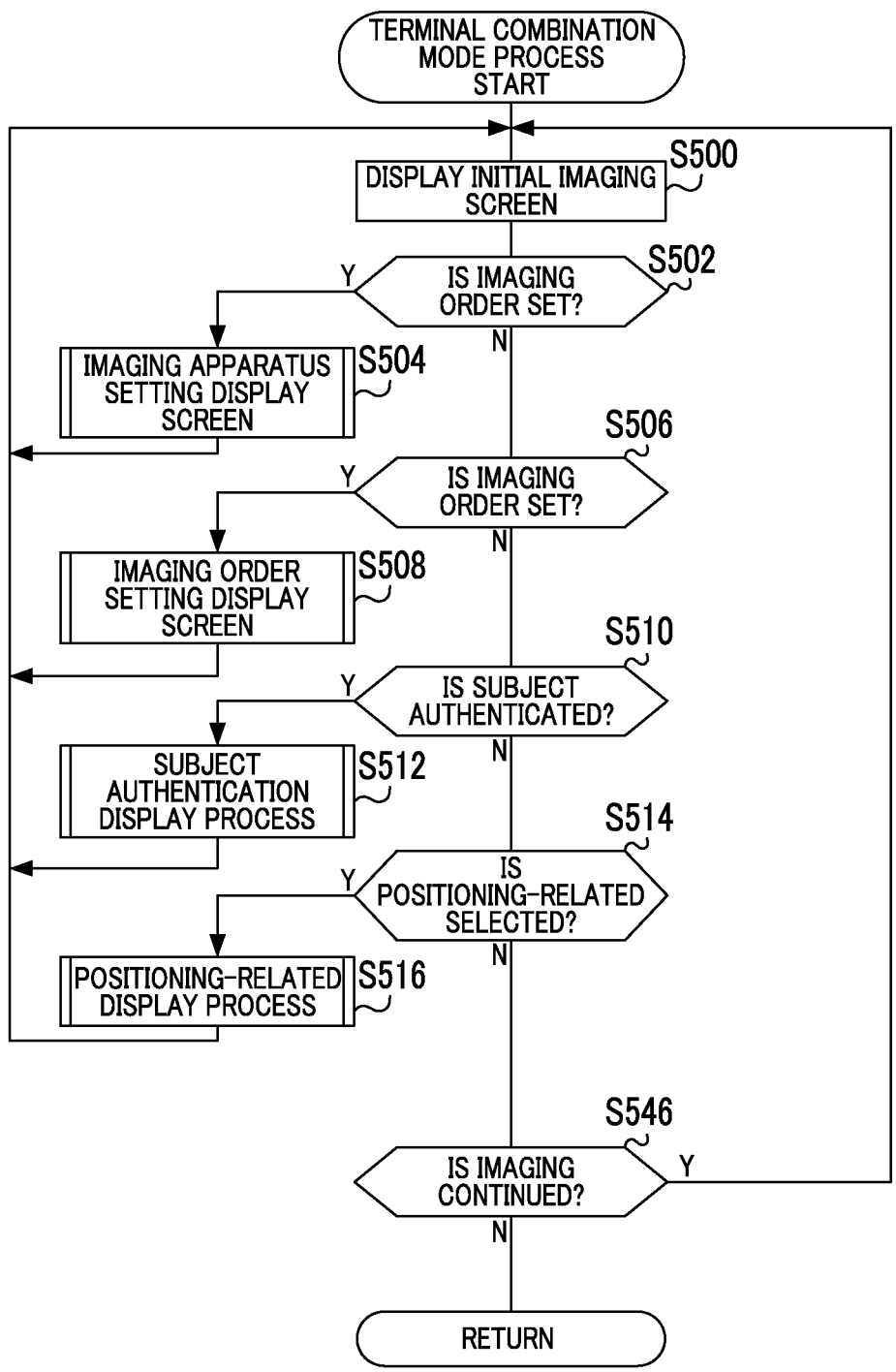

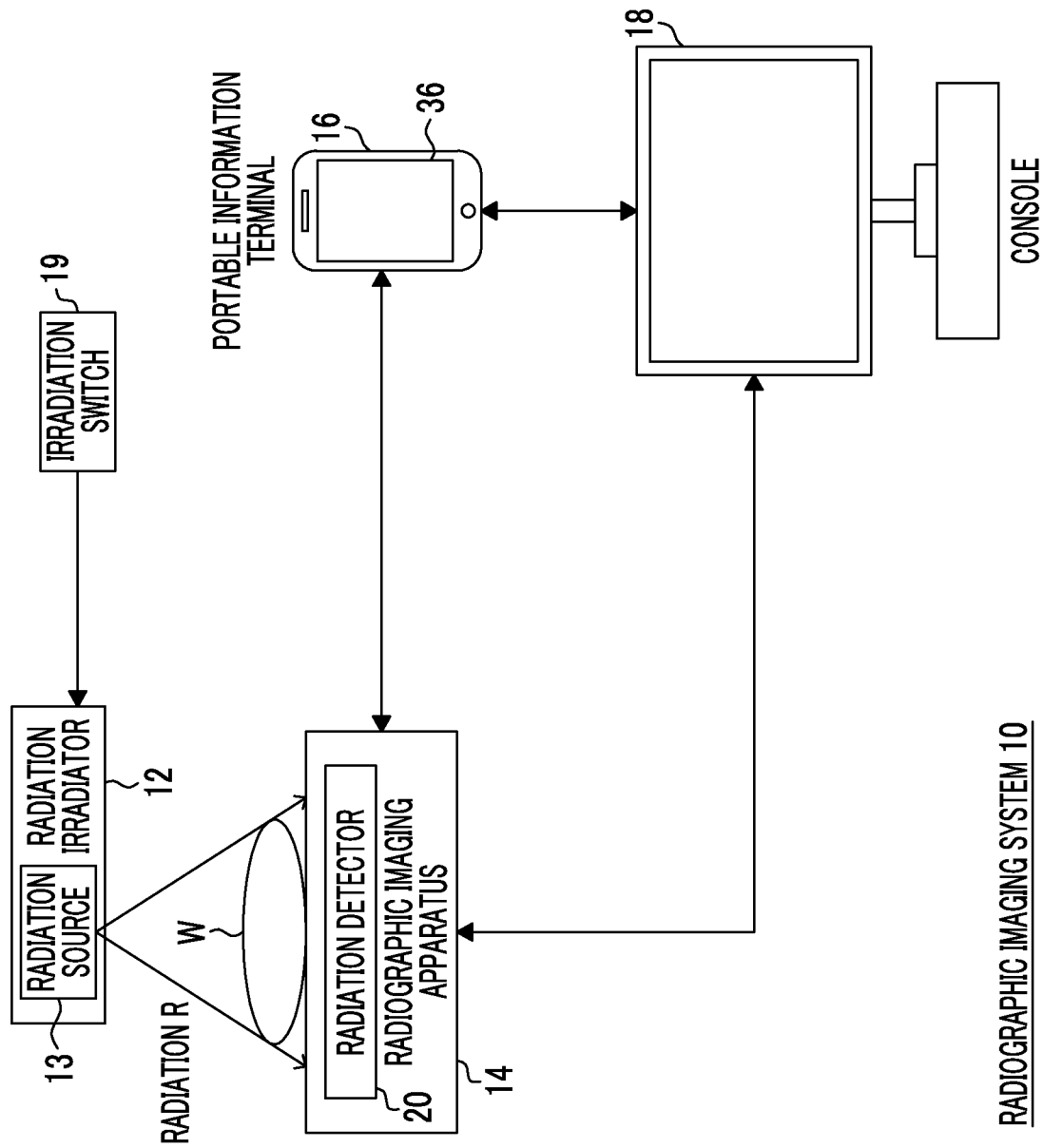

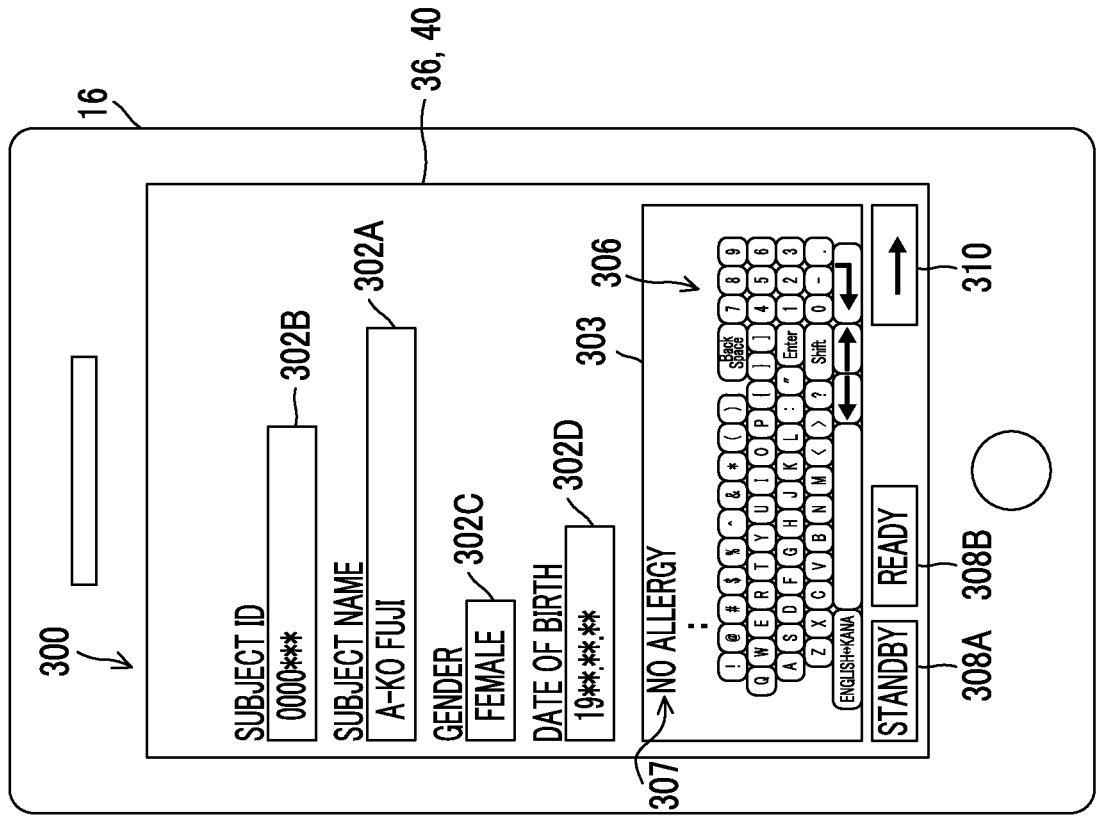
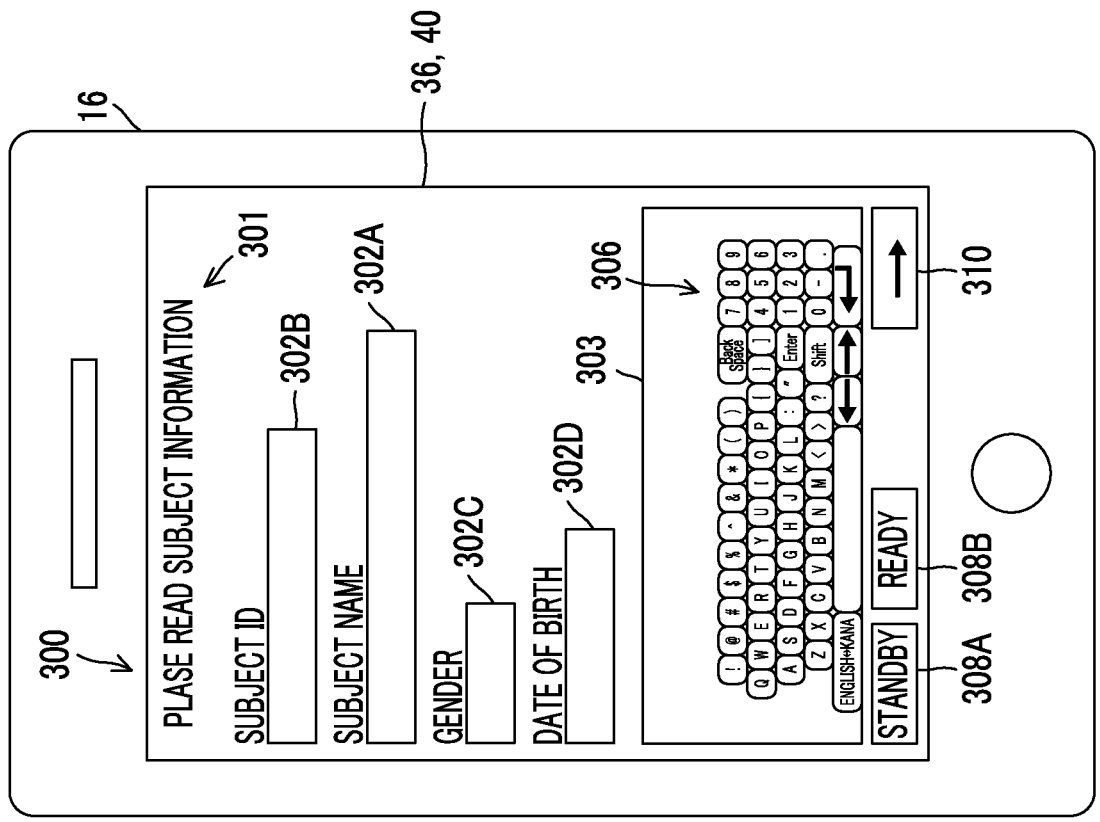

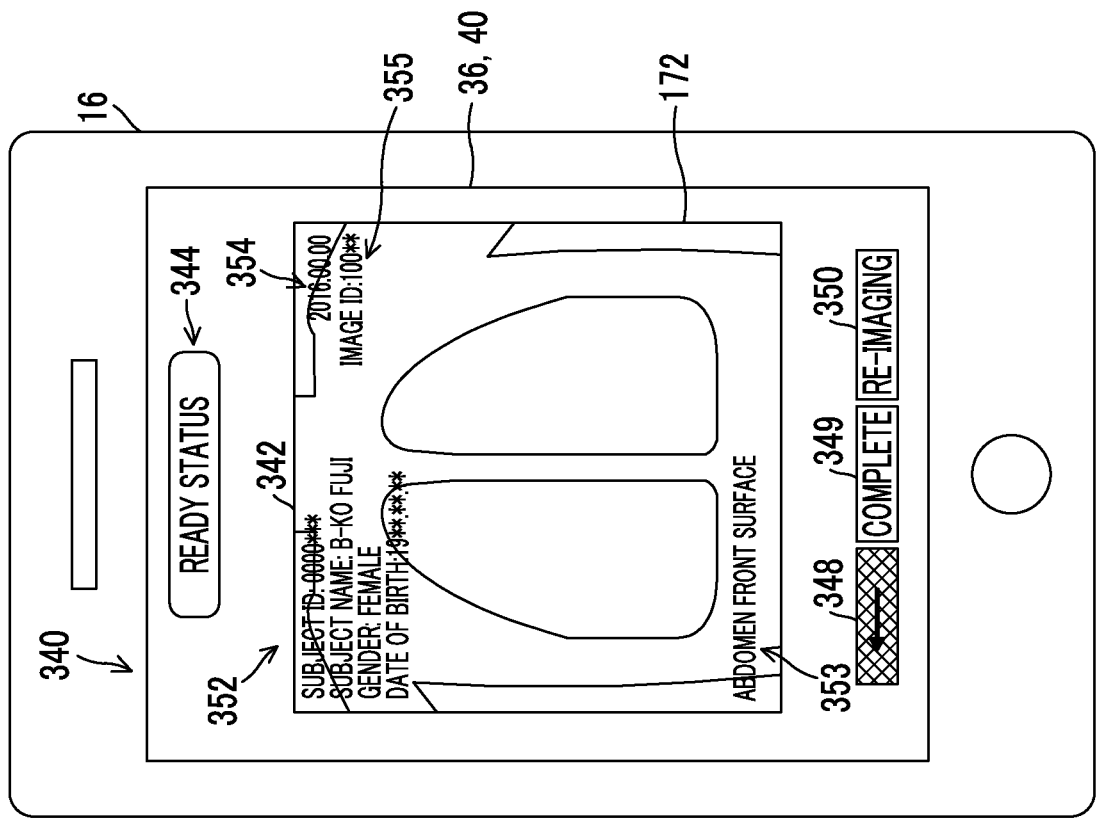
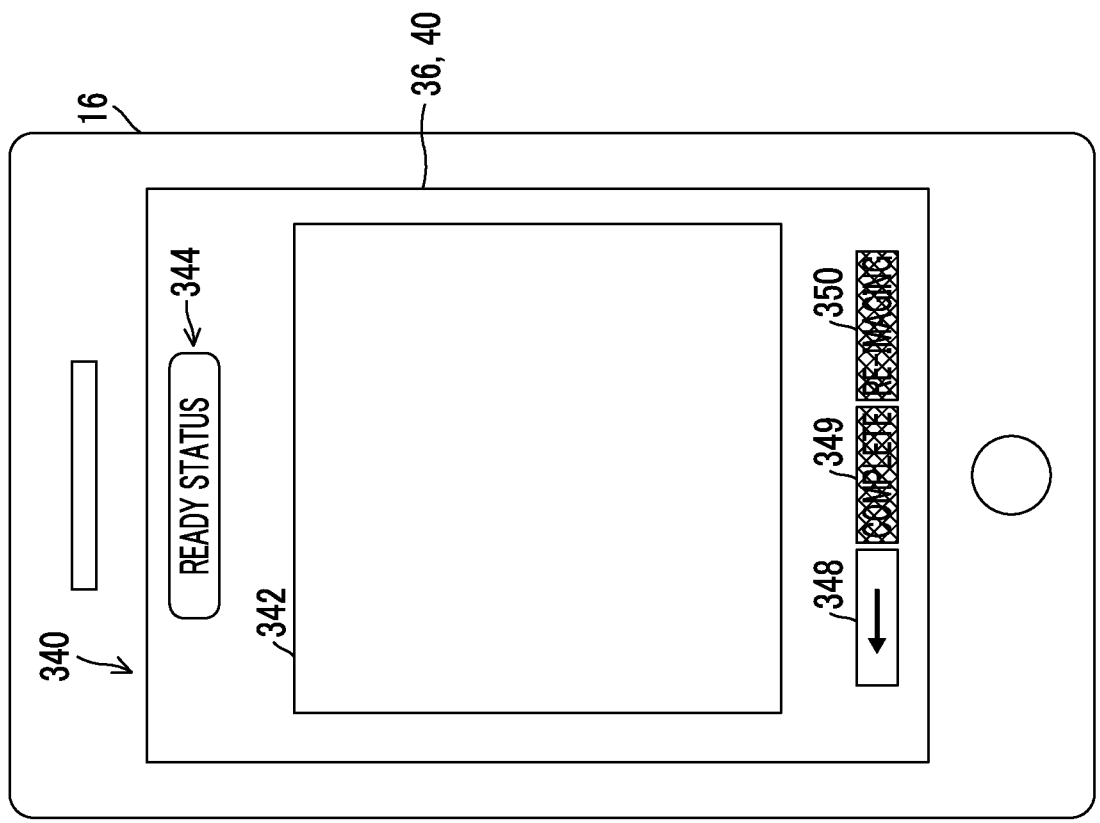

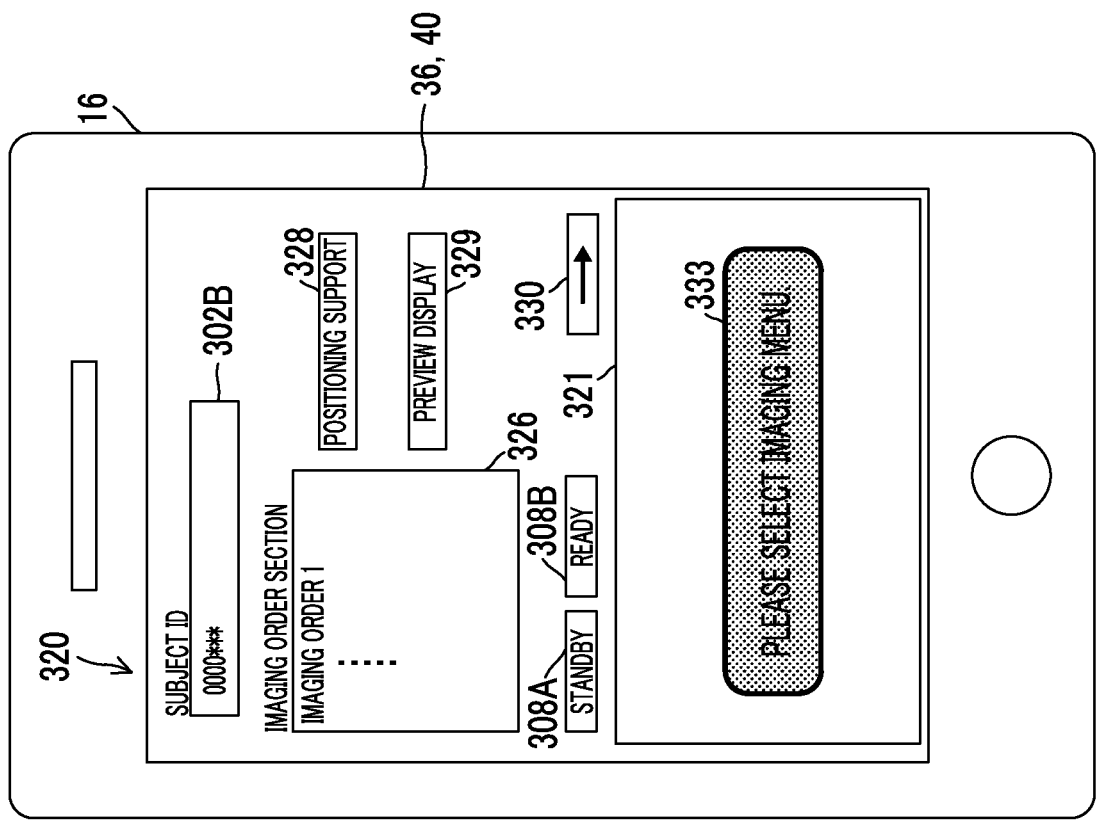
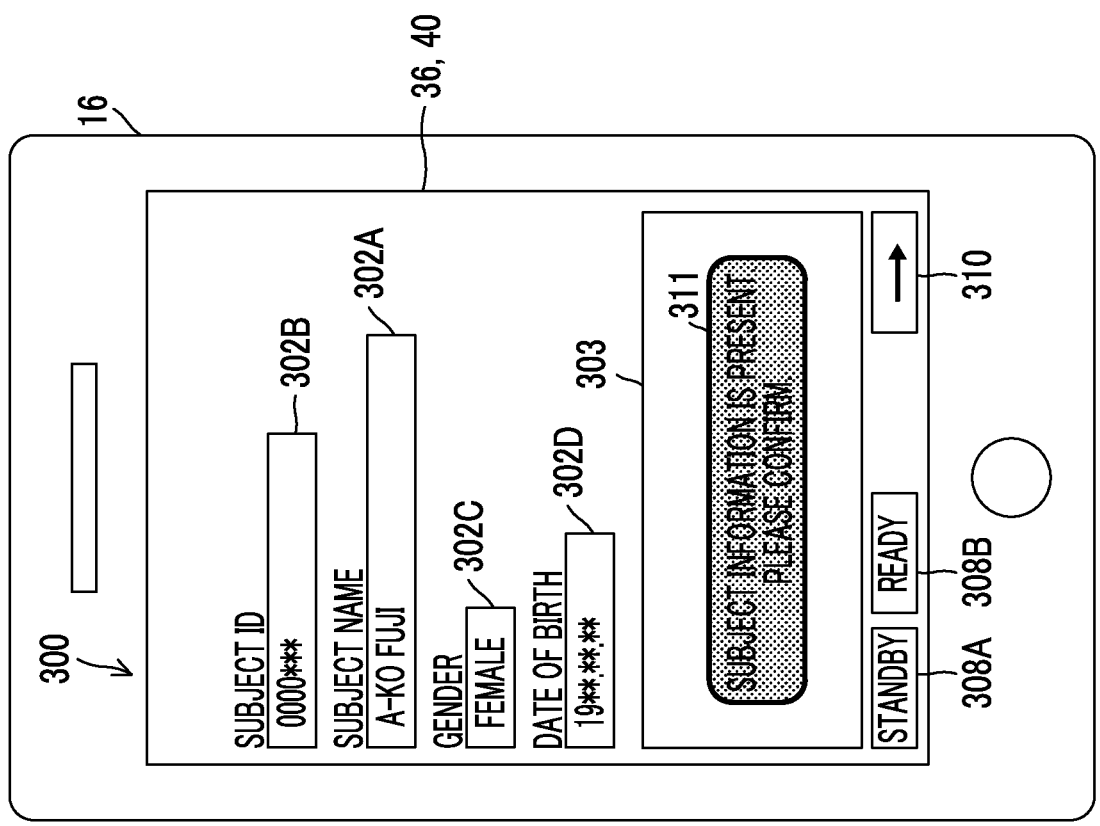

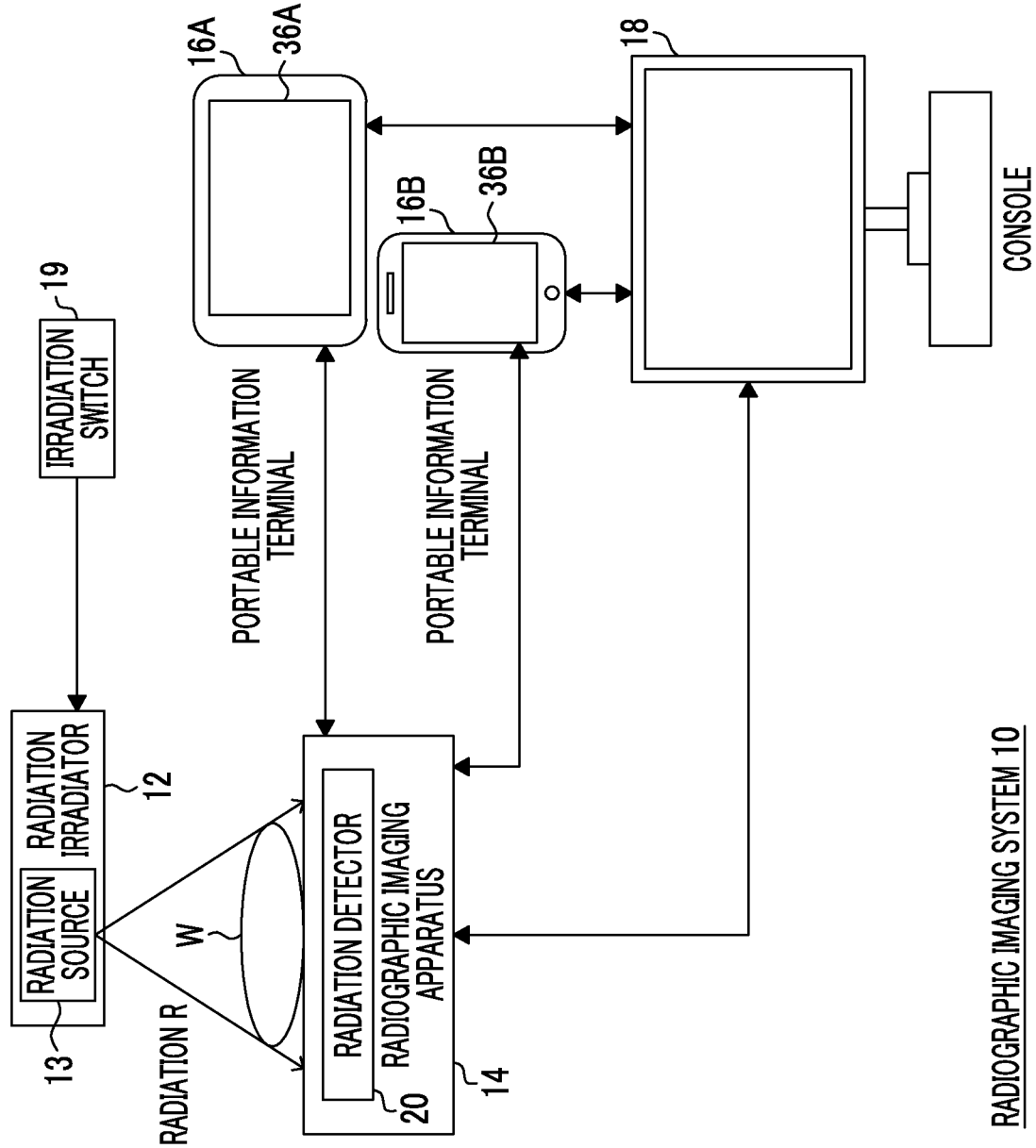

RADIOGRAPHIC IMAGING SYSTEM, CONTROL METHOD FOR RADIOGRAPHIC IMAGING SYSTEM, AND NON-TRANSITORY COMPUTER READABLE MEDIUM STORING A CONTROL PROGRAM FOR RADIOGRAPHIC IMAGING SYSTEM

CROSS-REFERENCE TO RELATED APPLICATIONS

This application is a Continuation of U.S. application Ser. No. 15/673,681, filed on Aug. 10, 2017, which claims priority under 35 U.S.C § 119(a) to Japanese Patent Application No. 2015-034497 filed on Feb. 24, 2015 and PCT International Application No. PCT/JP2016/053321 filed on Feb. 4, 2016. Each of the above application(s) is hereby expressly incorporated by reference, in its entirety, into the present application.

BACKGROUND OF THE INVENTION

1. Field of the Invention

The present invention relates to a radiographic imaging system, a control device, a control method for a radiographic imaging system, and a non-transitory computer readable medium storing a control program for the radiographic imaging system.

2. Description of the Related Art

In the related art, as a radiographic imaging apparatus that images a subject, a radiographic imaging apparatus that performs imaging for medical diagnosis is known. The radiographic imaging apparatus is configured so that radiation is emitted from a radiation irradiator and a radiation detector detects the radiation which has passed through a subject to generate a radiographic image.

As a control device that controls the radiographic imaging apparatus, a radiographic imaging system that includes plural control devices having different image processing functions may be used. For example, JP2013-111402A discloses a medical image broadcast system in which a console and a portable device are used as a control device.

SUMMARY OF THE INVENTION

In a radiographic imaging system including a plurality of control devices, in a case where imaging of a radiographic image is performed, there is a case where a plurality of control devices are combined for use, and also, there is a case where a single control device is used. In this way, in a case where control devices to be used for imaging of a radiographic image are different, there is a case where control content should be set with respect to the control devices. Further, there is a case where control content is set regardless of control devices to be used. Thus, a user may feel inconvenient usability, and thus, it is desirable to enhance the usability.

An object of the invention is to provide a technique capable of enhancing the usability of a radiographic imaging system for a user.

In order to solve the problem, according to an aspect of the invention, there is provided a radiographic imaging system comprising: a plurality of control devices of which each one includes a display unit and performs a control relating to imaging of a radiographic image and of which at least one is selectively used; and a setting unit that determines whether the number of usage control devices is one or plural and sets to the usage control device a control content to be displayed or not to be displayed on the display unit, wherein in a case where the number of usage control devices is one, based on the one usage device, the setting unit sets to the one usage control device a control content for displaying a first display content on the display unit of the one usage control device, and in a case where the number of usage control devices is plural, based on a combination of a plurality of usage control devices, the setting unit sets to each of the plurality of usage control devices a control content for displaying a second display content having a smaller amount of information than that of the first display content on each of display units of the plurality of usage control devices, or the setting unit sets to each of the plurality of usage control devices a control content of not displaying the first display content on each of display units of the plurality of usage control devices.

Further, in the radiographic imaging system according to this aspect of the invention, each of the plurality of control devices may include display unit having different display capability, and in a case where the number of usage control devices is plural, the setting unit may set to a usage control device which is provided with the display unit having relatively low display capability among the plurality of usage control devices a control content so that a display content displayed on the display unit of the usage control device provided with the display unit having a relatively low display capability among the plurality of usage control devices is smaller than a display content displayed on the display unit in a case where the number of usage control device is one.

Further, the radiographic imaging system according to this aspect of the invention may further comprise a control unit that controls, in a case where the number of usage control devices is plural, so that a display content which is predetermined to be displayed on the display unit of a usage control device and which overlaps a display content displayed on the display unit of a different usage control device is not to be noticeable compared with other of the display content.

Further, in the radiographic imaging system according to this aspect of the invention, in a case where the number of usage control devices is plural, the setting unit may set to a usage control device used in an imaging room in which imaging of a radiographic image is performed among the plurality of usage control devices, a display content that is determined in advance to be displayed in the imaging room.

Further, the radiographic imaging system according to this aspect of the invention may further comprise a display content reception unit that receives, in a case where the number of usage control devices is plural, an instruction for a display content to be displayed on a display unit of at least one usage control device among the plurality of usage control devices, in which the setting unit may set to the at least one usage control device the display content received by the display content reception unit.

Further, in the radiographic imaging system according to this aspect of the invention, in a case where the usage control devices are a plurality of control devices between which communication is possible, the setting unit may set to each of the usage control devices a control content based on a combination of the usage control devices with respect.

Further, the radiographic imaging system according to this aspect of the invention may further comprise a radiographic imaging apparatus that captures a radiographic image in one imaging mode selected from a plurality of imaging modes which are determined in advance with respect to imaging of a radiographic image, in which in a case where the imaging mode of the radiographic imaging apparatus is changed, the setting unit may set a control content of the usage control device.

Further, in the radiographic imaging system according to this aspect of the invention, the plurality of imaging modes may include a memory mode in which image data of a plurality of radiographic images obtained through imaging is stored in a storage unit which is integrally formed with the radiographic imaging apparatus, and in a case where the imaging mode of the radiographic imaging apparatus is changed to the memory mode, the setting unit may set the control content of the usage control device to a control content based on the one usage control device.

Further, the radiographic imaging system according to this aspect of the invention may further comprise a control content reception unit that receives the control content, in which the setting unit may set to the usage control device the control content received by the control content reception unit.

In addition, in the radiographic imaging system according to this aspect of the invention, in a case where the number of usage control devices is plural, the setting unit may be provided in at least one usage control device among the plurality of usage control devices.

Furthermore, in the radiographic imaging system according to this aspect of the invention, in a case where the number of usage control devices is plural, at least one usage control device may be a portable control device.

According to another aspect of the invention, there is provided a radiographic imaging system comprising: a plurality of control devices that include a portable control device and a non-portable control device, in which each of the plurality of control devices includes a display unit and performs a control relating to imaging of a radiographic image, and at least one of the plurality of control devices is selectively used; and a setting unit that sets to usage control devices which are control devices to be selectively used, a display content to be displayed on a display unit of each usage control device, on the basis of whether the usage control device is the portable usage control device or the non-portable usage control device and of whether the number of usage control devices is one or plural, in a case where the number of usage control devices is one, the setting unit sets to the one usage control device a control content for displaying a first display content corresponding to the one usage control device on the display unit of the one usage control device, and in a case where the number of usage control devices is plural, based on a combination of a plurality of usage control devices, the setting unit sets to each of the plurality of usage control devices a control content for displaying a second display content having a smaller amount of information than that of the first display content on each of display units of the plurality of usage control devices, or the setting unit sets to each of the plurality of usage control devices a control content of not displaying the first display content on each of display units of the plurality of usage control devices.

In the radiographic imaging system according to this aspect of the invention, a display content to be displayed on the display unit of the usage control device in the case of the portable control device may have a smaller amount of information than that of a display content to be displayed on the display unit of the usage control device in the case of the non-portable control device.

Further, in the radiographic imaging system according to this aspect of the invention, the display content to be displayed on the display unit of the usage control device in the case of the portable control device may have a smaller amount of information than that of display content of the same item to be displayed on the display unit of the usage control device in the case of the non-portable control device.

According to a still another aspect of the invention, there is provided a radiographic imaging system comprising: a non-portable control device that includes a first display unit that displays information relating to imaging of a radiographic image, in which a first display content is displayed on the first display unit in a case where a control relating to imaging of a radiographic image is independently performed, and a second display content having a smaller amount of information than that of the first display content is displayed on the first display unit in a case where a control relating to imaging of a radiographic image is performed in combination with a different control device; and a portable control device that includes a second display unit that displays information relating to imaging of a radiographic image and has a display capability lower than that of the first display unit, in which a third display content having a smaller amount of information than that of the first display content is displayed on the second display unit in a case where a control relating to imaging of a radiographic image is independently performed, and a fourth display content having a smaller amount of information than those of both the second display content and the third display content is displayed on the second display unit in a case where a control relating to imaging of a radiographic image is performed in combination with a different control device.

Further, in the radiographic imaging system according to this aspect of the invention, the portable control device may include a battery for supplying power used for driving of the host device.

According to still another aspect of the invention, there is provided a radiographic imaging system comprising: a control device that includes a display unit and has a plurality of control units of which each one performs a control relating to imaging of a radiographic image and of which at least one is selectively used; and a setting unit that determines whether the number of usage control units is one or plural, and sets to the usage control unit a control content to be displayed or not to be displayed on the display unit, wherein in a case where the number of usage control units is one, based on the one usage unit, the setting unit sets to the one usage control unit a control content for displaying a first display content on the display unit, and in a case where the number of usage control units is plural, based on a combination of a plurality of usage control units, the setting unit sets to each of the plurality of usage control units a control content for displaying a second display content having a smaller amount of information than that of the first display content on the display unit, or the setting unit sets to each of the plurality of usage control units a control content of not displaying the first display content on the display unit.

According to still another aspect of the invention, there is provided a control device which is one of a plurality of control devices of which each one includes a display unit and performs a control relating to imaging of a radiographic image and of which at least one is selectively used, comprising: a setting unit that determines whether the number of usage control devices is one or plural, and sets to the usage control device a control content to be displayed or not to be displayed on the display unit, wherein in a case where the number of usage control devices is one, based on the one usage device, the setting unit sets to the one usage control device a control content for displaying a first display content on the display unit of the one usage control device, and in a case where the number of usage control devices is plural, based on a combination of a plurality of usage control devices, the setting unit sets to each of the plurality of usage control devices a control content for displaying a second display content having a smaller amount of information than that of the first display content on each of display units of the plurality of usage control devices, or the setting unit sets to each of the plurality of usage control devices a control content of not displaying the first display content on each of display units of the plurality of usage control devices.

According to still another aspect of the invention, there is provided a control method for a radiographic imaging system including a plurality of control devices of which each one includes a display and performs a control relating to imaging of a radiographic image and of which at least one is selectively used, the method causing a computer to execute processes comprising: determining whether the number of usage control devices is one or plural, and setting to the usage control device a control content to be displayed or not to be displayed on the display unit, wherein in a case where the number of usage control devices is one, based on the one usage device, setting to the one usage control device a control content for displaying a first display content on the display unit of the one usage control device, and in a case where the number of usage control devices is plural, based on a combination of a plurality of usage control devices, setting to each of the plurality of usage control devices a control content for displaying a second display content having a smaller amount of information than that of the first display content on each of display units of the plurality of usage control devices, or setting to each of the plurality of usage control devices a control content of not displaying the first display content on each of display units of the plurality of usage control devices.

According to still another aspect of the invention, there is provided a non-transitory computer readable medium storing a control program for a radiographic imaging system including a plurality of control devices of which each one includes a display unit and performs a control relating to imaging of a radiographic image and of which at least one is selectively used, the program causing a computer to execute processes comprising: determining whether the number of usage control devices is one or plural, and setting to the usage control device a control content to be displayed or not to be displayed on the display unit, wherein in a case where the number of usage control devices is one, based on the one usage device, setting to the one usage control device a control content for displaying a first display content on the display unit of the one usage control device, and in a case where the number of usage control devices is plural, based on a combination of a plurality of usage control devices, setting to each of the plurality of usage control devices a control content for displaying a second display content having a smaller amount of information than that of the first display content on each of display units of the plurality of usage control devices, or setting to each of the plurality of usage control devices a control content of not displaying the first display content on each of display units of the plurality of usage control devices.

According to the invention, it is possible to obtain an effect of enhancing the usability of a radiographic imaging apparatus for a user.

BRIEF DESCRIPTION OF THE DRAWINGS

FIG. 5A is a flowchart illustrating an example of a flow of a console single mode process and a console combination mode process executed by the control unit of the console of the first embodiment.

FIG. 24 is a schematic diagram illustrating a specific example of a state where a control mode confirmation screen is displayed on a display of the portable information terminal.

FIG. 26 is a schematic diagram illustrating a specific example of a state where an initial imaging screen is displayed on the display of the portable information terminal.

FIG. 27 is a schematic diagram illustrating a specific example of a state where an imaging apparatus setting screen is displayed on the display of the portable information terminal.

FIG. 28 is a schematic diagram illustrating a specific example of a state where an imaging order setting screen is displayed on the display of the portable information terminal.

FIG. 29 is a schematic diagram illustrating a specific example of a state where an imaging order select screen is displayed on the display of the portable information terminal.

FIG. 30 is a schematic diagram illustrating a specific example of a state where an imaging order input screen is displayed on the display of the portable information terminal.

FIG. 31 is a schematic diagram illustrating a specific example of a state where a subject authentication screen is displayed on the display of the portable information terminal.

FIG. 34 is a schematic diagram illustrating a specific example of a state where a positioning related screen is displayed on the display of the portable information terminal.

FIG. 35 is a schematic diagram illustrating a specific example of a state where an imaging start screen is displayed on the display of the portable information terminal.

FIG. 36 is a schematic diagram illustrating a specific example of a state where an image confirmation screen is displayed on the display of the portable information terminal.

FIG. 37 is a schematic diagram illustrating a specific example of a state where an imaging continuation confirmation screen is displayed on the display of the portable information terminal.

FIG. 38 is a schematic diagram illustrating a specific example of a state where an imaging status screen indicating information relating to an imaging status on the display of the portable information terminal.

FIG. 39 is a flowchart illustrating an example of a flow of a terminal combination mode process executed by the terminal control unit of the portable information terminal of the first embodiment.

FIG. 40 is a schematic configuration diagram illustrating an example of a radiographic imaging system according to a second embodiment.

FIG. 57 is a schematic diagram showing a specific example of a state where a subject information registration screen in a terminal single mode process is displayed on the display of the portable information terminal.

FIG. 58 is a schematic diagram showing a specific example of a state where imaging order information is displayed on the subject information registration screen.

FIG. 61 is a schematic diagram illustrating a specific example of a state where an imaging confirmation screen is displayed on the display of the portable information terminal.

FIG. 62 is a schematic diagram illustrating a specific example of a state where a preview image is displayed on the imaging confirmation screen.

FIG. 63 is a schematic diagram illustrating a specific example of a state where a subject information registration screen in a terminal combination mode process is displayed on the display of the portable information terminal.

FIG. 64 is a schematic diagram illustrating a specific example of a state where a menu select screen in the terminal combination mode process is displayed on the display of the portable information terminal.

FIG. 65 is a schematic configuration diagram illustrating an example of a radiographic imaging system in a case where a plurality of portable information terminals are provided.

Figure 1:
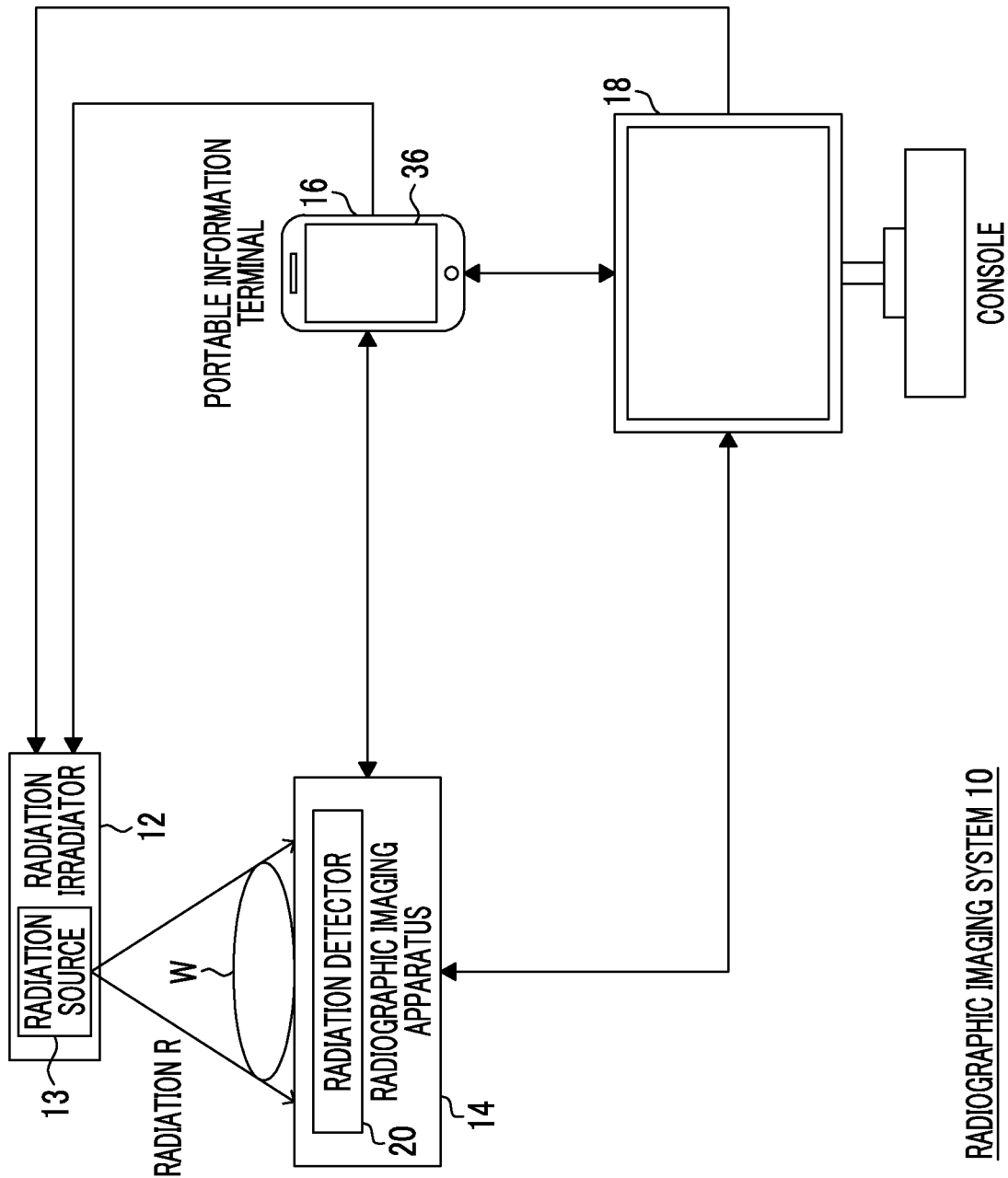
FIG. 1 is a schematic configuration diagram illustrating an example of a radiographic imaging system of a first embodiment.

DESCRIPTION OF THE PREFERRED
EMBODIMENTS

Hereinafter, examples of embodiments according to the invention will be described with reference to the accompanying drawings. In the figures, the same reference numerals are given to components having the same functions, and repetitive description thereof will not be made.

First Embodiment

First, a schematic configuration of a radiographic imaging system of a first embodiment will be described. FIG. 1 is a schematic configuration diagram illustrating an example of a radiographic imaging system of this embodiment.

A radiographic imaging system 10 includes a radiation irradiator 12, a radiographic imaging apparatus 14, a portable information terminal 16, and a console 18. In FIG. 1, one radiographic imaging apparatus 14, one portable information terminal 16, and one console 18 are shown, respectively, but the numbers thereof provided in the radiographic imaging system 10 are not particularly limited. A plurality of radiographic imaging apparatuses 14, a plurality of portable information terminals 16, and a plurality of consoles 18 may be respectively provided. Further, the radiographic imaging apparatus 14, the portable information terminal 16, and the console 18 may not be the same in their numbers. For example, only the radiographic imaging apparatus 14 may be provided in a plurality.

The radiation irradiator 12 includes a radiation source 13. The radiation irradiator 12 has a function of irradiating a subject W with radiation R (for example, X-ray) from the radiation source 13. As a specific example of the radiation irradiator 12, a mobile car may be used, for example. A method for instructing the radiation irradiator 12 to execute the irradiation of the radiation R is not particularly limited, but in this embodiment, an irradiation execution instruction is performed from the portable information terminal 16 or the console 18.

The radiographic imaging apparatus 14 includes a radiation detector 20 that detects radiation R that is emitted from the radiation irradiator 12 and passes through the subject W. The radiographic imaging apparatus 14 has a function of generating a radiographic image of the subject W using the radiation detector 20. In this embodiment, an electronic cassette is used as the radiographic imaging apparatus 14.

The portable information terminal 16 of this embodiment is a portable control device. In this embodiment, the "portable" means that a user such as an engineer can wear and carry the device.

Further, the "portable" control device may be driven by a built-in battery, or may be driven by an external power source. The portable information terminal 16 of this embodiment may be driven by a built-in battery 39, and specifically, a tablet terminal, a smart phone which is a so-called personal digital assistant (PDA), or the like may be used. The portable information terminal 16 has a function of performing a control relating to imaging of a radiographic image using the radiographic imaging apparatus 14 on the basis of order information regarding an imaging order input through an external system such as a radiology information system (RIS) or the console 18. Thus, the portable information terminal 16 can receive the order information regarding the imaging order from the external system or the console 18. A specific type or the like of the portable information terminal 16 is not particularly limited, and for example, may be a versatile PDA or a tablet terminal, or may be a dedicated terminal (for example, dedicated to medical treatment or dedicated to radiographic imaging system 10). Since there is a case where the portable information terminal 16 is used in a medical field or near the subject W, it is preferable to perform a waterproofing or antibacterial processing on the surface thereof.

The console 18 has a function of controlling the entirety of the radiographic imaging system 10 or a function of controlling imaging of a radiographic image using the radiographic imaging apparatus 14, on the basis of order information input through an external system such as an RIS, for example. Thus, the console 18 can receive the order information from the external system.

In the radiographic imaging system 10 of this embodiment, in a case where the imaging of the radiographic image is performed at a predetermined imaging location such as a hospital ward, a hospital room, or an operating room, the radiation irradiator 12, the radiographic imaging apparatus 14, and the portable information terminal 16 are disposed at the imaging location to perform the imaging of the radiographic image. In this case, the console 18 performs the imaging in a state of being disposed at a location (for example, in a clinic or the like of the department of radiology) different from the imaging location where the radiation irradiator 12, the radiographic imaging apparatus 14, and the portable information terminal 16 are disposed.

In the radiographic imaging system 10 of this embodiment, the portable information terminal 16 and the console 18 have different control functions for performing a control relating to imaging of a radiographic image. In this embodiment, the control relating to the imaging of the radiographic image includes a control of operations of the radiation irradiator 12 and the radiographic imaging apparatus 14, and a control relating to display such as display of a variety of information relating to imaging or display for prompting a user to perform an operation.

The portable information terminal 16 only has a partial control function among the control functions relating to the imaging of the radiographic image provided in the console 18. Each of the portable information terminal 16 and the console 18 is an example of a control device of the invention. In this embodiment, the portable information terminal 16 and the console 18 may be referred to as "control devices" without distinction. Among a plurality of control devices provided in the radiographic imaging system 10, a control device that is selectively used in a case where imaging of a radiographic image is performed and performs the control relating to the imaging of the radiographic image corresponds to an example of a "usage control device" of the invention.

Further, in the radiographic imaging system 10 of this embodiment, as the control relating to the imaging of the radiographic image, three types of control modes such as a console single mode, a terminal single mode, and a combination mode are used. The control mode of this embodiment corresponds to control content of the invention. The console single mode is a control mode in which only the console 18 performs the control relating to the imaging of the radiographic image. The terminal single mode is a control mode in which only the portable information terminal 16 performs the control relating to the imaging of the radiographic image. The combination mode is a control mode in which the portable information terminal 16 and the console 18 perform the control relating to the imaging of the radiographic image. In the combination mode, the console 18 mainly performs the control relating to the imaging of the radiographic image, and the portable information terminal 16 functions to support the console 18. In the radiographic imaging system 10 of this embodiment, as a specific example, the combination mode may be used in a case where communication between the portable information terminal 16 and the console 18 is possible.

Figure 2:
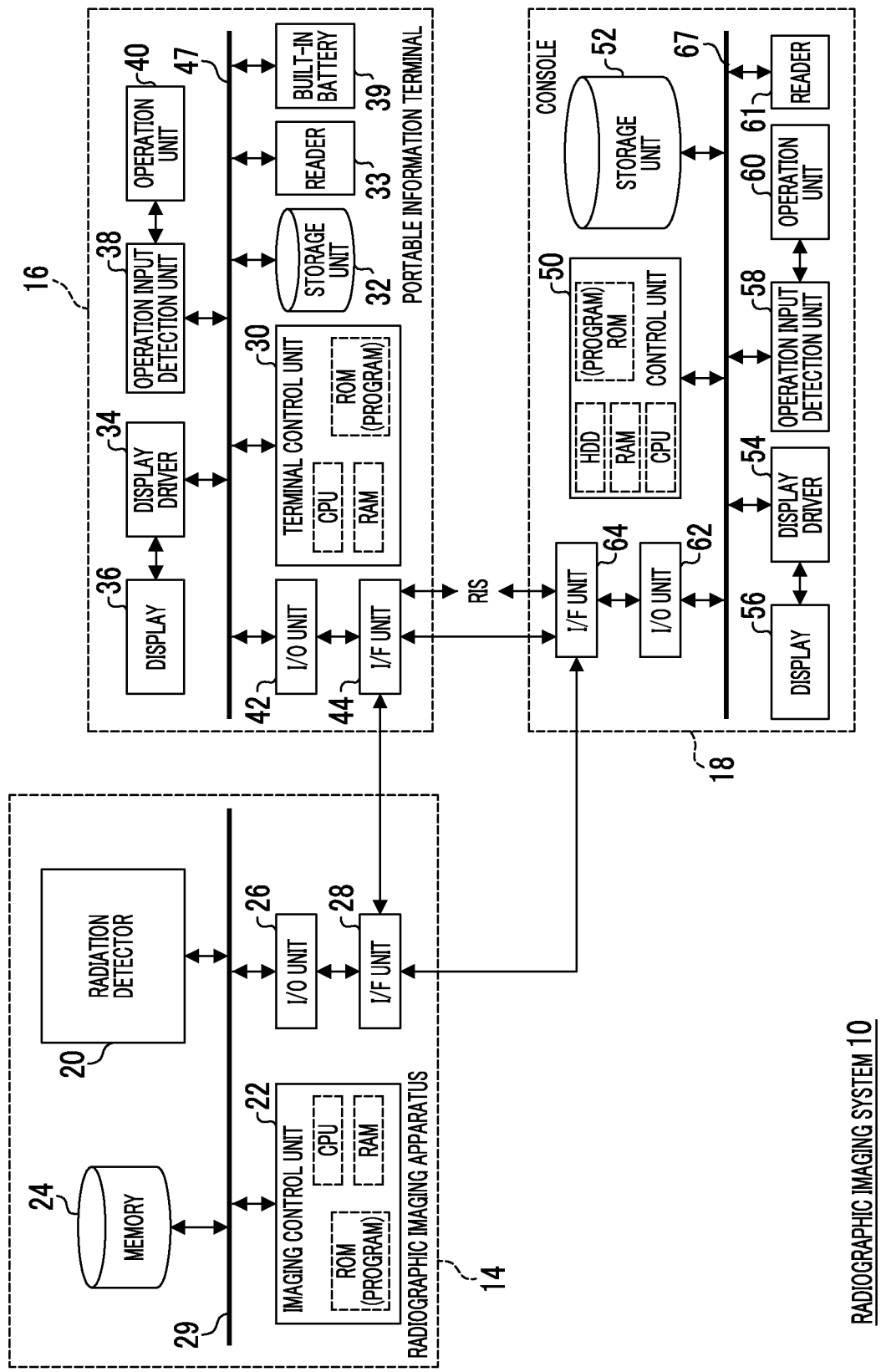
FIG. 2 is a block diagram illustrating an example of a schematic configuration of a radiographic imaging apparatus, a portable information terminal, and a console of the first embodiment.

Next, respective functions of the radiographic imaging apparatus 14, the portable information terminal 16, and the console 18 will be described in detail. FIG. 2 is a block diagram illustrating an example of schematic configurations of the radiographic imaging apparatus 14, the portable information terminal 16, and the console 18 of the radiographic imaging system 10.

The radiographic imaging apparatus 14 of this embodiment includes a radiation detector 20, an imaging control unit 22, a memory 24, an input/output (I/O) unit 26, and an interface (I/F) unit 28. The radiation detector 20, the imaging control unit 22, the memory 24, and the input/output (I/O) unit 26 are connected to each other through a bus 29 such as a system bus or a control bus to be able to exchange a variety of information.

The radiographic imaging apparatus 14 of this embodiment detects the start of irradiation of radiation R using the host device in an asynchronous manner with the radiation irradiator 12 to generate the radiographic image. In the radiographic imaging apparatus 14, a method for detecting the start of irradiation of the radiation R using the host device in an asynchronous manner with the radiation irradiator 12 is not particularly limited. For example, the radiographic imaging apparatus 14 may include a detection unit that detects a radiation dose of the irradiated radiation R, and may detect, when the irradiation dose detected by the detection unit exceeds a predetermined threshold value as an irradiation start, that the irradiation has started. The radiographic imaging apparatus 14 is not limited to this embodiment, and may be any device having a function of generating the radiographic image depending on the radiation R that passes through the subject W.

The radiation detector 20 includes a function of detecting the radiation R that passes through the subject W under the control of the imaging control unit 22. The radiation detector 20 of this embodiment is not particularly limited. For example, the radiation detector 20 may be a radiation detector of an indirect conversion type that converts radiation R into light and converts the converted light into electric charges, or may be a radiation detector of a direct conversion type that directly converts radiation R into electric charges.

The imaging control unit 22 includes a function of controlling an overall operation of the radiographic imaging apparatus 14.

The imaging control unit 22 includes a central processing unit (CPU), a read-only memory (ROM), and a random access memory (RAM). The ROM stores various process programs executed by the CPU, or the like. The RAM has a function of temporarily storing a variety of data.

The memory 24 stores image data of a radiographic image obtained by imaging, or the like. As a specific example of the memory 24, a solid state drive (SSD) or the like may be used. The memory 24 may be integrated with the radiographic imaging apparatus 14 when performing the imaging of the radiographic image, and for example, may be a memory capable of being detachably mounted on the radiographic imaging apparatus 14, such as a universal serial bus (USB) memory or a secure digital (SD) memory card (registered trademark).

The I/F unit 28 is connected to the I/O unit 26, and has a function of performing communication of a variety of information with the portable information terminal 16 or the console 18 through wireless communication or the like using a radio wave or light. The radiographic imaging apparatus 14 of this embodiment uses short-range wireless communication when performing communication with the portable information terminal 16, and uses wireless local area network (LAN) communication when performing communication with the console 18. Specifically, the radiographic imaging apparatus 14 uses Bluetooth (registered trademark) when performing communication with the portable information terminal 16, and uses Wireless-Fidelity (Wi-Fi) when performing communication with the console 18.

The portable information terminal 16 of this embodiment includes a terminal control unit 30, a storage unit 32, a reader 33, a display driver 34, a display 36, an operation input detection unit 38, an operation unit 40, an I/O unit 42, and an I/F unit 44. The terminal control unit 30, the storage unit 32, the reader 33, the display driver 34, the operation input detection unit 38, and the I/O unit 42 are connected to each other through a bus 47 such as a system bus or a control bus to be able to exchange a variety of information.

The terminal control unit 30 has a function of controlling an overall operation of the portable information terminal 16. Further, the terminal control unit 30 has a function of acquiring order information through the I/F unit 44 through the console 18 or an external system.

The terminal control unit 30 includes a CPU, a ROM, and a RAM. The ROM stores in advance various process programs including a terminal process program (which will be described later) executed by the CPU, or the like. The RAM has a function of temporarily storing a variety of data.

The reader 33 of this embodiment has a function of reading a character, an image, or the like. Specifically, the reader 33 has a camera function, and functions as a barcode reader.

The display 36 of this embodiment is an example of a display unit of the invention, and has a function of displaying a variety of information relating to imaging or a preview image of a radiographic image obtained by imaging. The display driver 34 has a function of controlling display of the variety of information on the display 36. The display 36 of this embodiment has a display capability lower than that of a display 56 of the console 18. The display capability in this embodiment means the size of a display region, a resolution, and a gradation, and the like. The display 36 is an example of a "display unit with a relatively low display capability" of the invention. In this embodiment, the "relatively low display capability" may be based on an evaluation result obtained by collectively evaluating a plurality of display capabilities, may be obtained by collectively evaluating a plurality of display capabilities with weights given thereto, or may be based on an evaluation result obtained by evaluating a predetermined display capability among a plurality of display capabilities.

Specifically, the display 36 has a small display region (screen size). More specifically, the size of the display 36 is "model 10" (the length of a diagonal corresponds to 25 cm) or smaller. Further, the display 36 of this embodiment has a low resolution and a small gradation compared with the display 56 of the console 18. In addition, the image processing function of the portable information terminal 16 of this embodiment is inferior to that of the console 18. Thus, a radiographic image which is image-processed by the terminal control unit 30 has an image quality lower than that of a radiographic image which is image-processed by a control unit 50 of the console 18. Accordingly, the display 36 of the portable information terminal 16 is not suitable for display of a radiographic image for image reading. Although the image processing function of the portable information terminal 16 is the same as that of the console, since the display capability of the display 36 is lower, the image quality of an image capable of being displayed on the display 36 is lower than the image quality of an image capable of being displayed on the display 56 of the console 18.

The operation unit 40 is used when a user inputs an instruction relating to image reading of a radiographic image, a variety of information, or the like. The operation unit 40 of this embodiment may include, for example, a touch panel, a touch pen, a keyboard, a mouse, or the like. In this embodiment, the display 36 and the operation unit 40 are integrated to form a touch panel display. The operation input detection unit 38 has a function of detecting an operation state with respect to the operation unit 40.

The I/O unit 42 and the I/F unit 44 have a function of performing communication of a variety of information with the radiographic imaging apparatus 14 or the console 18 through wireless communication using radio waves or light, or the like. The portable information terminal 16 of this embodiment uses short-range wireless communication when performing communication with the radiographic imaging apparatus 14, and uses wireless LAN communication when performing communication with the console 18. Specifically, the portable information terminal 16 uses Bluetooth (registered trademark) when performing communication with the radiographic imaging apparatus 14, and uses Wi-Fi when performing communication with the console 18.

The storage unit 32 stores the above-mentioned order information or the like. Further, information for performing display of various screens or the like (details of which will be described later) is stored in advance in the storage unit 32 of this embodiment. As a specific example of the storage unit 32, an SSD or the like may be used. It is sufficient if the storage unit 32 can be integrated with the portable information terminal 16 when performing imaging of a radiographic image, and for example, a memory capable of being detachably mounted to the portable information terminal 16, such as a USB memory or an SD memory card, may be used.

The console 18 of this embodiment functions as a server computer. The console 18 includes a control unit 50, a storage unit 52, a display driver 54, a display 56, an operation input detection unit 58, an operation unit 60, a reader 61, an I/O unit 62, and an I/F unit 64. The control unit 50, the storage unit 52, the display driver 54, the operation input detection unit 58, the reader 61, and the I/O unit 62 are connected to each other through a bus 67 such as a system bus or a control bus to be able to exchange a variety of information.

The control unit 50 has a function of controlling an overall operation of the console 18, and includes a CPU, a ROM, a RAM, and a hard disk drive (HDD). The ROM stores in advance various process programs including a console process program executed by the CPU, or the like. The RAM has a function of temporarily storing a variety of data. The HDD has a function of storing and retaining a variety of data.

The display 56 of this embodiment is an example of a display unit of the invention, and has a function of displaying a variety of information relating to imaging, a radiographic image for image reading, or the like. The display driver 54 has a function of controlling display of a variety of information on the display 56. The display 56 of this embodiment has a display region size (screen size) larger than that of the display 36 of the portable information terminal 16. Further, the display 56 of this embodiment has a high resolution and a large gradation compared with the display 36 of the portable information terminal 16.

In the radiographic imaging system 10 of this embodiment, in a case where a user performs reading (including medical examination and diagnosis) of a radiographic image, the user uses the console 18, or a reader (not shown) such as a viewer which is separately provided, for example. Thus, the image processing function of the console 18 is used to generate a high-quality radiographic image with which an user can perform image reading, and thus, is superior to that of the portable information terminal 16. A radiographic image which is image-processed by the control unit 50 has a quality higher than that of a radiographic image which is image-processed by the terminal control unit 30 of the portable information terminal 16. Accordingly, the display 56 of the console 18 is suitable for display of a radiographic image for image reading.

The operation unit 60 is used when a user inputs information relating to imaging of a radiographic image, or the like. The operation unit 60 of this embodiment includes a touch panel, a touch pen, a keyboard, a mouse, or the like, for example. When the operation unit 60 includes a touch panel, the operation unit 60 may be integrated with the display 56. The operation input detection unit 58 has a function of detecting an operation state with respect to the operation unit 60.

The reader 61 of the embodiment has a function of reading a character, an image or the like, similar to the reader 33 in the portable information terminal 16. Specifically, the reader 61 has a camera function, and functions as a barcode reader, for example.

In this embodiment, by reading information for recognizing a subject W using the reader 33 of the portable information terminal 16 or the reader 61 of the console 18, subject authentication is performed. A subject authentication method is not particularly limited. For example, in the case of a barcode reader as a specific example, the barcode reader may read, as identification information, a character or a barcode from a wristband in which identification information such as a patient name is written with a character, a barcode or the like, worn by a patient for preventing patient identification errors, and the read information may be used for subject authentication. Further, a photo of the face of the subject W may be registered in advance, and a photo of the subject W obtained by imaging in the reader 33 or the reader 61 may be compared with the registered photo of the face. Further, other biological information (for example, fingerprints or irises, or the like) on the subject W may be registered in advance, so that the reader 33 or the reader 61 can perform biological authentication.

The I/O unit 62 and the I/F unit 64 have a function of performing communication of a variety of information with the radiographic imaging apparatus 14 or the portable information terminal 16 through wireless communication using radio waves or light, or the like. The console 18 of this embodiment uses wireless LAN communication when performing communication with the radiographic imaging apparatus 14 and the portable information terminal 16. Specifically, the console 18 uses Wi-Fi when performing communication with the radiographic imaging apparatus 14 and the portable information terminal 16.

The storage unit 52 stores the above-described order information or the like, and image data of a radiographic image. Further, the storage unit 52 of this embodiment stores in advance information for performing display of a variety of screens (which will be described later in detail) or the like. As a specific example of the storage unit 52, an HDD, an SSD, or the like may be used.

In the radiographic imaging system 10 of this embodiment, the terminal control unit 30 of the portable information terminal 16 and the control unit 50 of the console 18 function as a setting unit, a control unit, a display content reception unit, and a control content reception unit of the invention.

Next, an operation of the radiographic imaging system 10 of this embodiment in a case where a radiographic image is captured will be described.

Figure 3:
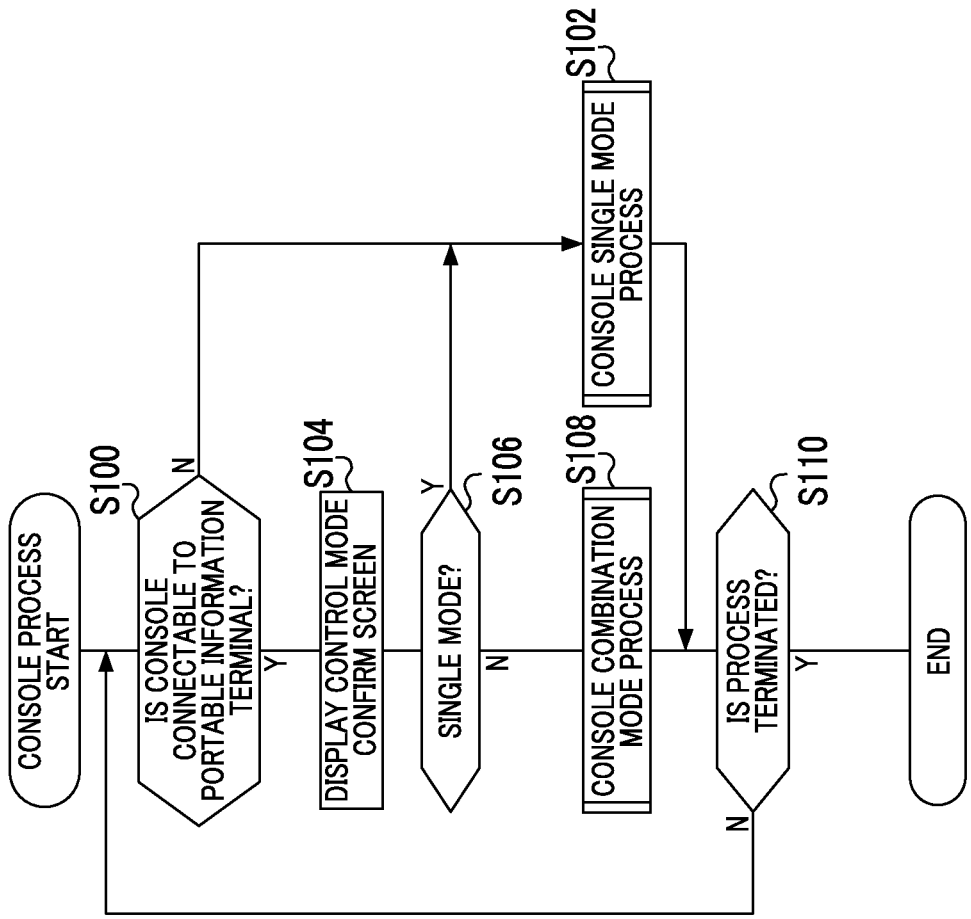
FIG. 3 is a flowchart illustrating an example of a flow of a console process executed by a control unit of a console of the first embodiment.

First, an operation of the console 18 will be described. FIG. 3 shows a flowchart illustrating an example of a flow of a console process executed by the control unit 50 of the console 18 in this embodiment. In the console 18 of this embodiment, the control unit 50 executes a console process program stored in a ROM thereof to execute the console process.

In the following description, in a case where a user performs a variety of designations or selections on a variety of screens (which will be described later) displayed on the display 56, the user performs the designations or selections through the operation unit 60.

The present console process is executed in a case where an instruction for performing imaging of a radiographic image is input through the operation unit 60, and in a case where a connection confirmation signal (which will be described later in detail) is received from the portable information terminal 16, for example.

The control unit 50 in step S100 in FIG. 3 determines whether the console 18 is connectable to the portable information terminal 16. As described above, in the radiographic imaging system 10 of this embodiment, since in a case where communication between the portable information terminal 16 and the console 18 is possible, the combination mode can be used, it is determined whether the console 18 is connected to the portable information terminal 16. Here, the "connection" means a connection through communication, and does not limit to direct and physical connection.

In a case where transmission or reception of a predetermined connection confirmation signal is possible with respect to the portable information terminal 16 through the I/F unit 64, the control unit 50 determines that the connection is possible. Further, in a case where a connection confirmation signal is received from the portable information terminal 16 in a manual manner only, the control unit 50 similarly determines that the connection is possible.

In a case where the connection between the portable information terminal 16 and the console 18 is not possible, the determination in step S100 is negative, and then, the procedure proceeds to step S102. In step S102, the control unit 50 executes the console single mode process (which will be described later in detail), and then, the procedure proceeds to step S110.

On the other hand, in a case where the connection between the portable information terminal 16 and the console 18 is possible, the determination in step S100 is affirmative, and then, the procedure proceeds to step S104. In this case, in the radiographic imaging system 10 of this embodiment, the control mode may be set to the combination mode. However, even in this case, a user may perform imaging in the console single mode.

Figure 4:
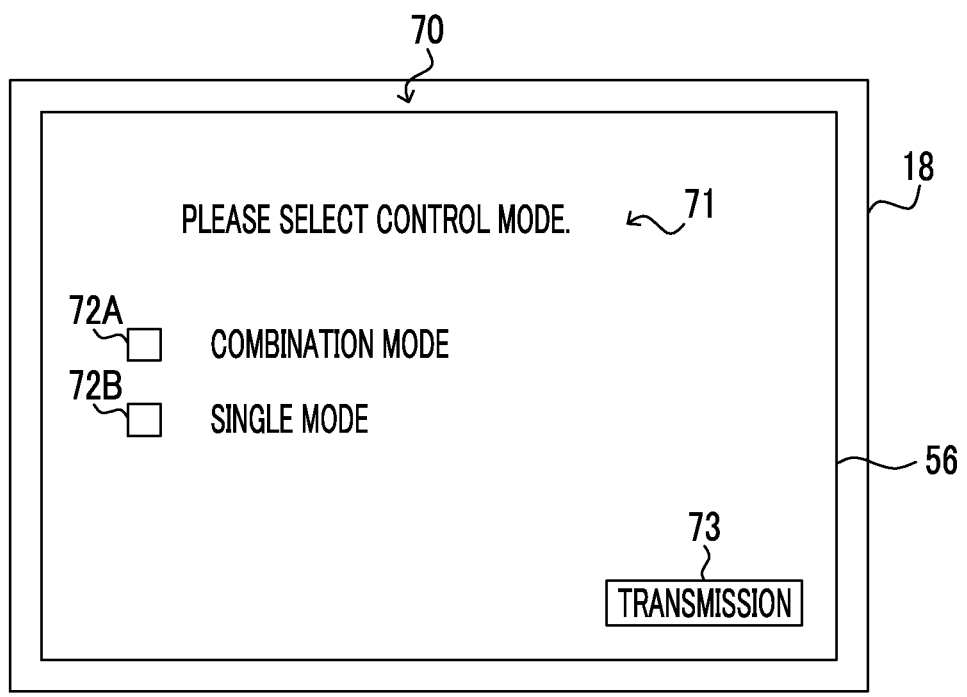
FIG. 4 is a schematic diagram showing a specific example of a state where a control mode confirmation screen is displayed on a display of a console.

Thus, in step S104, the control unit 50 displays a control mode confirmation screen on the display 56. FIG. 4 shows a schematic diagram illustrating a specific example in a state where a control mode confirmation screen 70 is displayed on the display 56 of the console 18. In this embodiment, display for causing a user to confirm whether to set the combination mode as the control mode is performed on the control mode confirmation screen 70.

On the control mode confirmation screen 70 in the specific example shown in FIG. 4, information 71, check boxes 72A and 72B, and a transmission button 73 for prompting a user to designate the setting of any one of the combination mode and the single mode are displayed as the control mode are displayed. In this case, the "single mode" is a single mode in which only the console 18 performs a control relating to imaging of a radiographic image.

A user designates any one of the check boxes 72A and 72B corresponding to the control mode to be set, and then, designates the transmission button 73. If the control unit 50 detects that the transmission button 73 is designated, the procedure proceeds to step S106.

In a case where the control unit 50 detects that the check box 72B is designated, the determination in step S106 is affirmative, and thus, the single mode is set as the control mode. Then, the procedure proceeds to step S102.

On the other hand, in a case where the control unit 50 detects that the check box 72A is designated, the determination in step S106 is negative, and thus, the combination mode is set as the control mode. Then, the procedure proceeds to step S108.

In step S108, the control unit 50 executes the console combination mode process (which will be described later in detail), and then, the procedure proceeds to step S110.

In step S110, the control unit 50 determines whether the console process is terminated. For example, in a case where a user does not instruct termination of imaging of a radiographic image, or in similar cases, the determination becomes negative, and then, the procedure returns to step S100, so that the console process is continued. On the other hand, in a case where the user instructs the termination of the imaging of the radiographic image, or in similar cases, when the determination is affirmative, the console process is terminated.

Next, the console single mode process of step S102 (see FIG. 3) of the console process, executed by the console 18 of this embodiment will be described.

Figure 5B:
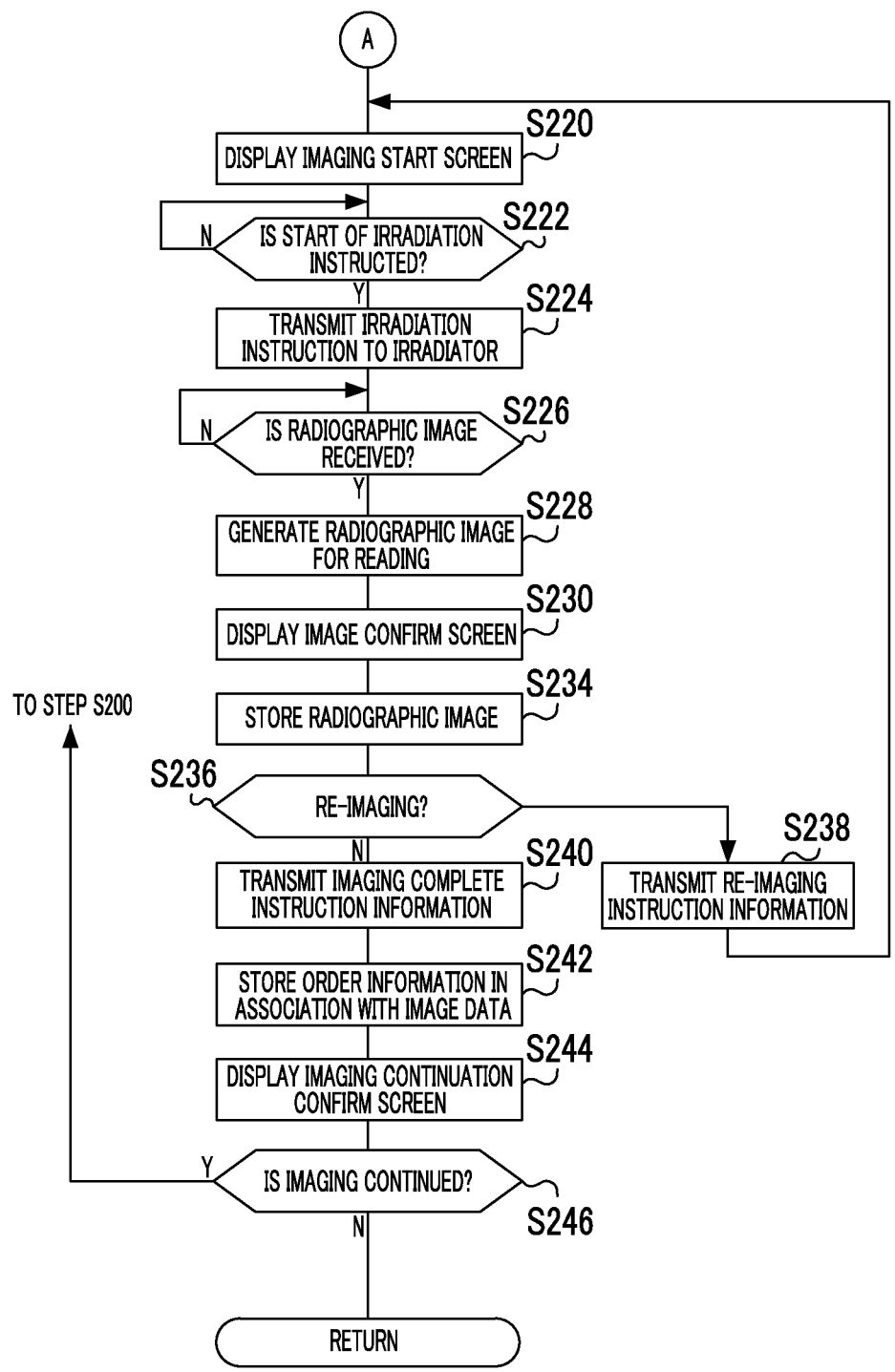
FIG. 5B is a flowchart illustrating an example of a flow of the console single mode process and the console combination mode process, subsequent to the flow of FIG. 5A.

FIGS. 5A and 5B show a flowchart illustrating an example of a flow of the console single mode process executed by the control unit 50 of the console 18 of this embodiment.

In step S200 of FIG. 5A, the control unit 50 causes the display 56 to display an initial imaging screen, i.e. the control unit 50 controls to display an initial imaging screen on the display 56. Specifically, the control unit 50 generates the initial imaging screen using information relating to the initial imaging screen stored in the storage unit 52, and causes the display 56 to display the generated initial imaging screen.

Figure 6:
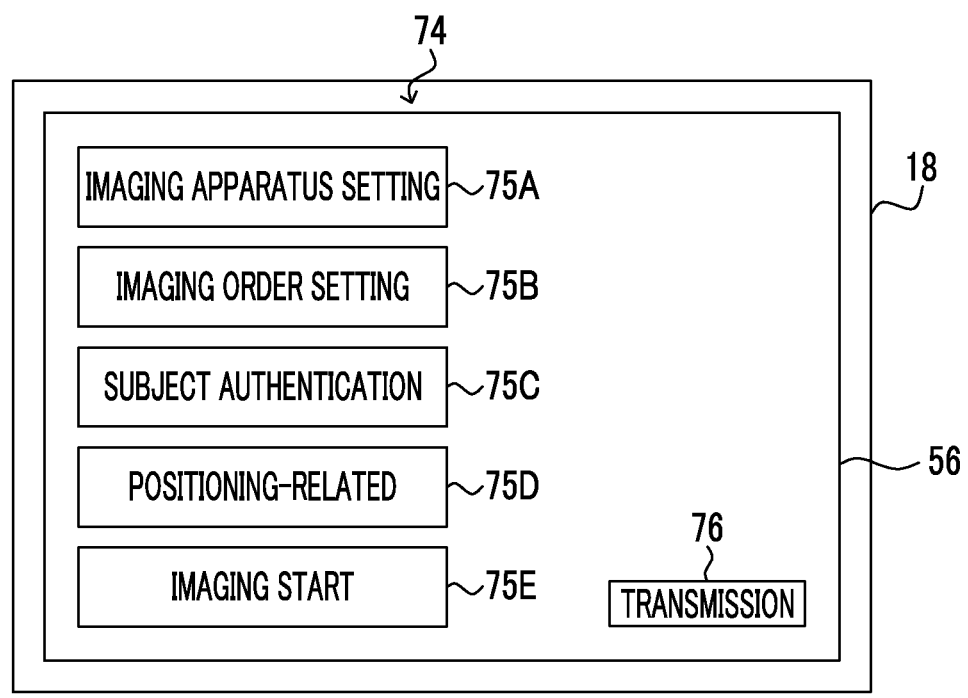
FIG. 6 is a schematic diagram showing a specific example in a state where an initial imaging screen is displayed on the display of the console.

FIG. 6 is a schematic diagram illustrating a specific example of a state where an initial imaging screen 74 is displayed on the display 56 of the console 18. On the initial imaging screen 74 of this embodiment, display for performing a setting or an instruction relating to imaging of a radiographic image by a user is performed. Thus, on the initial imaging screen 74 of the specific example shown in FIG. 6, select buttons 75A to 75E and a transmission button 76 are displayed. The select button 75A is a button that is selected by a user in a case where the radiographic imaging apparatus 14 is set. The select button 75B is a button that is selected by a user in a case where an imaging order is set. The select button 75C is a button that is selected by a user in a case where subject comparison is performed. The select button 75D is a button that is selected by a user in a case where positioning related display is performed. The select button 75E is a button that is selected by a user for the start of imaging of a radiographic image.

A user selects any one of the select buttons 75A to 75E, and then, designates the transmission button 76. If the control unit 50 detects that the transmission button 76 is designated, the procedure proceeds to step S202A.

In step S202A, the control unit 50 determines whether "imaging apparatus setting" is selected on the initial imaging screen 74. In a case where the control unit 50 detects that the select button 75A is selected by a user, the determination is affirmative, and then, the procedure proceeds to step S204.

Figure 7:
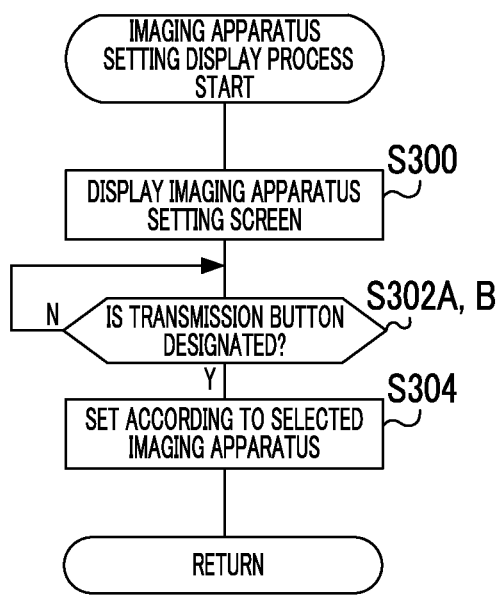
FIG. 7 is a flowchart showing an example of a flow of an imaging apparatus setting display process executed by the control unit of the console in the first embodiment.

In step S204, the control unit 50 executes an imaging apparatus setting display process shown in FIG. 7. FIG. 7 is a flowchart illustrating an example of a flow of an imaging apparatus setting display process executed by the control unit 50 of the console 18 of this embodiment.

In step S300 in FIG. 7, the control unit 50 causes the display 56 to display an imaging apparatus setting screen. Specifically, the control unit 50 generates the imaging apparatus setting screen using information relating to the imaging apparatus setting screen stored in the storage unit 52 and information relating to the radiographic imaging apparatus 14 provided in the radiographic imaging system 10, and causes the display 56 to display the generated information.

Figure 8:
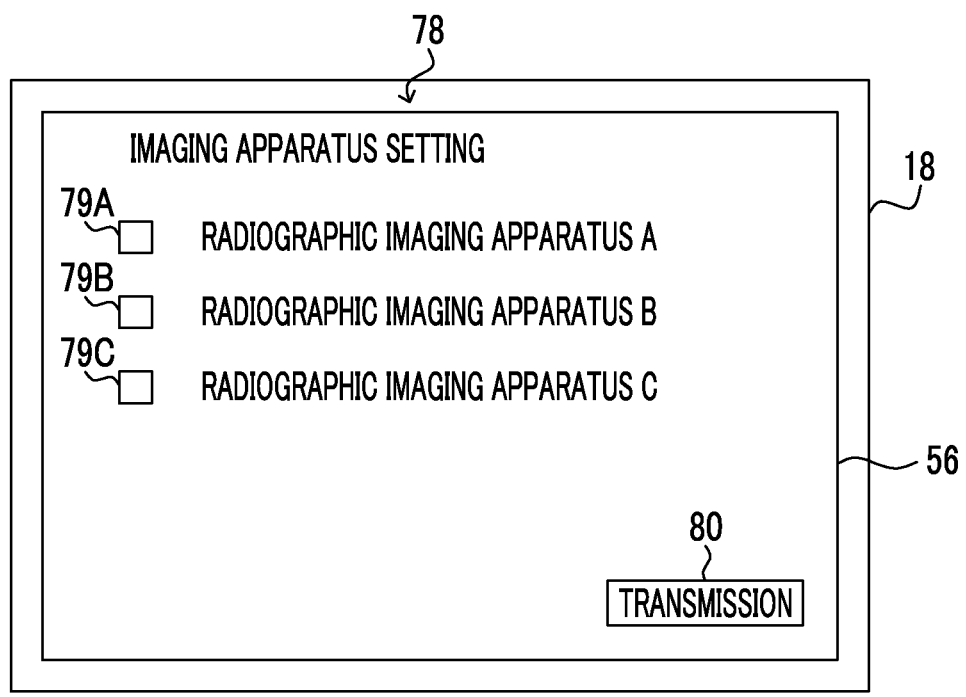
FIG. 8 is a schematic diagram showing a specific example of a state where an imaging apparatus setting screen is displayed on the display of the console.

FIG. 8 is a schematic diagram showing a specific example of a state where an imaging apparatus setting screen 78 is displayed on the display 56 of the console 18. On the imaging apparatus setting screen 78 of the embodiment, a display for setting the radiographic imaging apparatus 14 by a user is performed. As described above, the radiographic imaging system 10 may include a plurality of radiographic imaging apparatuses 14. In such a case, a user may select one radiographic imaging apparatus 14 used for imaging a radiographic image among the plurality of radiographic imaging apparatuses 14, from the console 18. As a specific example, in a case where the radiographic imaging system 10 includes three radiographic imaging apparatuses 14, check boxes 79A to 79C and a transmission button 80 corresponding to each of three radiographic imaging apparatuses 14 are displayed on the imaging apparatus setting screen 78 shown in FIG. 8.

The check boxes 79A to 79C are used when a user selects the radiographic imaging apparatus 14 used for imaging a radiographic image. The user designates any one of the check boxes 79A to 79C corresponding to the radiographic imaging apparatus 14 to be used for imaging of a radiographic image, and then, designates the transmission button 80.

Thus, in the next step S302A, the control unit 50 determines whether the transmission button 80 is designated, waits until it has been detected that the transmission button 80 is designated. If it is detected that the transmission button 80 is designated, the determination is affirmative, and then, the procedure proceeds to step S304.

In step S304, the control unit 50 detects a check box designated by a user from the check boxes 79A to 79C, performs a setting based on the radiographic imaging apparatus 14 corresponding to the detected check box, and then, terminates the imaging apparatus setting display process.

If the imaging apparatus setting display process is terminated in this way, the procedure returns to step S200 of the console single mode process, and the control unit 50 causes the display 56 to display the initial imaging screen 74 again.

On the other hand, in a case where the user selects a button other than the select button 75A on the initial imaging screen 74 displayed on the display 56, the determination is negative in step S202A, and then, the procedure proceeds to step S206A.

In step S206A, the control unit 50 determines whether the "imaging order setting" is selected on the initial imaging screen 74. In a case where the control unit 50 detects that the select button 75B is selected by the user, the determination is affirmative, and then, the procedure proceeds to step S208.

Figure 9:
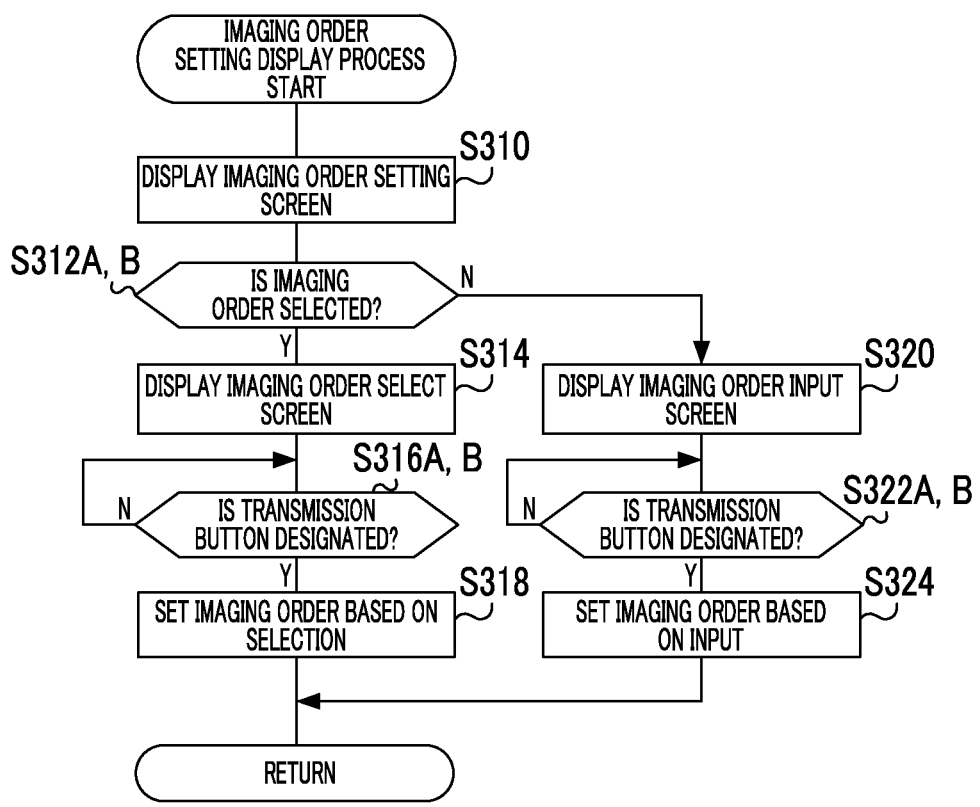
FIG. 9 is a flowchart showing an example of a flow of an imaging order setting display process executed by the control unit of the console of the first embodiment.

In step S208, the control unit 50 executes an imaging order setting display process shown in FIG. 9. FIG. 9 is a flowchart showing an example of a flow of an imaging order setting display process executed by the control unit 50 of the console 18 of this embodiment.

In step S310 in FIG. 9, the control unit 50 causes the display 56 to display an imaging order setting screen. Specifically, the control unit 50 generates the imaging order setting screen using information relating to the imaging order setting screen stored in the storage unit 52, and causes the display 56 to display the generated screen.

Figure 10:
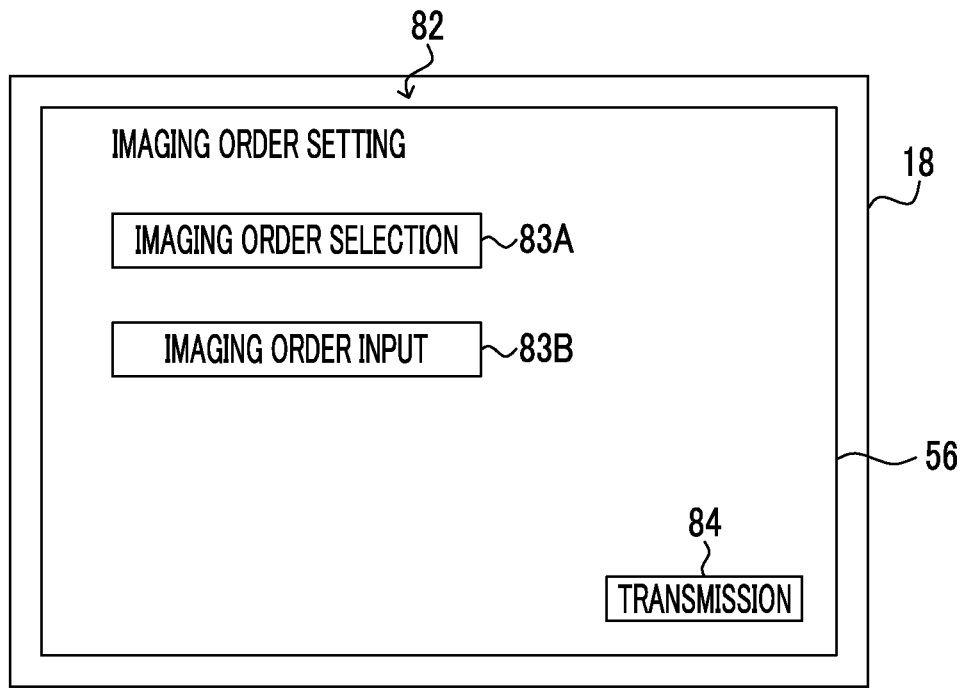
FIG. 10 is a schematic diagram showing a specific example of a state where an imaging order setting screen is displayed on the display of the console.

FIG. 10 is a schematic diagram showing a specific example of a state where an imaging order setting screen 82 is displayed on the display 56 of the console 18. On the imaging order setting screen 82 of the embodiment, a display is displayed for selecting by a user whether to select an imaging order used for imaging from existing imaging orders or to input a new imaging order. Select buttons 83A and 83B, and a transmission button 84 are displayed on the imaging order setting screen 82 in the specific example shown in FIG. 10.

In a case where an imaging order used for imaging is selected from the existing imaging orders stored in the storage unit 52, a user selects the select button 83A, and then, designates the transmission button 84. Thus, in a case where it is detected that the transmission button 84 is designated, the procedure proceeds to step S312A.

In step S312A, the control unit 50 determines whether to perform selection of an imaging order. In a case where the control unit 50 detects that the select button 83A is selected by the user, the determination is affirmative, and then, the procedure proceeds to step S314.

In step S314, the control unit 50 causes the display 56 to display an imaging order select screen. Specifically, the control unit 50 generates the imaging order select screen using the information relating to the imaging order select screen stored in the storage unit 52 and the order information regarding the imaging order stored in the storage unit 52, and causes the display 56 to display the generated information.

Figure 11:
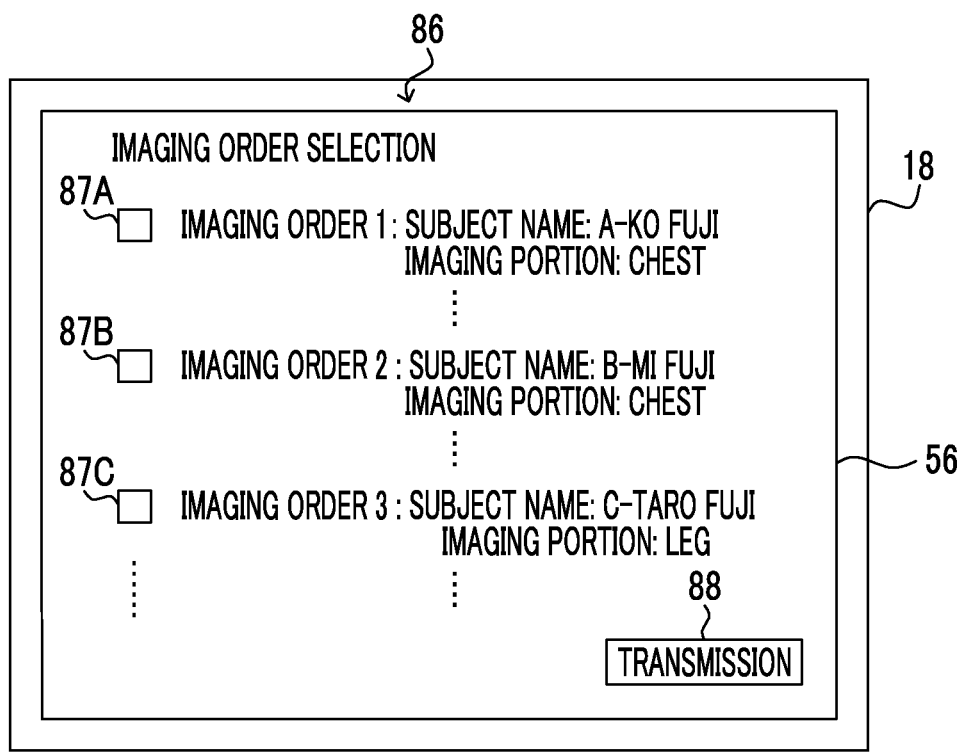
FIG. 11 is a schematic diagram showing a specific example of a state where an imaging order select screen is displayed on the display of the console.

FIG. 11 is a schematic diagram showing a specific example of a state where an imaging order select screen 86 is displayed on the display 56 of the console 18. Check boxes 87A to 87C corresponding to the respective imaging orders 1 to 3, and a transmission button 88 are displayed on the imaging order select screen 86 of the specific example shown in FIG. 11. Further, order information corresponding to each imaging order is also displayed on the imaging order select screen 86 of this embodiment to support selection of the imaging order.

The check boxes 87A to 87C are used when a user selects an imaging order. In a case where there is order information regarding an imaging order for which imaging is completely terminated, display in a state where the corresponding check box is checked is performed.

A user designates any one of the check boxes 87A to 87C corresponding to an imaging order used for imaging, and then, designates the transmission button 88.

Thus, in the next step S316A, the control unit 50 waits until it is detected that the transmission button 88 has been designated. If it is detected that the transmission button 88 is designated, the determination is affirmative, and then, the procedure proceeds to step S318.

In step S318, the control unit 50 detects a check box designated by a user from the check boxes 87A to 87C, acquires an imaging order corresponding to the detected check box from the storage unit 52, sets the acquired imaging order as an imaging order used for imaging, and then, terminates the imaging order setting display process. Thus, thereafter, imaging of a radiographic image is performed on the basis of the set imaging order.

On the other hand, in step S312A, in a case where the control unit 50 detects that the select button 83B is selected by a user, the determination is negative, and then, the procedure proceeds to step S320.

Generally, in a case where imaging of a radiographic image is performed, there is a case where a necessity for additional imaging (hereinafter, referred to as "additional imaging") occurs, in addition to imaging orders of order information stored in the storage unit 52 in advance. In the case of performing the additional imaging, in a case where it is possible to acquire order information regarding an imaging order based on the additional imaging from an external system or the like, the order information may be acquired and stored in the storage unit 52. The imaging order in this case may be selected from the above-described imaging order select screen 86 as an existing imaging order.

However, since there is a case where the order information regarding the imaging order based on the additional imaging cannot be acquired, in step S320, the control unit 50 causes the display 56 to display an imaging order input screen. Specifically, the control unit 50 generates the imaging order input screen using information relating to the imaging order input screen stored in the storage unit 52, and causes the display 56 to display the generated screen.

Figure 12:
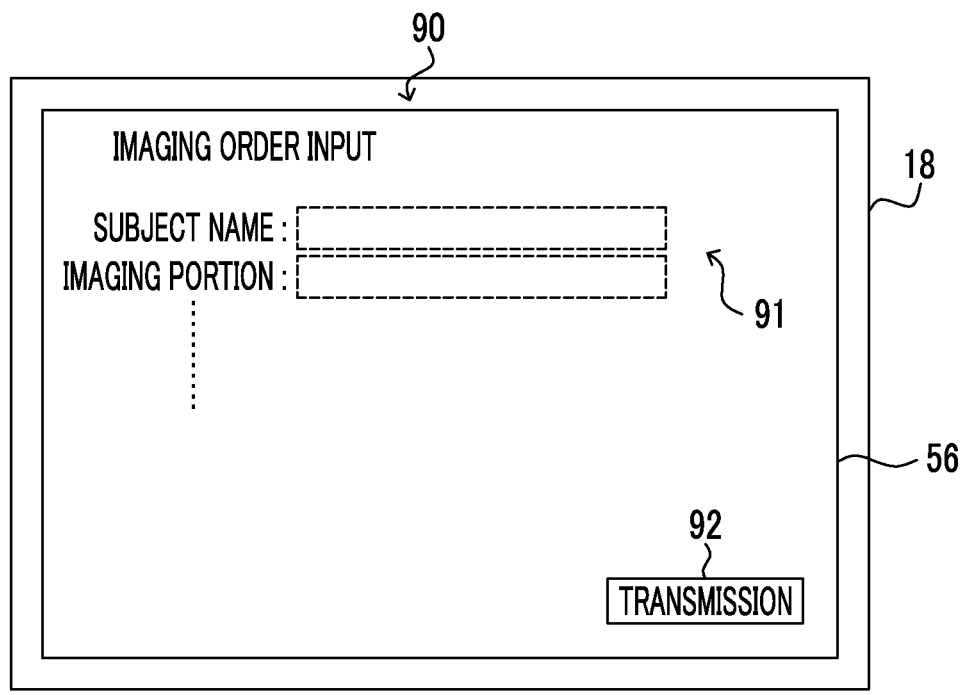
FIG. 12 is a schematic diagram showing a specific example of a state where an imaging order input screen is displayed on the display of the console.

FIG. 12 is a schematic diagram showing a specific example of a state where an imaging order input screen 90 is displayed on the display 56 of the console 18. Information 91 for prompting a user to input an imaging order and a transmission button 92 are displayed on the imaging order input screen 90 of the specific example shown in FIG. 12.

The user inputs an imaging order on the basis of the information 91. If the inputting is finished, the user designates the transmission button 92. The imaging order input by the user may include information necessary for imaging of a radiographic image, such as order information such as a subject name or an imaging portion, and may be different from a normal imaging order, an imaging order acquired from an external system or the like.

Thus, in the next step S322A, the control unit 50 waits until it has been detected that the transmission button 92 is designated. If it is detected that the transmission button 92 is designated, the determination is affirmative, and then, the procedure proceeds to step S324.

In step S324, the control unit 50 detects the imaging order input by the user, sets the detected imaging order as an imaging order used for imaging, and then, terminates the imaging order setting display process. Thus, thereafter, imaging of a radiographic image is performed on the basis of the set imaging order.

If the imaging order setting display process is terminated in this way, the procedure returns to step S200 of the console single mode process, and then, the control unit 50 causes the display 56 to display the initial imaging screen 74 again.

On the other hand, on the initial imaging screen 74 displayed on the display 56, in a case where the user selects a button other than the select button 75B, the determination is negative in step S206A, and then, the procedure proceeds to step S210A.

In step S210A, the control unit 50 determines whether "subject authentication" is selected on the initial imaging screen 74. In a case where the control unit 50 detects that the select button 75C is selected by the user, the determination is affirmative, and then, the procedure proceeds to step S212.

Figure 13:
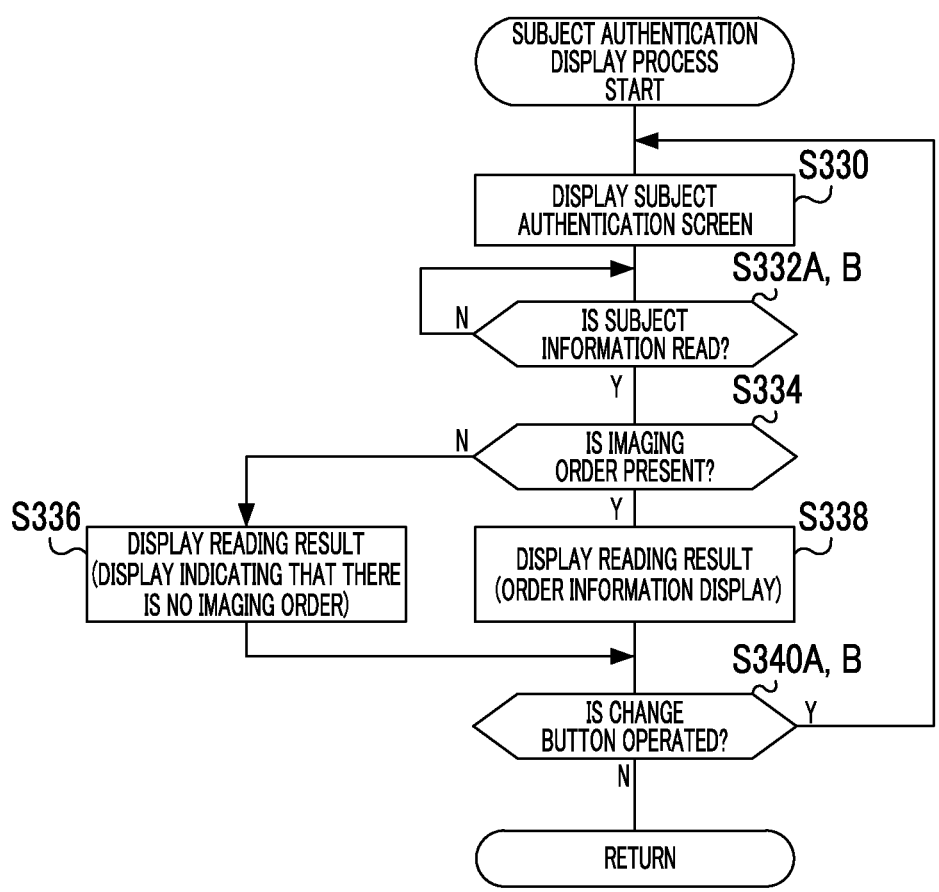
FIG. 13 is a flowchart illustrating an example of a flow of a subject authentication display process executed by the control unit of the console of the first embodiment.

In step S212, the control unit 50 executes a subject authentication display process shown in FIG. 13. FIG. 13 is a flowchart illustrating an example of a flow of a subject authentication display process executed by the control unit 50 of the console 18 of this embodiment.

In step S330 in FIG. 13, the control unit 50 causes the display 56 to display a subject authentication screen. Specifically, the control unit 50 generates the subject authentication screen using information relating to the subject authentication screen stored in the storage unit 52, and causes the display 56 to display the generated screen.

Figure 14:
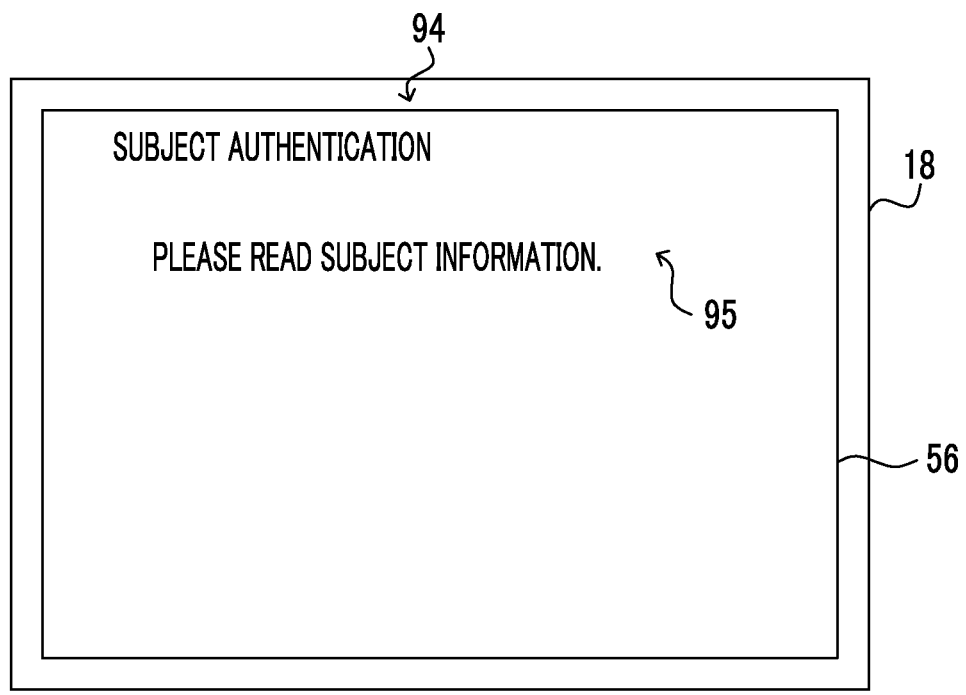
FIG. 14 is a schematic diagram illustrating a specific example of a state where a subject authentication screen is displayed on the display of the console.

FIG. 14 is a schematic diagram illustrating a specific example of a state where a subject authentication screen 94 is displayed on the display 56 of the console 18. Display of information for prompting a user to read the subject information is performed on the subject authentication screen 94 of this embodiment. Information 95 for prompting the user to read the subject information is displayed on the subject authentication screen 94 of the specific example shown in FIG. 14.

In order to perform subject authentication, the user reads by using the reader 61 a subject name written on a name card of a subject W, a medical record or the like, or two-dimensional codes such as a barcode or a QR code (registered trademark).

Thus, in the next step S332A, the control unit 50 determines whether subject information is read using the reader 61. The determination is negative until the subject information is read. On the other hand, in a case where the subject information is read, the determination is affirmative, and then, the procedure proceeds to step S334.

In step S334, the control unit 50 determines whether an imaging order corresponding to the read subject information is present. Specifically, the control unit 50 determines whether an imaging order included in the read subject information is present in the imaging orders stored in the storage unit 52. Further, in a case where the imaging order set by the user in the imaging order setting display process is present as described above, the control unit 50 determines whether the read subject information is included in the imaging order set by the user. In a case of where the read subject information is included in the imaging order set by the user, it is determined that the imaging order is present. On the other hand, in a case where the read subject information is not included in the imaging order set by the user, it is determined that there is no imaging order.

In a case where there is no imaging order corresponding to the read subject information, the determination is negative, and then, the procedure proceeds to step S336.

Figure 15:
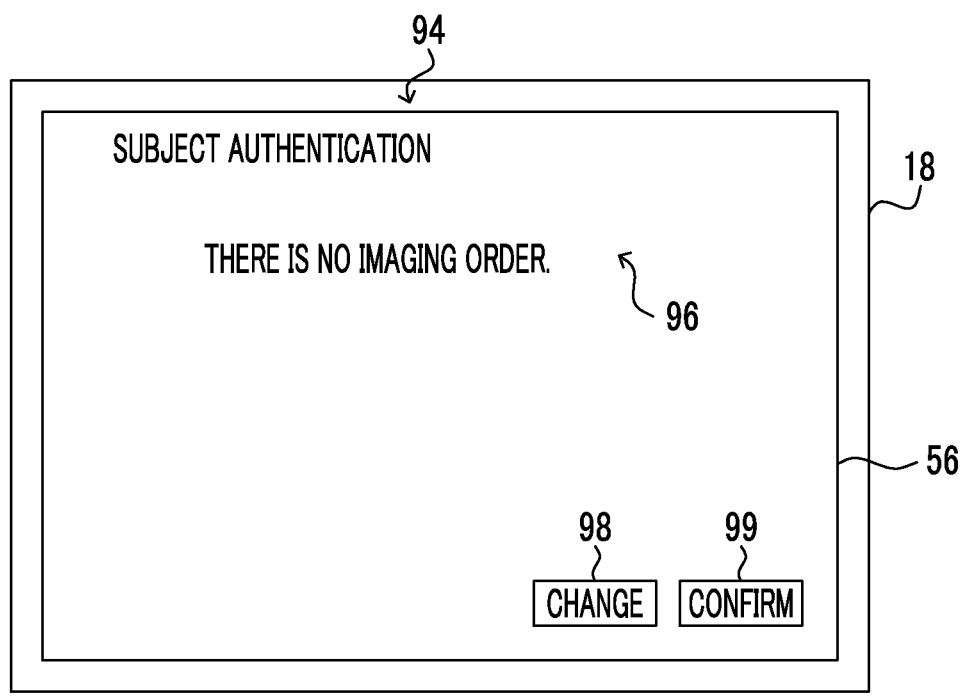
FIG. 15 is a schematic diagram illustrating a specific example of a state where a reading result is displayed on the subject authentication screen.

In step S336, the control unit 50 displays a reading result indicating that there is no imaging order on the subject authentication screen 94, and then, the procedure proceeds to step S340A. FIG. 15 is a schematic diagram illustrating a specific example of a state where a reading result is displayed on the subject authentication screen 94. Information 96 indicating that there is no imaging order, a change button 98, and a confirmation button 99 are displayed on the subject authentication screen 94 of the specific example shown in FIG. 15.

In the radiographic imaging system 10 of this embodiment, a case where there is no imaging order corresponding to the subject information read by the console 18 includes a case where an imaging order is not yet set, or a case where a subject W corresponding to the read subject information is a subject W for which imaging is not scheduled, for example.

According to the information 96 displayed on the subject authentication screen 94 of the display 56, the user confirms that there is no imaging order of the subject W. Further, in a case where the user wants to change the subject W, the user designates the change button 98. In addition, for example, in a case where the user wants to set an imaging order, the user designates the confirmation button 99.

On the other hand, in step S334, in a case where there is an imaging order corresponding to the read subject information, the determination is affirmative, and then, the procedure proceeds to step S338.

Figure 16:
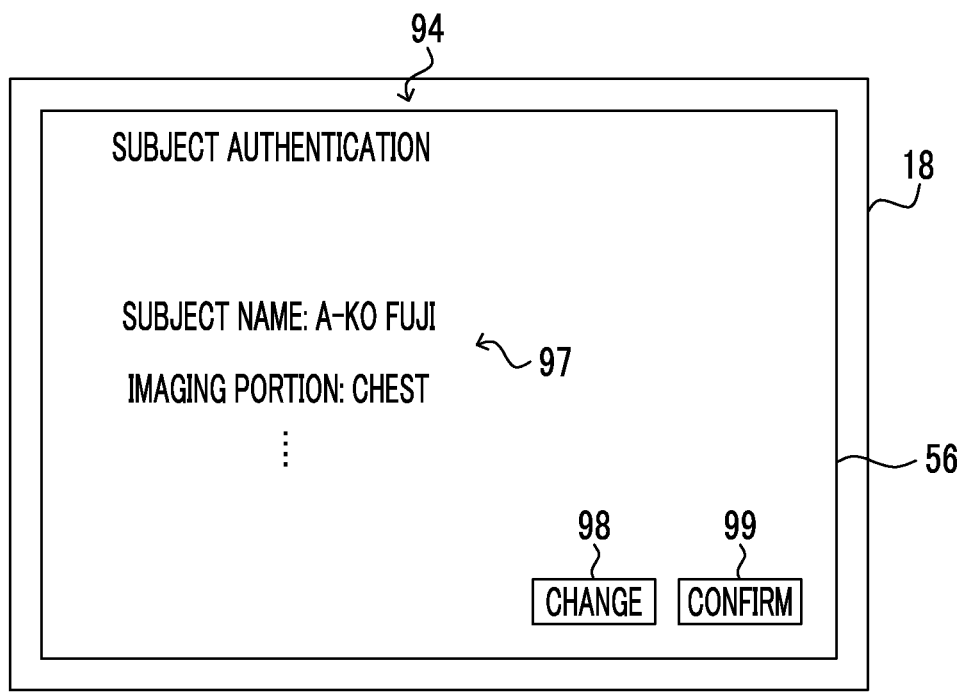
FIG. 16 is a schematic diagram illustrating a specific example of a state where a reading result is displayed on the subject authentication screen.

In step S338, the control unit 50 displays order information regarding the imaging order on the subject authentication screen 94 as a reading result, and then, the procedure proceeds to step S340A. FIG. 16 is a schematic diagram illustrating a specific example of a state where a reading result is displayed on the subject authentication screen 94. Order information 97 about an imaging order, a change button 98, and a confirmation button 99 are displayed on the subject authentication screen 94 of the specific example shown in FIG. 16.

According to the order information 97 displayed on the subject authentication screen 94 of the display 56, a user confirms order information regarding an imaging order of a subject W. Further, in a case where the user wants to change the subject W, the user designates the change button 98. In addition, for example, in a case where the user wants to set the imaging order, the user designates the confirmation button 99.

In the next step S340A, the control unit 50 determines whether the change button 98 is designated. Specifically, in a case where the control unit 50 detects that the change button 98 is designated, the determination is affirmative, and then, the procedure returns to step S330 to repeat the subject authentication display process. On the other hand, in a case where the control unit 50 detects that the confirmation button 99 is designated, the determination is negative, and then, the subject authentication display process is terminated.

In the console 18 of this embodiment, the imaging order confirmed by the user in the subject authentication display process is set as an imaging order used for imaging. Thus, even in a case where the user does not set the imaging order in the imaging order setting display process, it is possible to appropriately perform imaging of a radiographic image of a subject W on the basis of the imaging order set in the subject authentication display process.

In this way, the portable information terminal 16 of this embodiment performs authentication of the subject W, to thereby make it possible to prevent a radiographic image of a subject W for which imaging is not scheduled from being captured.

A subject authentication method is not limited to the above-described method. For example, in a case where a photo image including the face of a subject W is included in the order information, the control unit 50 may take a photograph of the face of the subject W using the reader 61, and may perform face authentication or the like using the captured image of the face to perform authentication of the subject W. In addition, for example, fingerprint authentication or the like may be used.

In this way, if the subject authentication display process is terminated, the procedure returns to step S200 of the console single mode process. Then, the control unit 50 causes the display 56 to display the initial imaging screen 74 again.

On the other hand, in a case where the user selects a button other than the select button 75C on the initial imaging screen 74 displayed on the display 56, the determination is negative in step S210A, and then, the procedure proceeds to step S214A.

In step S214A, the control unit 50 determines whether the "positioning related" is selected on the initial imaging screen 74. In a case where the control unit 50 detects that the select button 75D is selected by the user, the determination is affirmative, and then, the procedure proceed to step S216.

Figure 17:
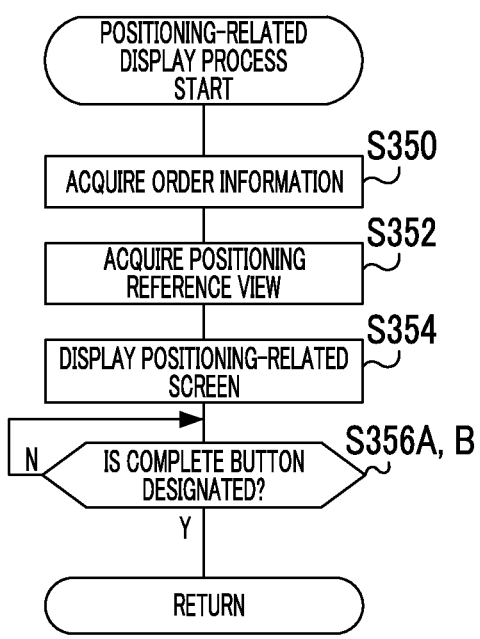
FIG. 17 is a flowchart illustrating an example of a flow of a positioning related display process executed by the control unit of the console of the first embodiment.

In step S216, the control unit 50 executes a positioning related display process shown in FIG. 17. FIG. 17 is a flowchart showing an example of a flow of a positioning related display process executed by the control unit 50 of the console 18 of this embodiment.

In step S350 in FIG. 17, the control unit 50 acquires order information regarding an imaging order set as an imaging order used for imaging. In a case where there is no set imaging order, it is preferable that the control unit 50 causes the display 56 to display an error indicating that there is no set imaging order.

In the next step S352, the control unit 50 acquires image data of a reference view for positioning. In this embodiment, the user causes the display 56 to display a reference view for positioning of the subject W. The reference view shows how to position (arrange) the subject W with respect to the radiographic imaging apparatus 14. Thus, in the console 18 of this embodiment, image data of reference views for positioning according to the imaging portions, the ages of subjects W, or the like is stored in the storage unit 52 in advance. Further, the control unit 50 acquires image data of a reference view for positioning from the storage unit 52 on the basis of acquired order information.

In the next step S354, the control unit 50 causes the display 56 to display a positioning related screen. Specifically, the control unit 50 generates the positioning related screen using the acquired image data of the reference view for positioning and information relating to a positioning related screen stored in the storage unit 52, and causes the display 56 to display the generated screen.

Figure 18:
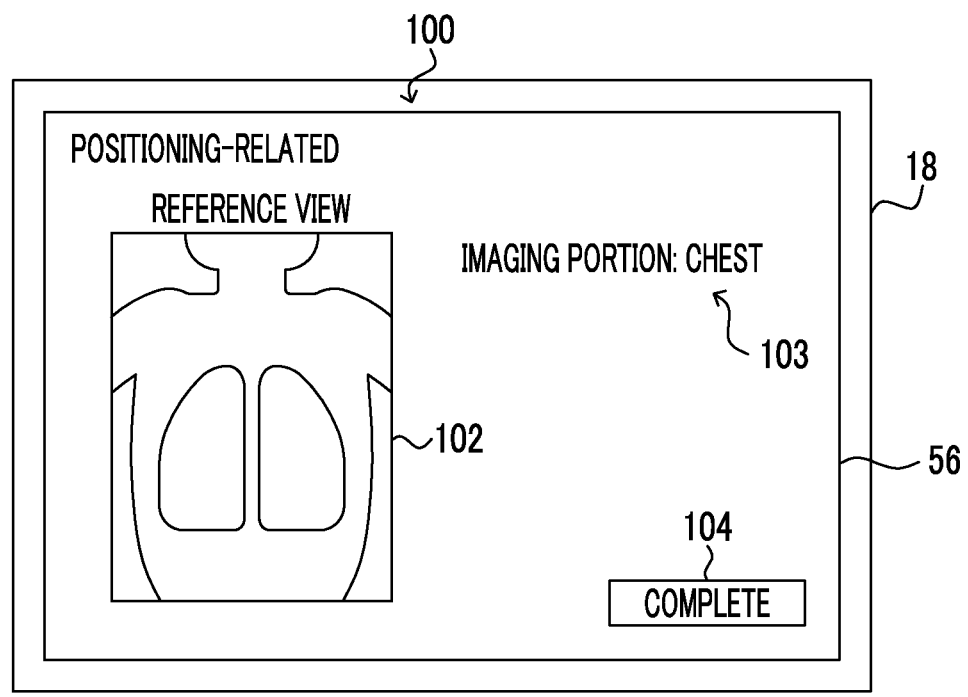
FIG. 18 is a schematic diagram illustrating a specific example of a state where a positioning related screen is displayed on the display of the console.

FIG. 18 is a schematic diagram illustrating a specific example of a state where a positioning related screen 100 is displayed on the display 56 of the console 18. On the positioning related screen 100 of this embodiment, display of a reference view 102 for positioning is performed. On the positioning related screen 100 of the specific example shown in FIG. 18, the reference view 102, information 103 indicating an imaging portion, and a complete button 104 are displayed.

The user positions the subject W between the radiographic imaging apparatus 14 and the radiation irradiator 12 with reference to the reference view 102. If the positioning is completed, the user designates the complete button 104.

In the next step S356A, the control unit 50 determines whether the complete button 104 is designated, and waits until it has been detected that the complete button 104 is designated. If it is detected that the complete button 104 is designated, the determination is affirmative, and then, the positioning related display process is terminated.

In this way, if the positioning related display process is terminated, the procedure returns to step S200 of the console single mode process, and then, the control unit 50 causes the display 56 to display the initial imaging screen 74 again.

On the other hand, in a case where the user selects a button other than the select button 75D on the initial imaging screen 74 displayed on the display 56, the determination is negative in step S214A, and then, the procedure proceeds to step S218. In a case where the user does not select the select buttons 75A to 75D on the initial imaging screen 74, that is, in a case where the select button 75E is selected, the procedure proceeds to step S218 in this way.

In step S218, the control unit 50 transmits an imaging start command signal to the radiographic imaging apparatus 14 on the basis of the order information regarding the set imaging order. If the imaging start command signal is received, the imaging control unit 22 of the radiographic imaging apparatus 14 performs a control for causing a status (state) of the radiation detector 20 to transition from a standby state to a ready state which is a state where detection of radiation R can be immediately performed.

The "standby state" in this embodiment refers to a state where a power source switch (not shown) of the radiographic imaging apparatus 14 is turned on and the radiographic imaging apparatus 14 waits until the imaging of a radiographic image is instructed. Further, the "ready state" in this embodiment refers to a state where the radiation detector 20 is able to immediately perform imaging and waits for the start of irradiation of the radiation R. In this way, in the ready state, since the radiation detector 20 performs an operation for detecting the start of irradiation of the radiation R, for example, the amount of power consumption is large, compared to the standby state.

In the next step S220, the control unit 50 causes the display 56 to display an imaging start screen. Specifically, the control unit 50 generates the imaging start screen using information relating to the imaging start screen stored in the storage unit 52, and causes the display 56 to display the generated screen.

Figure 19:
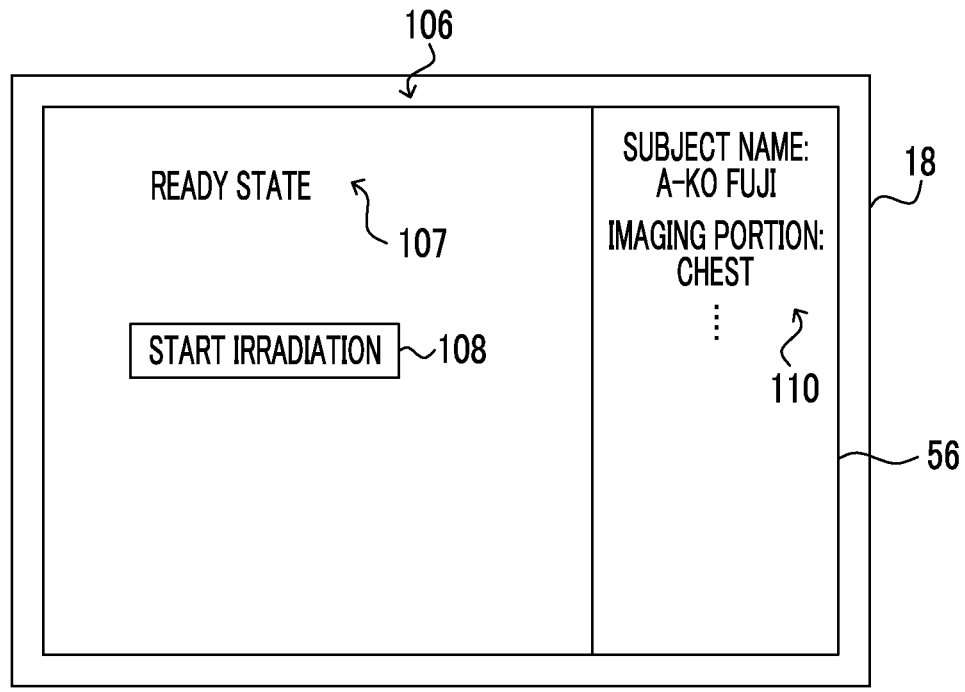
FIG. 19 is a schematic diagram illustrating a specific example of a state where an imaging start screen is displayed on the display of the console.

FIG. 19 is a schematic diagram illustrating a specific example of a state where an imaging start screen 106 is displayed on the display 56 of the console 18. Display for causing a user to perform an instruction relating to irradiation of radiation, for example, is performed on the imaging start screen 106 of this embodiment. For this reason, information 107 indicating the state (here, the ready state) of the radiographic imaging apparatus 14, an irradiation start button 108, and order information 110 of an imaging order used for imaging are displayed on the imaging start screen 106 of the specific example shown in FIG. 19.

By transmitting the imaging start signal to the radiographic imaging apparatus 14, the control unit 50 of this embodiment considers that the radiographic imaging apparatus 14 enters the ready state, and displays the information 107. This embodiment is not limited, and for example, in a case where a signal indicating that the radiographic imaging apparatus 14 has received the imaging start signal is received from the radiographic imaging apparatus 14, the control unit 50 may consider that the radiographic imaging apparatus 14 enters the ready state. The irradiation start button 108 is a button designated by a user in a case where the start of irradiation of the radiation R is instructed.

In step S222, the control unit 50 determines whether the start of irradiation of the radiation R is instructed. In this embodiment, in a case where the console 18 is connected to the radiographic imaging apparatus 14 as a control device, a radiographic imaging instruction may be given from the console 18 to the radiation irradiator 12. Thus, in step S222, the control unit 50 waits until it has been detected that the irradiation start button 108 is instructed. In a case where it is detected that the irradiation start button 108 is designated, the determination is affirmative, and then, the procedure proceeds to step S224.

In step S224, the control unit 50 transmits an irradiation start signal for instructing the start of irradiation of the radiation R to the radiation irradiator 12. In a case where the irradiation start signal transmitted from the console 18 is received, the radiation irradiator 12 performs irradiation of the radiation R.

Under the control of the console 18 described above, the radiation detector 20 detects the radiation R irradiated from the radiation irradiator 12 and passed through the subject W, to thereby generate a radiographic image based on the subject W.

In the radiographic imaging apparatus 14, imaging of a radiographic image is performed, and image data of a radiographic image obtained through imaging is transmitted to the console 18. In the radiographic imaging system 10 of this embodiment, radiographic image data obtained by performing image processing such as offset correction, gain correction, and defective pixel correction with respect to raw image data (hereinafter, referred to as raw data) in the radiographic imaging apparatus 14 is transmitted from the radiographic imaging apparatus 14 to the console 18. The image processing performed by the radiographic imaging apparatus 14 is not limited to this embodiment. Further, the radiographic imaging apparatus 14 may transmit the raw data to the console 18 without performing the image processing.

In step S226, the control unit 50 determines whether image data of a radiographic image is received. The control unit 50 waits until the image data is received, and if the image data is received, the procedure proceeds to step S228.

In step S228, the control unit 50 generates a radiographic image for reading from the received image data of the radiographic image. The control unit 50 of this embodiment performs image processing such as grid pattern removal (GPR), flexible noise control (FNC), multi-objective frequency processing (MFP), exposure data recognizer (EDR), virtual grid (VG, registered trademark) processing, with respect to the received image data of the radiographic image, as predetermined image processing, to thereby generate the radiographic image for reading. Here, it is sufficient if the radiographic image for reading to be displayed can be used for checking at least whether imaging of the radiographic image is suitable and has an image quality higher than that of a radiographic image for preview (hereinafter, referred to as a "preview image"), and may have an image quality lower than that of a radiographic image for reading used for actual medical examination or diagnosis by doctors.

In the next step S230, the control unit 50 causes the display 56 to display an image confirmation screen 112. In the next step S234, the control unit 50 causes the storage unit 52 to store the received image data of the radiographic image. The control unit 50 causes the storage unit 52 to store the image data of the radiographic image generated in step S228.

Figure 20:
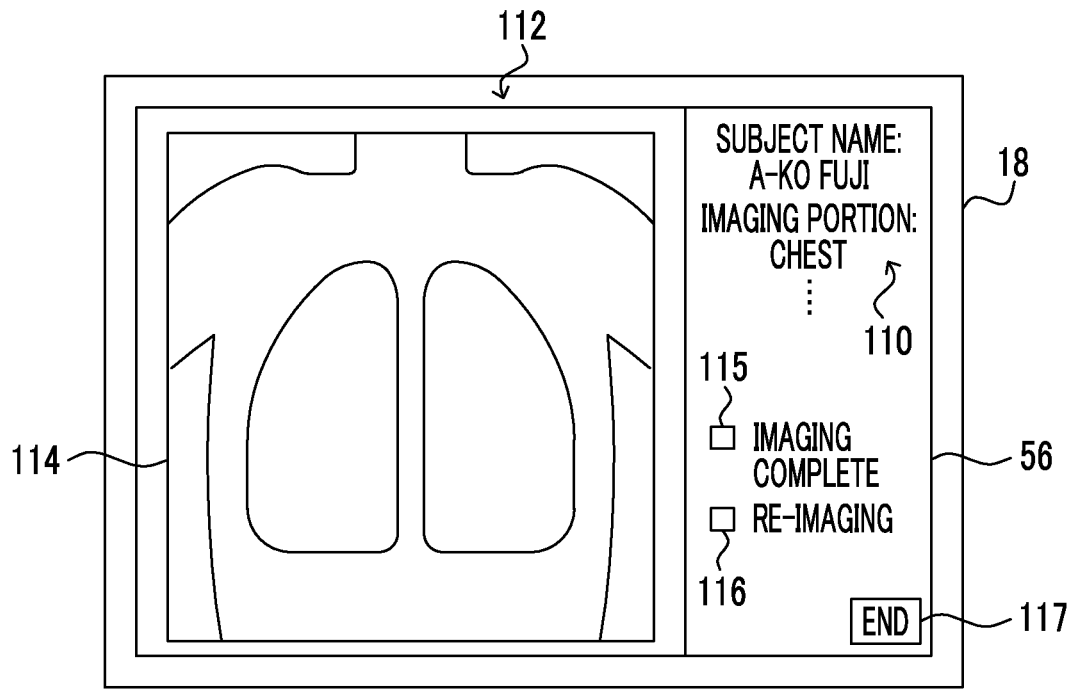
FIG. 20 is a schematic diagram illustrating a specific example of a state where an image confirmation screen is displayed on the display of the console.

FIG. 20 is a schematic diagram illustrating a specific example of a state where the image confirmation screen 112 is displayed on the display 56 of the console 18. Display for causing a user to confirm a captured radiographic image on the image confirmation screen 112 of this embodiment is performed on the image confirmation screen 112. Thus, a radiographic image for reading 114, order information 110 of an imaging order used for imaging, check boxes 115 and 116, and an end button 117 are displayed on the image confirmation screen 112 of the specific example shown in FIG. 20.

The radiographic image which is displayed on the image confirmation screen 112 under the control of the control unit 50 is not limited to this embodiment. For example, the control unit 50 may generate a preview image from the received image data of the radiographic image, and may display the generated preview image on the image confirmation screen 112.

The preview image is an image that allows a user to determine whether imaging of a radiographic image relating to a subject W has been suitably performed, and at least whether it is necessary to perform the imaging again. In a case where the preview image is generated, the control unit 50 of this embodiment uses a type of image processing that needs a relatively short time among a plurality of types of predetermined image processing performed in a case where a radiographic image for reading is generated, as image processing. Further, the control unit 50 of this embodiment also performs image processing for narrowing down the image data of a radiographic image as the image processing for generating a preview image. Thus, the amount of image data of the preview image becomes less than the amount of raw data.

In the console 18, the control unit 50 may cause the display 56 to display information relating to image processing for generating a radiographic image for reading or image processing for generating a preview image, and may cause a user to select image processing used for generation of each image or to set parameters in each image processing.

The user confirms the radiographic image 114 for reading, and determines whether to perform re-imaging. In the console 18 of this embodiment, in a case where the user instructs re-imaging, a check box 116 displayed on the display 56 is designated, and then, an end button 117 is designated.

On the other hand, in a case where imaging is completed without performing re-imaging, the user designates a check box 115 displayed on the display 56, and then, designates the end button 117.

In the next step S236, the control unit 50 detects such an operation. In a case where the control unit 50 detects that the check box 116 is designated, the determination is affirmative, and then, the procedure proceeds to step S238. In step S238, the control unit 50 transmits re-imaging instruction information to the radiographic imaging apparatus 14, and then, the procedure returns to step S220. The imaging control unit 22 of the radiographic imaging apparatus 14 that receives the re-imaging instruction information causes the radiation detector 20 to transition to a ready state to perform imaging of a radiographic image again.

In a case where imaging of a plurality of radiographic images is instructed with respect to one imaging order, for example, in a case where imaging of a plurality of radiographic images is performed with respect to the same subject W, the control unit 50 repeats the processes of steps S220 to S238. Further, in a case where imaging of a plurality of radiographic images is performed during one irradiation period of radiation R, for example, in the case of imaging a motion picture, the control unit 50 repeats the processes of steps S226 to S234.

On the other hand, in a case where the control unit 50 detects that the check box 115 is designated, the determination is negative, and then, the procedure proceeds to step S240. In step S240, the control unit 50 transmits imaging complete instruction information to the radiographic imaging apparatus 14, and then, the procedure proceeds to step S242. The imaging control unit 22 of the radiographic imaging apparatus 14 that receives the imaging complete instruction information causes the radiation detector 20 to transition to a sleep state. The "sleep state" in this embodiment refers to a state where only the CPU of the imaging control unit 22 is operated in the radiographic imaging apparatus 14, which has power consumption smaller than that in the standby state.

In step S242, the control unit 50 stores order information regarding an imaging order used for imaging in association with image data of a radiographic image in the storage unit 52.

Figure 21:
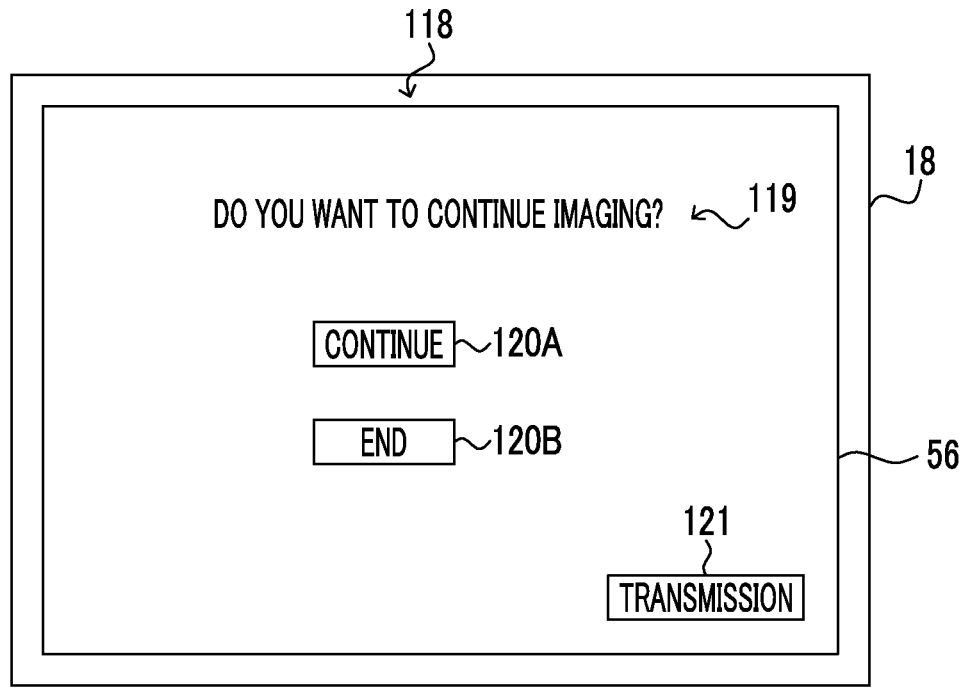
FIG. 21 is a schematic diagram illustrating a specific example of a state where an imaging continuation confirmation screen is displayed on the display of the console.

In step S244, the control unit 50 causes the display 56 to display an imaging continuation confirmation screen. FIG. 21 is a schematic diagram illustrating a specific example of a state where an imaging continuation confirmation screen 118 is displayed on the display 56 of the console 18. Display for selecting whether to continue imaging of a radiographic image by a user is performed on the imaging continuation confirmation screen 118 of this embodiment. Thus, on the imaging continuation confirmation screen 118 of the specific example shown in FIG. 21, information 119 for prompting a user to select whether to continue imaging of a radiographic image, a continuation button 120A, an end button 120B, and a transmission button 121 are displayed.

In a case where imaging of a radiographic image is continued, for example, in a case where a user wants to perform imaging using another imaging order, the user designates the continuation button 120A displayed on the display 56, and then, designates the transmission button 121. Here, the "continuation" of imaging does not relate to whether the same subject W is continued.

On the other hand, for example, in a case where imaging of a radiographic image is not continued, or in a case where the single mode is not continued as the control mode (a case where a user wants to change the control mode), the user designates the end button 120B displayed on the display 56, and then, designates the transmission button 121.

In the next step S246, the control unit 50 detects such an operation. In a case where the control unit 50 detects that the continuation button 120A is designated, the determination is affirmative, and then, the procedure proceeds to step S200. In the console 18 of this embodiment, in a case where imaging of a radiographic image is continued, a continuation signal is transmitted to the radiographic imaging apparatus 14. If the continuation signal is received, the imaging control unit 22 of the radiographic imaging apparatus 14 causes the radiation detector 20 to transition to the standby state.

On the other hand, in a case where the control unit 50 detects that the end button 120B is designated, the determination is negative, and then, the console single mode process is terminated. As described above, the procedure returns to step S110 of the console process.

Figure 22:
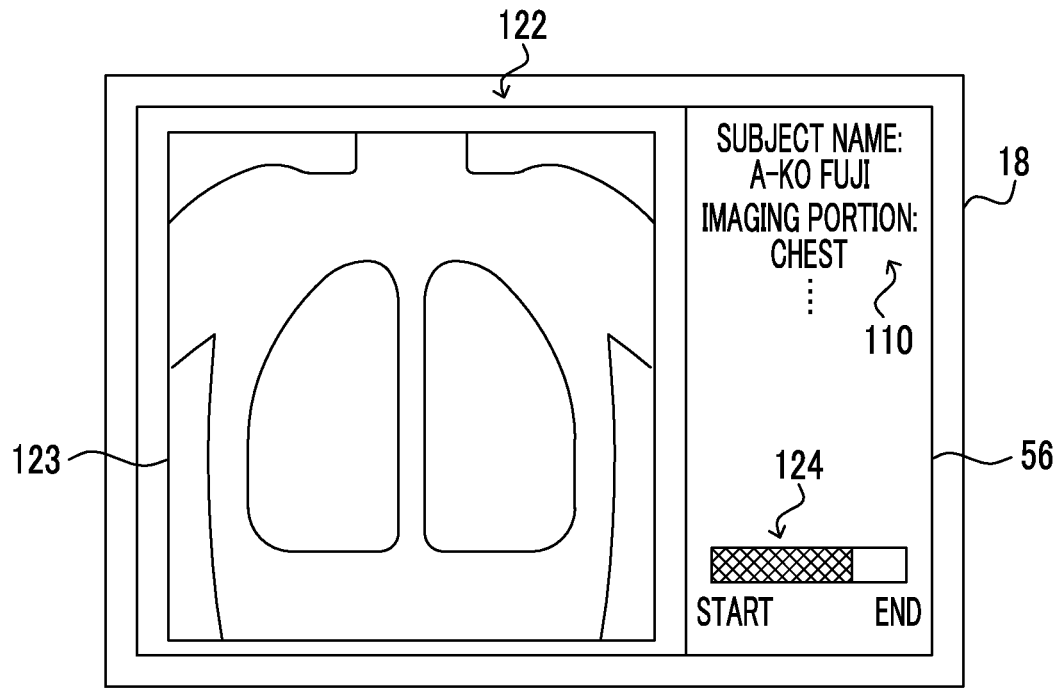
FIG. 22 is a schematic diagram illustrating a specific example of a state where an imaging status screen indicating information relating to a currently performed imaging status is displayed on the display of the console.

Display content displayed on the display 56 with respect to imaging of a radiographic image under the control of the control unit 50 of the console 18 is not limited to the above description. For example, display indicating information relating to a currently performed imaging status may be performed during imaging of a radiographic image. FIG. 22 is a schematic diagram illustrating a specific example of a state where an imaging status screen 122 indicating information relating to a currently performed imaging status on the display 56 of the console 18. A radiographic image 123, an indicator 124, and order information 110 of an imaging order used for imaging are displayed on the imaging status screen 122 of the specific example shown in FIG. 22. Since the radiographic image 123 is displayed during imaging, it is preferable that the radiographic image 123 is displayed in real time in conjunction with imaging. For this reason, it is preferable that the radiographic image 123 is generated by simplified image processing compared with a case where a radiographic image for reading is generated. For example, the radiographic image 123 may be the above-described preview image. Further, the indicator 124 is used for displaying an elapsed time (a remaining time up to the end) from the start of imaging. There is a case where imaging is performed over a long time compared with general imaging for one radiographic image, for example, a case of moving imaging, or a case where imaging is performed plural times within a predetermined time (10 seconds as a specific example). In such a case, a user can recognize an elapsed time from the start of imaging through display of the indicator 124, which is preferable.

Next, a console combination mode process in step S108 (see FIG. 3) of the console process, executed in the console 18 of this embodiment will be described. In a case where the control mode is the combination mode, the console combination mode process is executed in the console 18.

In a case where imaging is performed in an imaging room such as a general imaging room, a user may use the portable information terminal 16 in an imaging room where a subject W is present, and may use the console 18 provided outside the imaging room (for example, a console room, or the like), with respect to an instruction or an operation relating to imaging. In the radiographic imaging system 10 of this embodiment, in such a case, the control mode may be set to the combination mode for use.

As described above, in a case where the control mode of the radiographic imaging system 10 is the combination mode, a control relating to imaging of a radiographic image is performed by the portable information terminal 16 and the console 18. In this embodiment, the console 18 performs a main control, and the portable information terminal 16 functions as an assistant of the console 18. In this embodiment, the console 18 directly performs the control with respect to the radiographic imaging apparatus 14, and the portable information terminal 16 performs the control through the console 18. In this way, since a control device capable of directly performing the control with respect to the radiographic imaging apparatus 14 is set to only one console 18, it is possible to prevent discrepancies from occurring due to the control with respect to the radiographic imaging apparatus 14 from a plurality of control devices.

Since an overall flow of the console combination mode process executed by the control unit 50 of the console 18 of this embodiment is the same as in the above-described console single mode process (see FIGS. 5A and 5B), detailed description of the overall flow will not be repeated, and only different processes will be described.

Even in a case where the control unit 50 of this embodiment executes the console combination mode process, a user can perform various instructions and settings displayed on the above-described initial imaging screen 74 (see FIG. 6), similar to a case where the console single mode process is performed. Thus, the control unit 50 causes the display 56 to display the above-described various screens. Further, in the case of the combination mode, the user can perform various instructions and settings displayed on the initial imaging screen 74 (see FIG. 6) from the portable information terminal 16. Thus, the same screen as the initial imaging screen 74 (see FIG. 6) is displayed on the display 36 of the portable information terminal 16. The user can perform designation corresponding to the various screens through the operation unit 40 of the portable information terminal 16.

In this way, in a case where the user performs the designation through the operation unit 40 of the portable information terminal 16, the portable information terminal 16 transmits a designated content signal indicating content designated by the user to the console 18. In a case where the designated content signal is received, the control unit 50 of the console 18 performs the same process as in a case where the user performs designation through the operation unit 60 of the host device.

That is, in step S202B of the console combination mode process (see FIG. 5A), the control unit 50 determines whether a select button 135A of the initial imaging screen 134 displayed on the display 36 of the portable information terminal 16 or the select button 75A of the initial imaging screen 74 displayed on the display 56 of the console 18 is selected.

Further, in step S206B of the console combination mode process (see FIG. 5A), the control unit 50 determines whether a select button 135B of the initial imaging screen 134 displayed on the display 36 of the portable information terminal 16 or the select button 75B of the initial imaging screen 74 displayed on the display 56 of the console 18 is selected.

Further, in step S210B of the console combination mode process (see FIG. 5A), the control unit 50 determines whether a select button 135C of the initial imaging screen 134 displayed on the display 36 of the portable information terminal 16 or the select button 75C of the initial imaging screen 74 displayed on the display 56 of the console 18 is selected.

Further, in step S214B of the console combination mode process (see FIG. 5A), the control unit 50 determines whether a select button 135D of the initial imaging screen 134 displayed on the display 36 of the portable information terminal 16 or the select button 75D of the initial imaging screen 74 displayed on the display 56 of the console 18 is selected.

Similarly, in step S302B of the imaging apparatus setting display process (see FIG. 7), the control unit 50 determines whether a transmission button 140 of the imaging apparatus setting screen 138 displayed on the display 36 of the portable information terminal 16 or the transmission button 80 of the imaging apparatus setting screen 78 displayed on the display 56 of the console 18 is designated.

Similarly, in step S312B of the imaging order setting display process (see FIG. 9), in a case where the control unit 50 detects that a select button 143A of an imaging order setting screen 142 displayed on the display 36 of the portable information terminal 16 or the select button 83A of the imaging order setting screen 82 displayed on the display 56 of the console 18 is selected by the user, the determination is affirmative, and then, the procedure proceeds to step S314.

Further, in step S316B of the imaging order setting display process (see FIG. 9), the control unit 50 determines whether a transmission button 148 of an imaging order select screen 146 displayed on the display 36 of the portable information terminal 16 or the transmission button 88 of the imaging order select screen 86 displayed on the display 56 of the console 18 is designated.

Further, in step S322B of the imaging order setting display process (see FIG. 9), the control unit 50 determines whether a transmission button 152 of an imaging order input screen 150 displayed on the display 36 of the portable information terminal 16 or the transmission button 92 of the imaging order input screen 90 displayed on the display 56 of the console 18 is designated.

Similarly, in step S332B of the subject authentication display process (see FIG. 13), the control unit 50 determines whether subject information is read by the reader 33 of the portable information terminal 16 or the reader 61 of the console 18.

Further, in step S340B of the subject authentication display process (see FIG. 13), the control unit 50 determines whether a change button 158 (confirmation button 159) of a subject authentication screen 154 displayed on the display 36 of the portable information terminal 16 or the change button 98 (confirmation button 99) of the subject authentication screen 94 displayed on the display 56 of the console 18 is designated.

In addition, in step S356B of the positioning related display process (see FIG. 17), the control unit 50 determines whether a complete button 164 of a positioning related screen 160 displayed on the display 36 of the portable information terminal 16 or the complete button 104 of the positioning related screen 100 displayed on the display 56 of the console 18 is designated.

Through the above-described processes, the console 18 of this embodiment can perform a control relating to imaging of a radiographic image even in the case of the combination mode.

Figure 23:
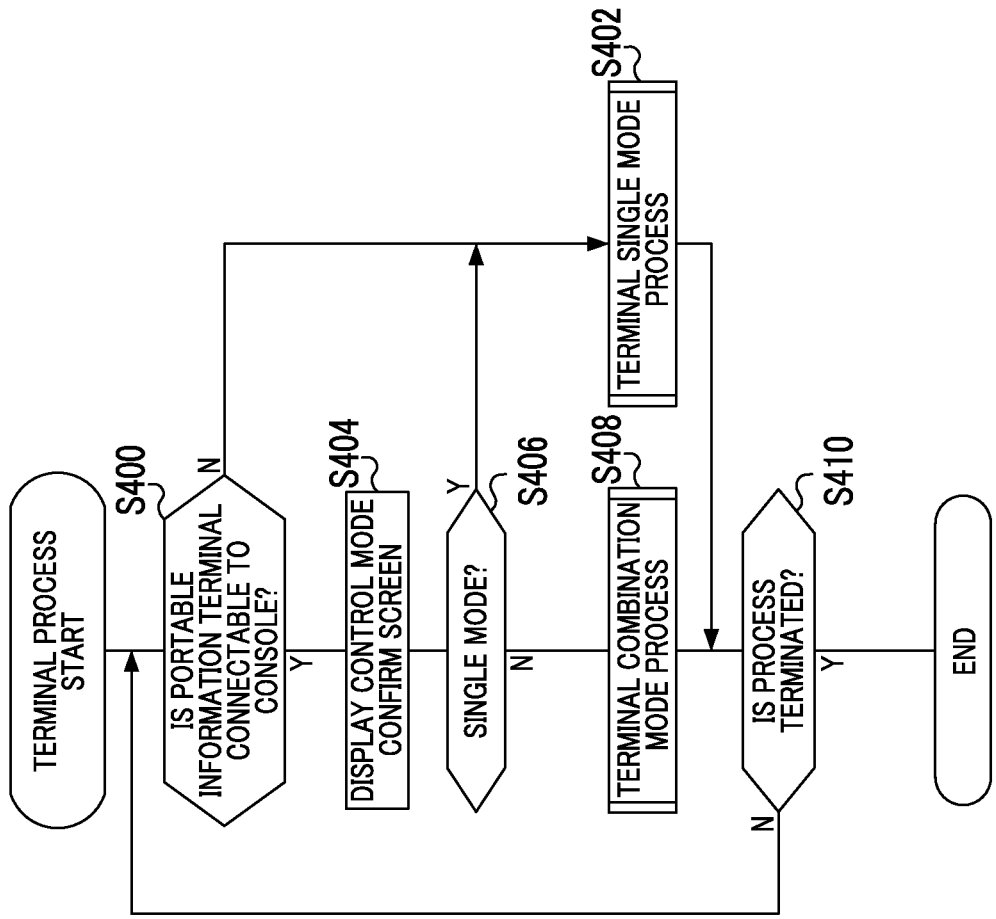
FIG. 23 is a flowchart illustrating an example of a flow of a terminal process executed by a terminal control unit of a portable information terminal of the first embodiment.

Next, an operation of the portable information terminal 16 will be described. FIG. 23 is a flowchart illustrating an example of a flow of a terminal process executed by the terminal control unit 30 of the portable information terminal 16 of this embodiment. In the portable information terminal 16 of this embodiment, the terminal control unit 30 executes a terminal process program stored in the ROM thereof, to thereby execute the terminal process.

In the following description, in a case where a user performs various designations or selections on various screens displayed on the display 36 (which will be described in detail later), the user performs the various designations or selections through the operation unit 40.

The terminal process is executed in a case where an instruction imaging a radiographic image is made through the operation unit 40, or in a case where a connection confirmation signal is received from the console 18, for example.

In step S400 in FIG. 23, the terminal control unit 30 determines whether the portable information terminal 16 is connectable to the console 18. As described above, in the radiographic imaging system 10 of this embodiment, in a case where communication is possible between the portable information terminal 16 and the console 18, since the combination mode may be set, it is determined whether the portable information terminal 16 is connectable to the console 18. A method for determining whether the connection is possible is the same as in step S100 in the overall flow of the console process (see FIG. 3).

In a case where the connection between the portable information terminal 16 and the console 18 is not possible, the determination is negative in step S400, and then, the procedure proceeds to step S402. In step S402, the terminal control unit 30 executes a terminal single mode process (which will be described later in detail), and then, the procedure proceeds to step S410.

On the other hand, in a case where the connection between the portable information terminal 16 and the console 18 is possible, in step S400, the determination is affirmative, and then, the procedure proceeds to step S404. In this case, in the radiographic imaging system 10 of this embodiment, the control mode may be set to the combination mode. However, even in this case, there is a case where a user needs to perform imaging in the terminal single mode.

Thus, in step S404, the terminal control unit 30 causes the display 36 to display a control mode confirmation screen. FIG. 24 is a schematic diagram illustrating a specific example of a state where a control mode confirmation screen 130 is displayed on the display 36 of the portable information terminal 16. The control mode confirmation screen 130 corresponds to the control mode confirmation screen 70 displayed on the console 18.

Information 131 for prompting a user to designate setting of any one of the combination mode and the single mode as the control mode, check boxes 132A and 132B, and a transmission button 133 are displayed on the control mode confirmation screen 130 of the specific example shown in FIG. 24. Here, the "single mode" refers to a single mode in which only the portable information terminal 16 performs a control relating to imaging of a radiographic image.

The user designates any box of the check boxes 132A and 132B corresponding to the set control mode, and then, designates the transmission button 133. If the terminal control unit 30 detects that the transmission button 133 is designated, the procedure proceeds to step S406.

In a case where the terminal control unit 30 detects that the check box 132B is designated, the determination is affirmative in step S406, and thus, the single mode is used as the control mode. Then, the procedure proceeds to step S402.

On the other hand, in a case where the terminal control unit 30 detects that the check box 132A is designated, the determination is negative in step S406, and thus, the combination mode is used as the control mode. Then, the procedure proceeds to step S408.

In step S408, the terminal control unit 30 executes a terminal combination mode process (which will be described in detail later), and then, the procedure proceeds to step S410.

In step S410, the terminal control unit 30 determines whether to terminate the terminal process. A method for determining whether to terminate the terminal process is the same as in step S110 in the overall flow of the console process (see FIG. 3). If the determination is negative in step S410, the procedure returns to step S400, and then, the terminal process is continued. On the other hand, if the determination is affirmative in step S410, the terminal process is terminated.

In order to prevent confusion in the control mode, in the console process (see FIG. 3), in a case where the console 18 is set to the combination mode, it is preferable that the portable information terminal 16 is also set to the combination mode regardless of the setting of the user.

Figure 25A:
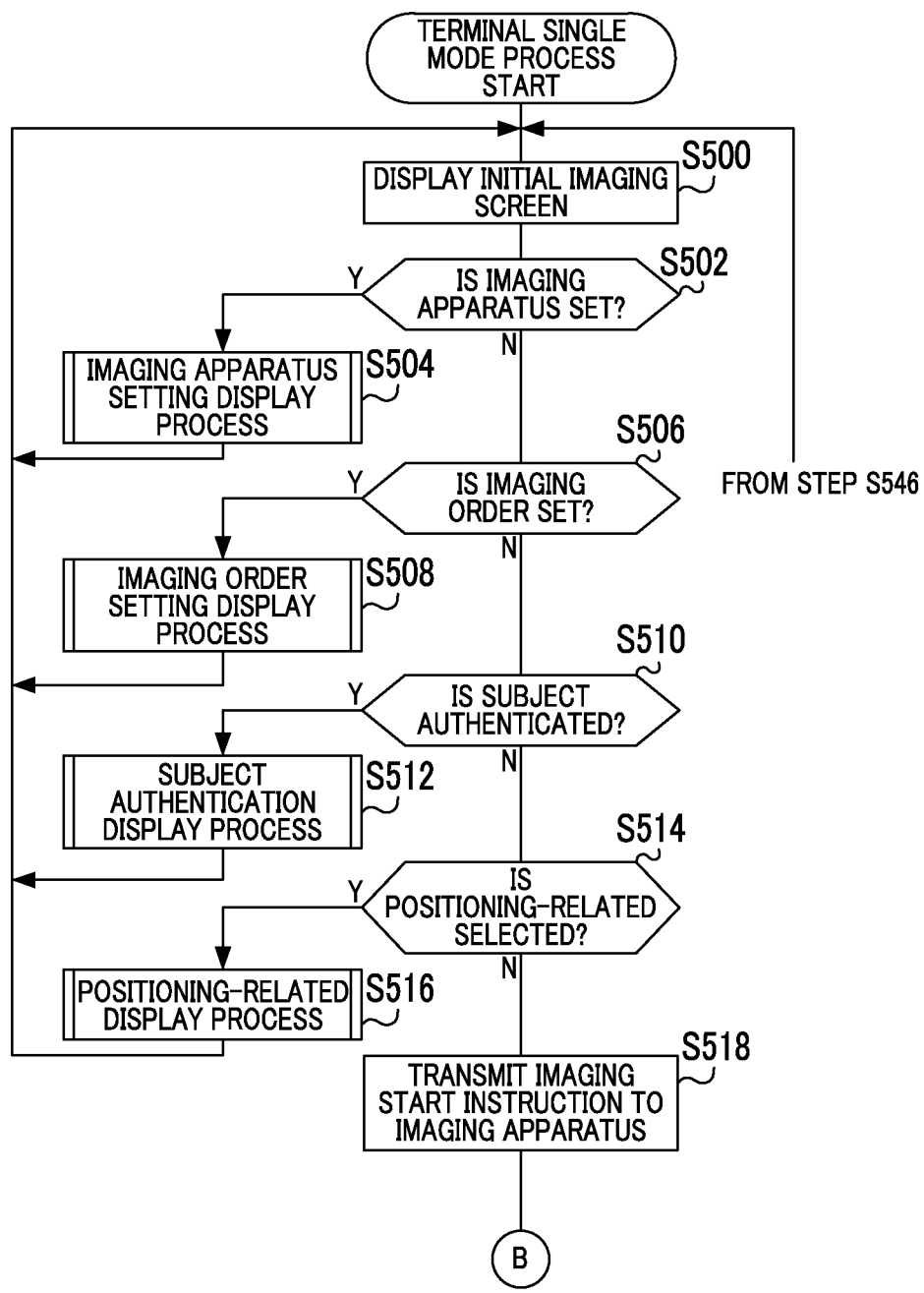
FIG. 25A is a flowchart illustrating an example of a flow of a terminal single mode process executed by the terminal control unit of the portable information terminal of the first embodiment.
Figure 25B:
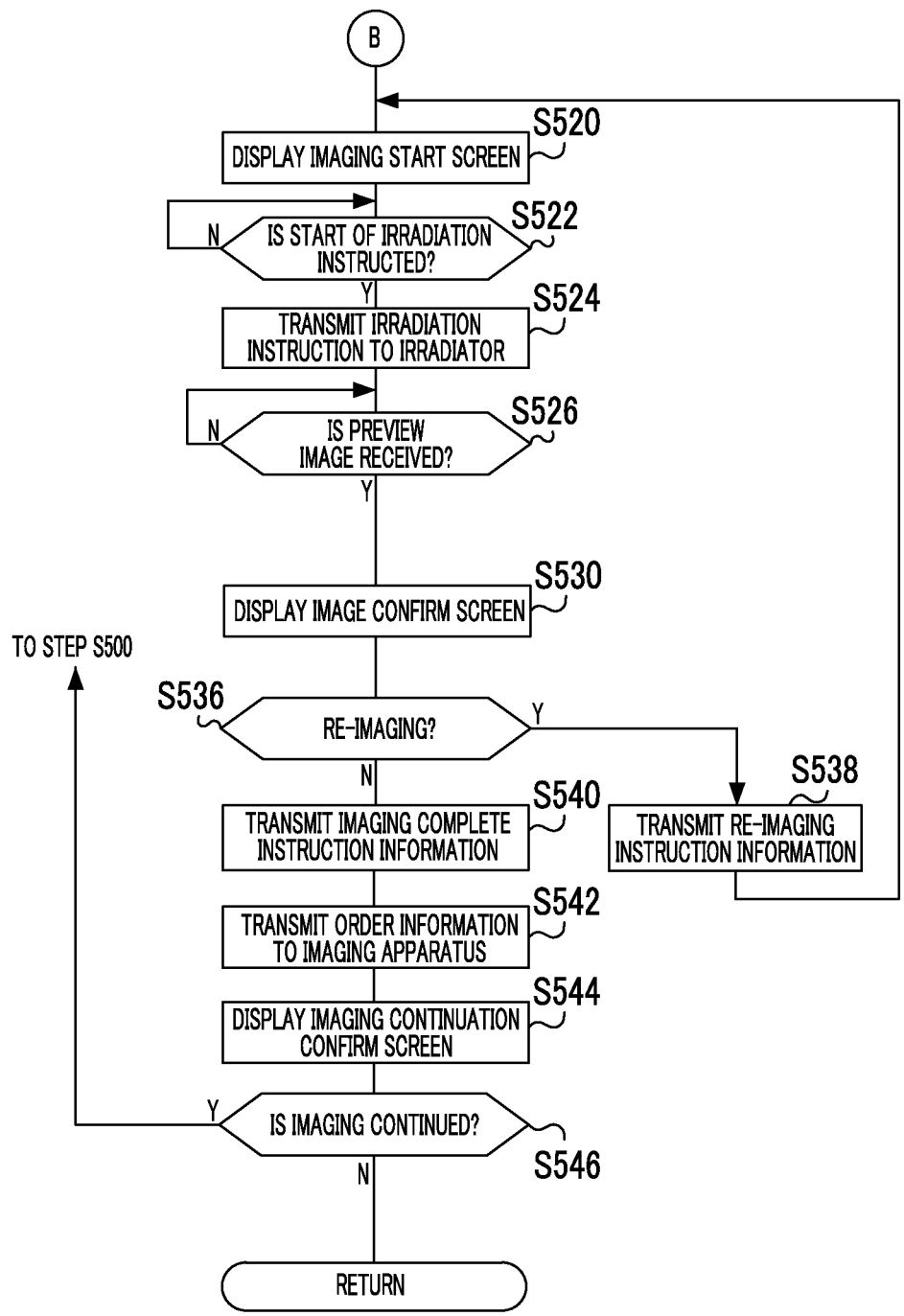
FIG. 25B is a flowchart illustrating an example of a flow of the terminal single mode process, subsequent to the flow of FIG. 25A.

Next, the terminal single mode process of step S402 (see FIG. 23) in the terminal process, executed by the portable information terminal 16 of this embodiment, will be described. FIGS. 25A and 25B are flowcharts illustrating an example of a flow of a terminal single mode process executed by the terminal control unit 30 of the portable information terminal 16 of this embodiment.

Various screens displayed on the display 36 of the portable information terminal 16 correspond to various screens displayed on the display 56 of the console 18 having the same names.

In step S500 in FIG. 25A, the terminal control unit 30 causes the display 36 to display the initial imaging screen 134. FIG. 26 is a schematic diagram illustrating a specific example of a state where the initial imaging screen 134 is displayed on the display 36 of the portable information terminal 16. Select buttons 135A to 135E and a transmission button 136 are displayed on the initial imaging screen 134 of the specific example shown in FIG. 26. The select buttons 135A to 135E and the transmission button 136 respectively correspond to the select buttons 75A to 75E and the transmission button 76 displayed on the initial imaging screen 74 (see FIG. 6).

A user selects any one of the select buttons 135A to 135E, and then, designates the transmission button 136. If the terminal control unit 30 detects that the transmission button 136 is designated, the procedure proceeds to step S502.

In step S502, the terminal control unit 30 determines whether "imaging apparatus setting" is selected on the initial imaging screen 134. If the determination is affirmative, the procedure proceeds to step S504.

In step S504, since an imaging apparatus setting display process executed by the terminal control unit 30 is the same as the imaging apparatus setting display process (see FIG. 7) executed by the control unit 50 of the console 18, descriptions will be made with reference to FIG. 7.

In step S300 in FIG. 7, the terminal control unit 30 causes the display 36 to display an imaging apparatus setting screen. FIG. 27 is a schematic diagram illustrating a specific example of a state where an imaging apparatus setting screen 138 is displayed on the display 36 of the portable information terminal 16. Check boxes 139A to 139C and a transmission button 140 are displayed on the imaging apparatus setting screen 138 of the specific example shown in FIG. 27. The check boxes 139A to 139C and the transmission button 140 respectively correspond to the check boxes 79A to 79C and the transmission button 80 displayed on the imaging apparatus setting screen 78 (see FIG. 8). A user designates any one of the check boxes 139A to 139C corresponding to the radiographic imaging apparatus 14 to be used for imaging a radiographic image, and then, designates the transmission button 140.

Thus, in the next step S302A, the terminal control unit 30 determines whether the transmission button 140 is designated. If the determination is negative, the terminal control unit 30 waits for the designation, and if the determination is affirmative, the procedure proceeds to step S304.

In step S304, the terminal control unit 30 detects a check box designated by the user, performs a setting depending on the radiographic imaging apparatus 14 corresponding to the detected check box, and then, terminates the imaging apparatus setting display process.

If the imaging apparatus setting display process is terminated in this way, the procedure returns to step S500 of the terminal single mode process.

On the other hand, if the determination is negative in step S502, the procedure proceeds to step S506.

In step S506, the terminal control unit 30 determines whether "imaging order setting" is selected on the initial imaging screen 134. If the determination is affirmative, the procedure proceeds to step S508.

In step S508, since an imaging order setting display process executed by the terminal control unit 30 is the same as the imaging order setting display process (see FIG. 9) executed by the control unit 50 of the console 18, descriptions will be made with reference to FIG. 9.

In step S310 in FIG. 9, the terminal control unit 30 causes the display 36 to display an imaging order setting screen. FIG. 28 is a schematic diagram illustrating a specific example of a state where an imaging order setting screen 142 is displayed on the display 36 of the portable information terminal 16. Select buttons 143A, 143B, and a transmission button 144 are displayed on the imaging apparatus setting screen 132 of the specific example shown in FIG. 28. The select buttons 143A, 143B, and the transmission button 84 respectively correspond to the select buttons 83A, 83B, and the transmission button 84 displayed on the imaging order setting screen 82 (see FIG. 10).

In the next step S312A, the terminal control unit 30 determines whether selection of an imaging order is to be performed. If the determination is affirmative, the procedure proceeds to step S314.

In step S314, the terminal control unit 30 causes the display 36 to display an imaging order select screen. FIG. 29 is a schematic diagram illustrating a specific example of a state where an imaging order select screen 146 is displayed on the display 36 of the portable information terminal 16. Check boxes 147A to 147C, and a transmission button 148 are displayed on the imaging order select screen 146 of the specific example shown in FIG. 29. The check boxes 147A to 147C, and the transmission button 148 in the specific example shown in FIG. 29 respectively correspond to the check boxes 87A to 87C, and the transmission button 88 displayed on the imaging order select screen 86 (see FIG. 11).

Further, in the imaging order select screen 146 of this embodiment, order information corresponding to each imaging order is also displayed to support selection of the imaging order. The order information displayed on the imaging order select screen 86 is smaller than the order information displayed on the imaging order select screen 86 (see FIG. 11).

In the next step S316A, if the determination is affirmative, the procedure proceeds to step S318.

In step S318, the terminal control unit 30 detects a check box designated by the user, among the check boxes 147A to 147C, sets the detected check box as an imaging order used for imaging, and then, terminates the imaging order setting display process. Thus, thereafter, imaging of a radiographic image is performed on the basis of the set imaging order.

On the other hand, if the determination is negative in step S312A, the procedure proceeds to step S320.

In step S320, the terminal control unit 30 causes the display 36 to display an imaging order input screen. FIG. 30 is a schematic diagram illustrating a specific example of a state where an imaging order input screen 150 is displayed on the display 36 of the portable information terminal 16. Information 151 and a transmission button 152 are displayed on the imaging order input screen 150 of the specific example shown in FIG. 30. The information 151 and the transmission button 152 respectively correspond to the information 91 and the transmission button 92 displayed on the imaging order input screen 90 (see FIG. 12).

In the next step S322A, if the determination is affirmative, the procedure proceeds to step S324.

In step S324, the terminal control unit 30 detects an imaging order input by the user, sets the detected imaging order as an imaging order used for imaging, and then, terminates the imaging order setting display process. Thus, thereafter, imaging of a radiographic image is performed on the basis of the set imaging order.

If the imaging order setting display process is terminated in this way, the procedure returns to step S500 of the terminal single mode process.

On the other hand, if the determination is negative in step S506, the procedure proceeds to step S510.

In step S510, the terminal control unit 30 determines whether "subject authentication" is selected on the initial imaging screen 134. If the determination is affirmative, the procedure proceeds to step S512.

In step S512, since a subject authentication display process executed by the terminal control unit 30 is the same as the subject authentication display process (see FIG. 13) executed by the control unit 50 of the console 18, description will be made with reference to FIG. 13.

In step S330 in FIG. 13, the terminal control unit 30 causes the display 56 to display a subject authentication screen.

FIG. 31 is a schematic diagram illustrating a specific example of a state where a subject authentication screen 154 is displayed on the display 36 of the portable information terminal 16. Information 155 is displayed on the subject authentication screen 154 of the specific example shown in FIG. 31. The information 155 corresponds to the information 95 displayed on the subject authentication screen 94 (see FIG. 14).

In the next step S332A, the terminal control unit 30 determines whether subject information is read by the reader 33. If the determination is negative, the terminal control unit 30 waits for the reading, and if the determination is affirmative, the procedure proceeds to step S334.

In step S334, the terminal control unit 30 determines whether an imaging order corresponding to the read subject information is present. If the determination is negative, the procedure proceeds to step S336.

Figure 32:
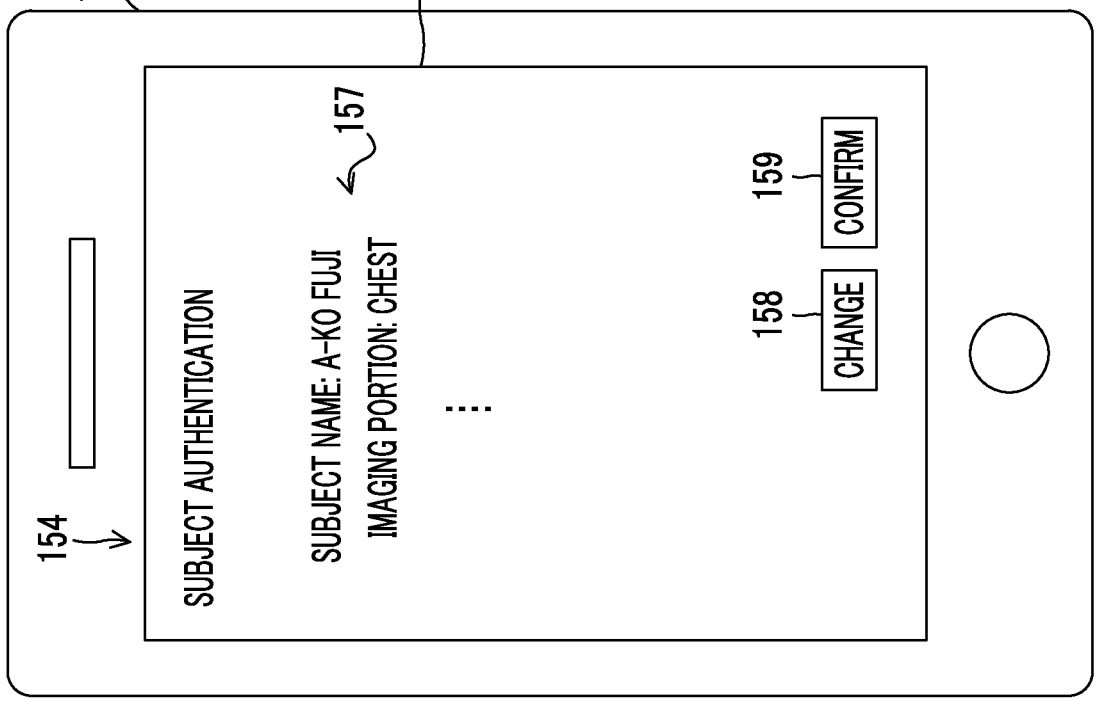
FIG. 32 is a schematic diagram illustrating a specific example of a state where a reading result is displayed on the subject authentication screen.

In step S336, the terminal control unit 30 displays a reading result indicating that the imaging order is not present on the subject authentication screen 154, and then, the procedure proceeds to step S340A. FIG. 32 is a schematic diagram illustrating a specific example of a state where a reading result is displayed on the subject authentication screen 154. Information 156, a change button 158, and a confirmation button 159 are displayed on the subject authentication screen 154 of the specific example shown in FIG. 32. The information 156, the change button 158, and the confirmation button 159 respectively correspond to the information 96, the change button 98, and the confirmation button 99 displayed on the subject authentication screen 94 (see FIG. 15).

On the other hand, in step S334, in a case where the imaging order corresponding to the read subject information is present, the determination is affirmative, and then, the procedure proceeds to step S338.

Figure 33:
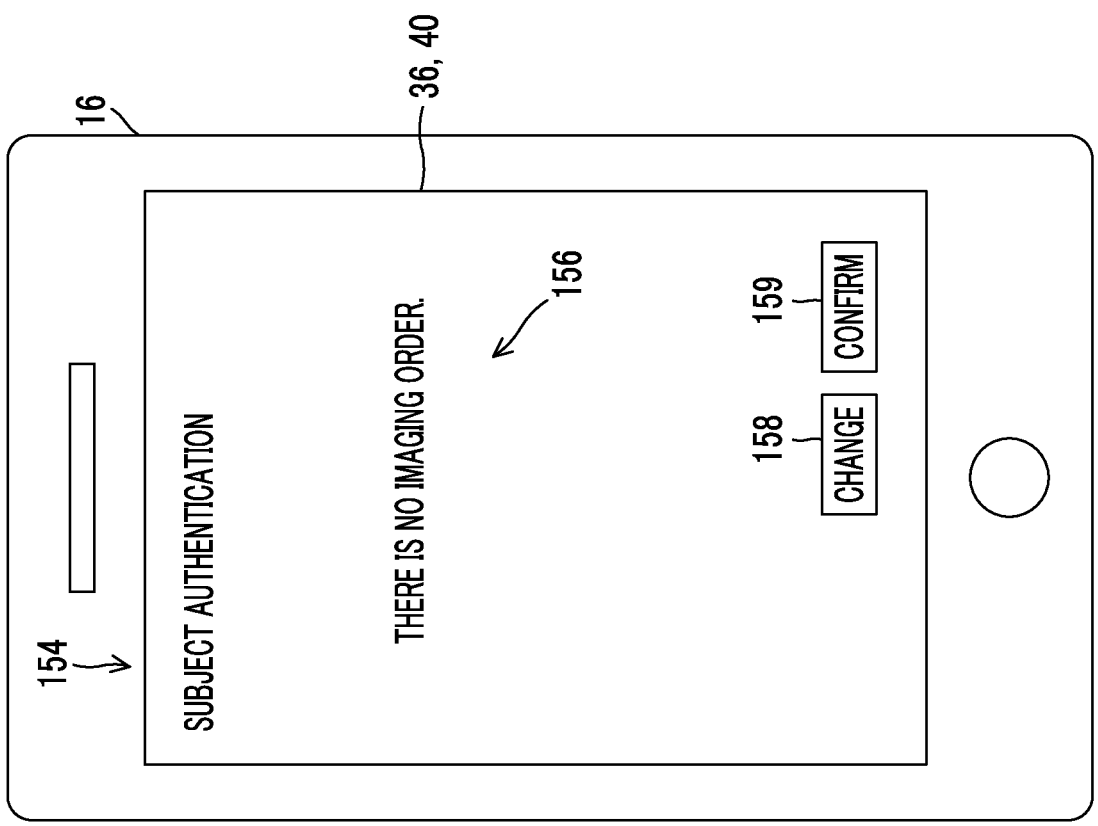
FIG. 33 is a schematic diagram illustrating a specific example of a state where a reading result is displayed on the subject authentication screen.

In step S338, the terminal control unit 30 displays order information regarding the imaging order on the subject authentication screen 154 as a reading result, and then, the procedure proceeds to step S340A. FIG. 33 is a schematic diagram illustrating a specific example of a state where a reading result is displayed on the subject authentication screen 154. Order information 157 of the imaging order, the change button 158, and the confirmation button 159 are displayed on the subject authentication screen 154 of the specific example shown in FIG. 33. The order information 157, the change button 158, and the confirmation button 159 respectively correspond to the order information 97, the change button 98, and the confirmation button 99 displayed on the subject authentication screen 154 (see FIG. 16).

If the determination is affirmative in step S340A, the procedure returns to step S330 to repeat the subject authentication display process. On the other hand, if the determination is negative, the subject authentication display process is terminated.

If the subject authentication display process is terminated in this way, the procedure returns to step S500 of the terminal single mode process.

On the other hand, if the determination is negative in step S510, the procedure proceeds to step S514.

In step S514, the terminal control unit 30 determines whether "positioning related" is selected on the initial imaging screen 134. If the determination is affirmative, the procedure proceeds to step S516.

In step S516, since the positioning related display process executed by the terminal control unit 30 is the same as the positioning related display process (see FIG. 17) executed by the control unit 50 of the console 18, description will be made with reference to FIG. 17.

In step S350 in FIG. 17, the terminal control unit 30 acquires order information regarding an imaging order set as an imaging order for imaging.

In the next step S352, the terminal control unit 30 acquires image data of a reference view for positioning from the storage unit 32.

In the next step S354, the terminal control unit 30 causes the display 36 to display a positioning related screen. FIG. 34 is a schematic diagram illustrating a specific example of a state where a positioning related screen 160 is displayed on the display 36 of the portable information terminal 16. A reference view 162 and a complete button 164 are displayed on the positioning related screen 160 of the specific example shown in FIG. 34. The reference view 162 and the complete button 164 respectively correspond to the reference view 102 and the complete button 104 displayed on the positioning related screen 100 (see FIG. 18).

In the next step S356A, if the determination is negative, the terminal control unit 30 waits for designation of the complete button 164, and if the determination is affirmative, the positioning related display process is terminated.

If the positioning related display process is terminated in this way, the procedure returns to step S500 of the terminal single mode process.

On the other hand, if the determination is negative in step S514, the procedure proceeds to step S518.

In step S518, the terminal control unit 30 transmits an imaging start command signal to the radiographic imaging apparatus 14 on the basis of the order information regarding the set imaging order. If the imaging start command signal is received, the imaging control unit 22 of the radiographic imaging apparatus 14 performs a control for causing the state of the radiation detector 20 to transition from a standby state to a ready state which is a state where detection of radiation R can be immediately performed.

In this embodiment, the imaging start command signal transmitted from the portable information terminal 16 to the radiographic imaging apparatus 14 includes information for setting an imaging mode of the radiographic imaging apparatus 14 to a memory mode. The radiographic imaging apparatus 14 of this embodiment includes a plurality of imaging modes including the memory mode. The memory mode is an imaging mode in which image data of radiographic images the number of which corresponds to at least a plurality of imaging orders is stored in the memory 24 in the radiographic imaging apparatus 14 and a preview image is generated from the image data (raw data) on the radiographic image and is transmitted to the control device. Thus, the radiographic imaging apparatus 14 that receives the imaging start command signal is operated with the imaging mode being set to the memory mode.

In the next step S520, the terminal control unit 30 causes the display 36 to display an imaging start screen. FIG. 35 is a schematic diagram illustrating a specific example of a state where an imaging start screen 166 is displayed on the display 36 of the portable information terminal 16. Information 167 and an irradiation start button 168 are displayed on the imaging start screen 166 of the specific example shown in FIG. 35. The information 167 and the irradiation start button 168 respectively correspond to the information 107 and the irradiation start button 108 displayed on the imaging start screen 106 (see FIG. 19).

In step S522, the terminal control unit 30 determines whether the start of irradiation of radiation R is instructed. In this embodiment, in a case where the portable information terminal 16 is connected to the radiographic imaging apparatus 14 as a control device, it is possible to instruct the radiation irradiator 12 to capture a radiographic image from the portable information terminal 16. Thus, if the determination is affirmative in step S522, the procedure proceeds to step S524.

In step S524, the terminal control unit 30 transmits an irradiation start signal for instructing the radiation irradiator 12 to start irradiation of radiation R.

Under the control of the portable information terminal 16 described above, the radiation detector 20 detects radiation R irradiated from the radiation irradiator 12 and passed through a subject W, to thereby generate a radiographic image based on the subject W.

The radiographic imaging apparatus 14 captures a radiographic image, stores image data of a radiographic image obtained through imaging in the memory 24, generates a preview image from the image data of the radiographic image, and transmits the image data of the preview image to the portable information terminal 16. The generation of the preview image may be the same as the generation of the preview image in the above-described console 18.

In step S526, if the determination is negative, the terminal control unit 30 waits for reception of the preview image, and if the determination is affirmative, the procedure proceeds to step S528.

In the next step S530, the terminal control unit 30 causes the display 36 to display an image confirmation screen 170.

FIG. 36 is a schematic diagram illustrating a specific example of a state where an image confirmation screen 112 is displayed on the display 36 of the portable information terminal 16. Display for confirming a radiographic image captured by a user is performed on the image confirmation screen 112 of this embodiment. Thus, a preview image 172 which is smaller than a radiographic image for reading, order information 171, check boxes 173 and 174, and an end button 175 are displayed on the image confirmation screen 170 of the specific example shown in FIG. 36. The order information 171, the check boxes 173 and 174, and the end button 175 respectively correspond to the order information 110, the check boxes 115 and 116, and the end button 117 displayed on the image confirmation screen 112 (see FIG. 20).

The user confirms the preview image 172, and determines whether re-imaging is to be performed.

In the next step S536, if the determination is affirmative, the procedure proceeds to step S538. In step S538, the terminal control unit 30 transmits re-imaging instruction information to the radiographic imaging apparatus 14, and then, the procedure returns to step S520.

In a case where imaging of a plurality of radiographic images is instructed with respect to one imaging order, for example, in a case where imaging of a plurality of radiographic images is performed with respect to the same subject W, the terminal control unit 30 repeats the processes of steps S520 to S538. Further, in a case where imaging of a plurality of radiographic images is performed during one irradiation period of radiation R, for example, in the case of imaging of a motion picture, the terminal control unit 30 repeats the processes of steps S520 to S530.

On the other hand, if the determination is negative in step S536, the procedure proceeds to step S540. In step S540, the terminal control unit 30 transmits imaging complete instruction information to the radiographic imaging apparatus 14, and then, the procedure proceeds to step S542.

In step S542, the terminal control unit 30 transmits order information regarding an imaging order used for imaging to the radiographic imaging apparatus 14. The radiographic imaging apparatus 14 that has received the order information is stored in the memory 24 in association with image data of a radiographic image obtained by imaging.

In step S544, the terminal control unit 30 causes the display 36 to display an imaging continuation confirmation screen. FIG. 37 is a schematic diagram illustrating a specific example of a state where an imaging continuation confirmation screen 176 is displayed on the display 36 of the portable information terminal 16. Information 177, a continuation button 178A, an end button 178B, and a transmission button 180 are displayed on the imaging continuation confirmation screen 176 of the specific example shown in FIG. 37. The information 177, the continuation button 178A, the end button 178B, and the transmission button 180 respectively correspond to the information 119 of the imaging continuation confirmation screen 118 (see FIG. 21), the continuation button 120A, the end button 120B, and the transmission button 121.

In the next step S546, if the determination is affirmative, the procedure proceeds to step S500. On the other hand, if the determination is negative, the terminal single mode process is terminated, and then, the procedure returns to step S500 of the terminal process as described above.

Display content displayed on the display 36 with respect to imaging of a radiographic image under the control of the terminal control unit 30 of the portable information terminal 16 is not limited to the above description. FIG. 38 is a schematic diagram illustrating a specific example of a state where an imaging status screen 182 indicating information relating to a currently performed imaging status is displayed on the display 36 of the portable information terminal 16. A preview image 172, an indicator 184, and order information 183 of an imaging order used for imaging are displayed on the imaging status screen 122 of the specific example shown in FIG. 38.

Next, the terminal combination mode process of step S408 (see FIG. 23) in the terminal process, executed by the portable information terminal 16 of this embodiment, will be described. In a case where the control mode is the combination mode, the terminal combination mode process is executed by the portable information terminal 16. FIG. 39 is a flowchart illustrating an example of a flow of a terminal combination mode process executed by the terminal control unit 30 of the portable information terminal 16 of this embodiment.

In the overall terminal combination mode process executed by the terminal control unit 30 of the portable information terminal 16 of this embodiment, the same processes are performed except that the processes of steps S518 to S544 of the above-described terminal single mode process (see FIGS. 25A and 25B) are not executed.

In the case of the combination mode, during irradiation of radiation R, a user is present in the vicinity of the console 18 separated from the radiation irradiator 12 and performs an instruction relating to the irradiation of the radiation R or confirmation of a radiographic image in the console 18, in many cases. For this reason, in the terminal combination mode process, the portable information terminal 16 does not perform such an instruction. Thus, if the determination is negative in step S514, the procedure proceeds to step S546.

If the determination is negative in step S514, since a subsequent operation is performed in the console 18, the portable information terminal 16 may transition to a state where an instruction from a user is not received.

Through the above-mentioned processes, in the portable information terminal 16 of this embodiment, even in the case of the combination mode, it is possible to perform a control relating to imaging of a radiographic image. Further, it is possible to reduce the display content compared with the display content displayed on the display 36 in the single mode process, and thus, it is possible to increase the size of each piece of display content. Accordingly, the user can easily view the display content.

Second Embodiment

Next, a second embodiment will be described. With respect to the same portions as in the radiographic imaging system 1 according to the first embodiment, detailed description thereof will not be repeated.

As shown in FIG. 40, an overall configuration of the radiographic imaging system 1 of this embodiment is different from the radiographic imaging system 1 (see FIG. 1) of the first embodiment in that an irradiation switch 19.

An irradiation switch 19 is a switch dedicated to an execution instruction of irradiation of radiation R, provided separately from the portable information terminal 16 and the console 18. In the radiographic imaging system 10 of this embodiment, in the case of the irradiation of the radiation R, a user instructs the radiation irradiator 12 to execute the irradiation of the radiation R using the irradiation switch 19.

Figure 41:
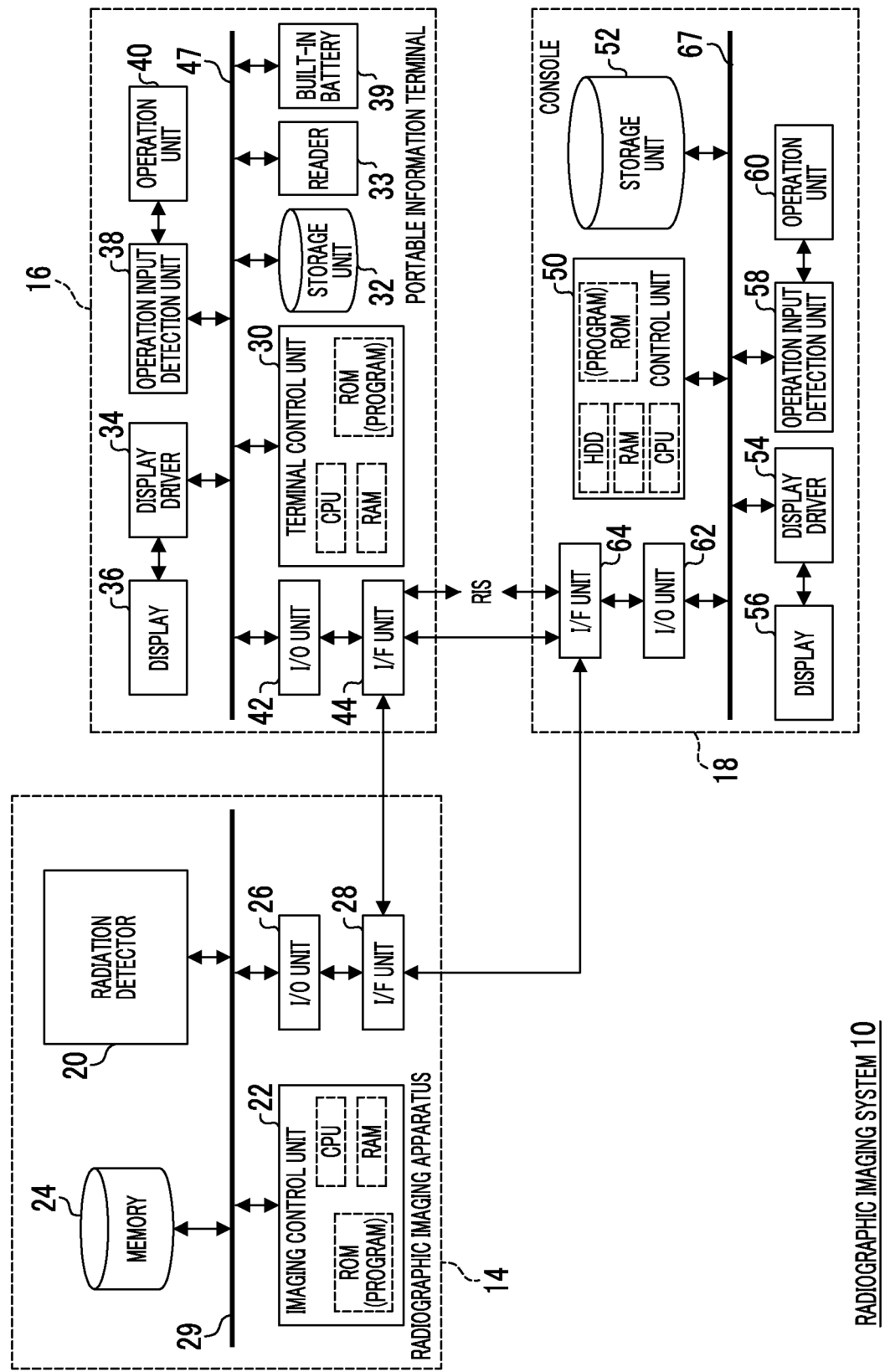
FIG. 41 is a block diagram illustrating an example of a schematic configuration of a radiographic imaging apparatus, a portable information terminal, and a console of the second embodiment.

Further, the radiographic imaging system 10 of this embodiment has a configuration of the console 18 different from that in the first embodiment. As shown in FIG. 41, the console 18 of this embodiment is different from the console 18 (see FIG. 2) of the first embodiment in that the reader 61 is not provided. In addition, the console 18 of this embodiment has a configuration in which the display 56 and the operation unit 60 are integrated to form a touch panel display.

Further, in the radiographic imaging system 10 of this embodiment, since a part of an operation of imaging a radiographic image is different from that of the first embodiment, the different configuration will be described.

First, an operation of the console 18 of this embodiment will be described. An overall flow of a console process executed by the control unit 50 of the console 18 is the same as in the first embodiment (see FIG. 3). In this embodiment, since respective pieces of process content of the console single mode process in step S102 of the console process and the console combination mode process in step S108 are different from those of the first embodiment, the respective processes will be described.

Figure 42:
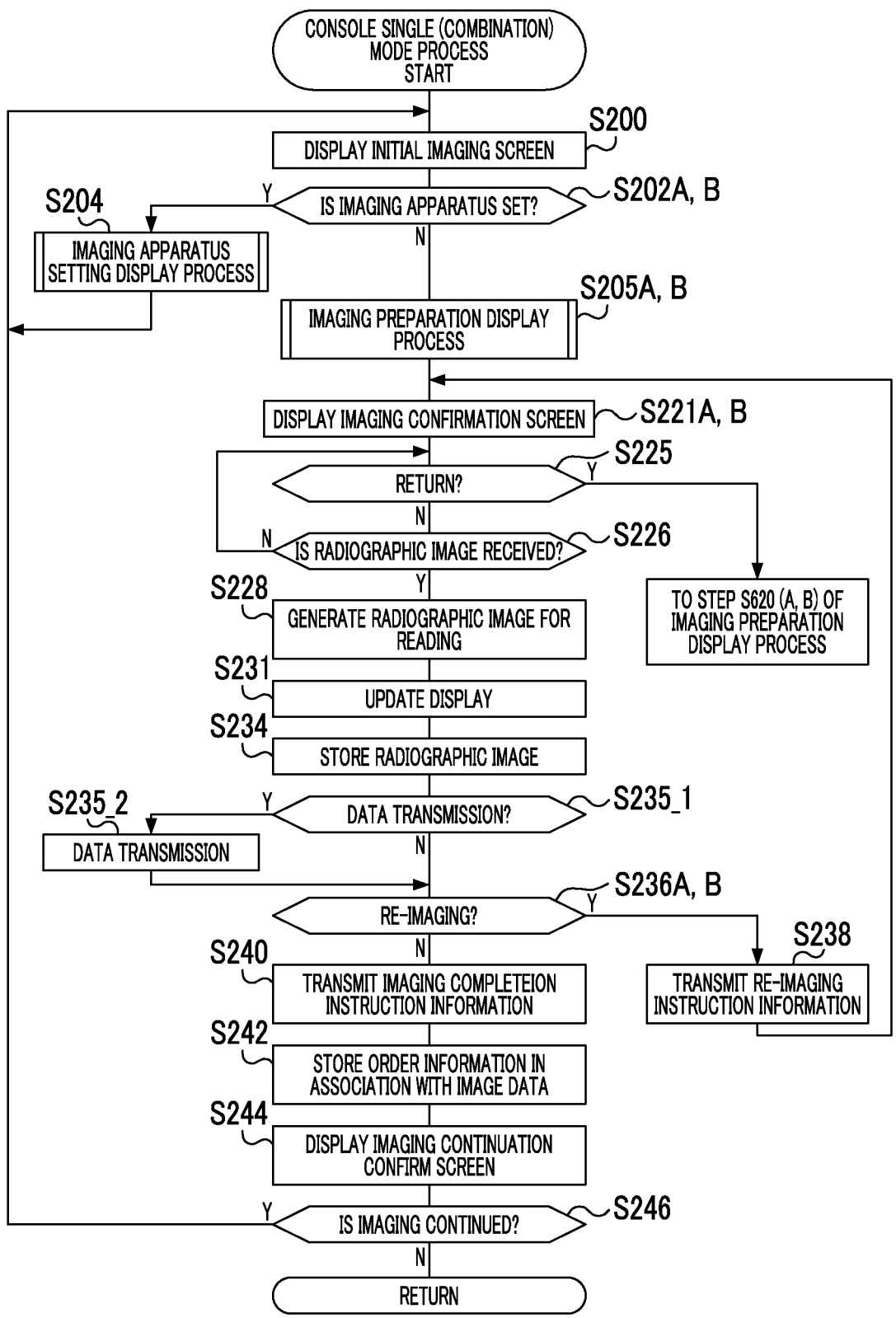
FIG. 42 is a flowchart illustrating an example of a flow of a console single mode process and a console combination mode process executed by a control unit of a console of the second embodiment.

The console single mode process of this embodiment will be described. FIG. 42 is a flowchart illustrating an example of a flow of a console single mode process executed by the control unit 50 of the console 18 of this embodiment.

As shown in FIG. 42, the console single mode process of this embodiment is different from the console single mode process (see FIGS. 5A and 5B) of the first embodiment in that steps S205A, S221A, and S225 are executed instead of the processes of steps S206A to S224.

In step S200 of the console single mode process of this embodiment, the control unit 50 causes the display 56 to display an initial imaging screen.

Figure 43:
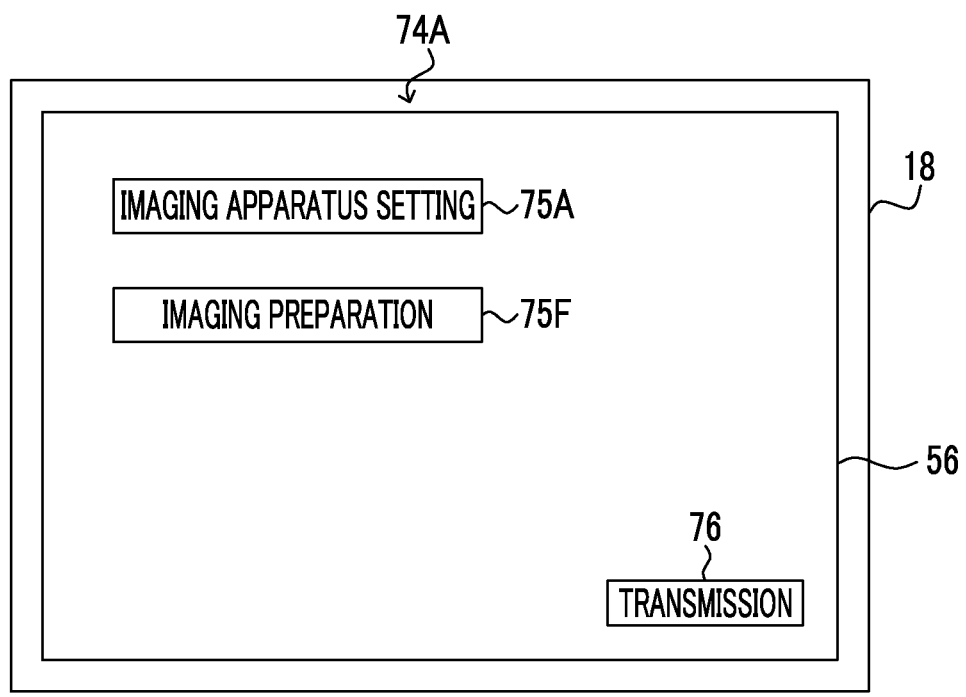
FIG. 43 is a schematic diagram showing a specific example in a state where an initial imaging screen is displayed on a display of the console.

FIG. 43 is a schematic diagram showing a specific example in a state where an initial imaging screen 74A is displayed on the display 56 of the console 18 in this embodiment. As shown in FIG. 43, the initial imaging screen 74A of this embodiment is different from the initial imaging screen 74 (see FIG. 6) of the first embodiment in that a select button 75F is displayed instead of the select buttons 75B to 75E.

The select button 75F is a button selected by a user in the case of imaging preparation. In a case where the control unit 50 detects that "imaging preparation" is selected by selecting the select button 75F by the user, the determination is negative in step S202A, and then, the procedure proceeds to step S205A.

Figure 44:
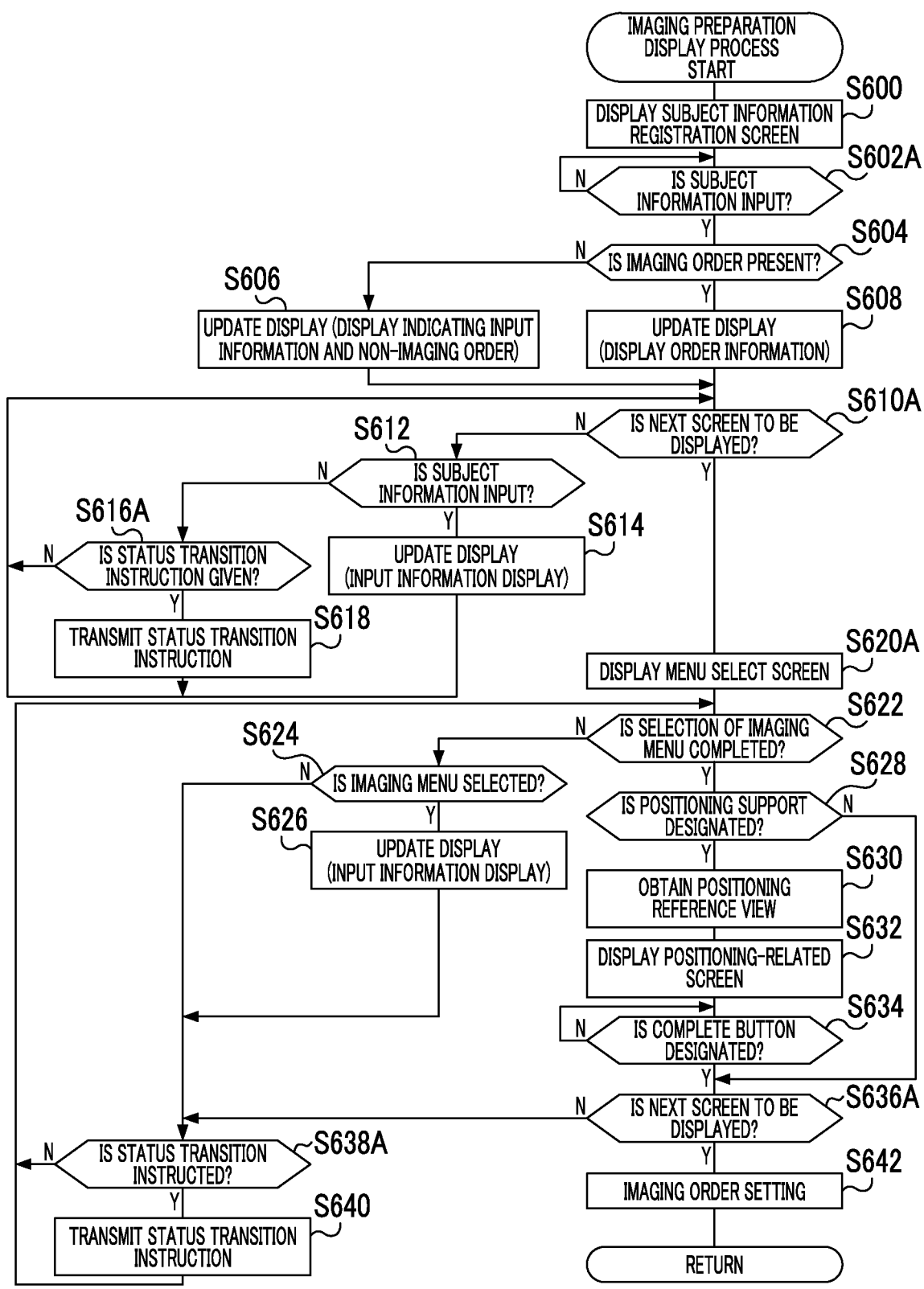
FIG. 44 is a flowchart showing an example of a flow of an imaging preparation display process in the console single mode process executed by the control unit of the console of the second embodiment.

In the radiographic imaging system 10 of this embodiment, in a case where the user selects the select button 75F, an imaging preparation display process shown in FIG. 44 is performed. If the imaging preparation display process is completed, imaging of a radiographic image is subsequently performed. Thus, in step S205A, the control unit 50 executes the imaging preparation display process shown in FIG. 44.

In step S600 in FIG. 44, the control unit 50 causes the display 56 to display a subject information registration screen. Specifically, the control unit 50 generates the subject information registration screen using information relating to the subject information registration screen stored in the storage unit 52, and causes the display 56 to display the subject information registration screen.

Figure 45:
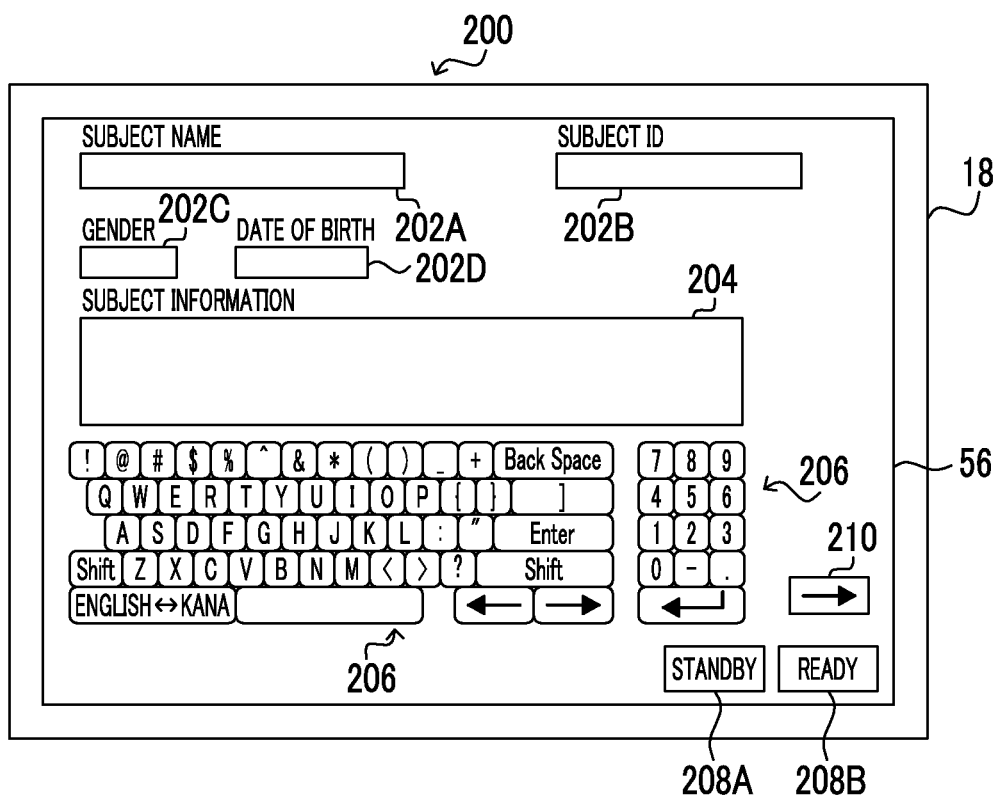
FIG. 45 is a schematic diagram showing a specific example of a state where a subject information registration screen is displayed on the display of the console.

FIG. 45 is a schematic diagram showing a specific example of a state where a subject information registration screen 200 is displayed on the display 56 of the console 18. Display for performing registration of information regarding a subject W by a user is performed on the subject information registration screen 200 of this embodiment.

A display region 202A for displaying a subject name as information for identifying the subject W, a display region 202B for displaying a subject ID (identification), a display region 202C for displaying a gender, and a display region 202D for displaying the date of birth are provided on the subject information registration screen 200 shown in FIG. 45.

Further, a display region 204 for displaying detailed information (subject information) relating to the subject W is provided on the subject information registration screen 200. The subject information displayed in the display region 204 is not particularly limited, but for example, may include so-called patient information such as a gender, weight and height of the subject W, the presence or absence of allergy of the subject, and a side-effect due to a contrast medium.

Further, an input unit 206 is displayed on the subject information registration screen 200. In the console 18 of this embodiment, it is possible to register information regarding the subject W by operating the input unit 206 displayed on the display 56 by a user. All of the subject name, the subject ID, the gender, and the date of birth may not be registered, but at least one of the subject name or the subject ID is registered.

Thus, in the next step S602A, the control unit 50 determines whether information regarding the subject W is input. Specifically, the control unit 50 determines whether it is detected that the input unit 206 is operated. The control unit 50 waits until the information regarding the subject W is input. If the information regarding the subject W is input, the determination is affirmative, and then, the procedure proceeds to step S604A.

In step S604A, the control unit 50 determines whether an imaging order corresponding to an input subject name or subject ID is present. Specifically, the control unit 50 determines whether the imaging order corresponding to the input subject name or subject ID is present in existing imaging orders stored in the storage unit 52. In a case where the imaging order is not present, the determination is negative, and then, the procedure proceeds to step S606.

Figure 46:
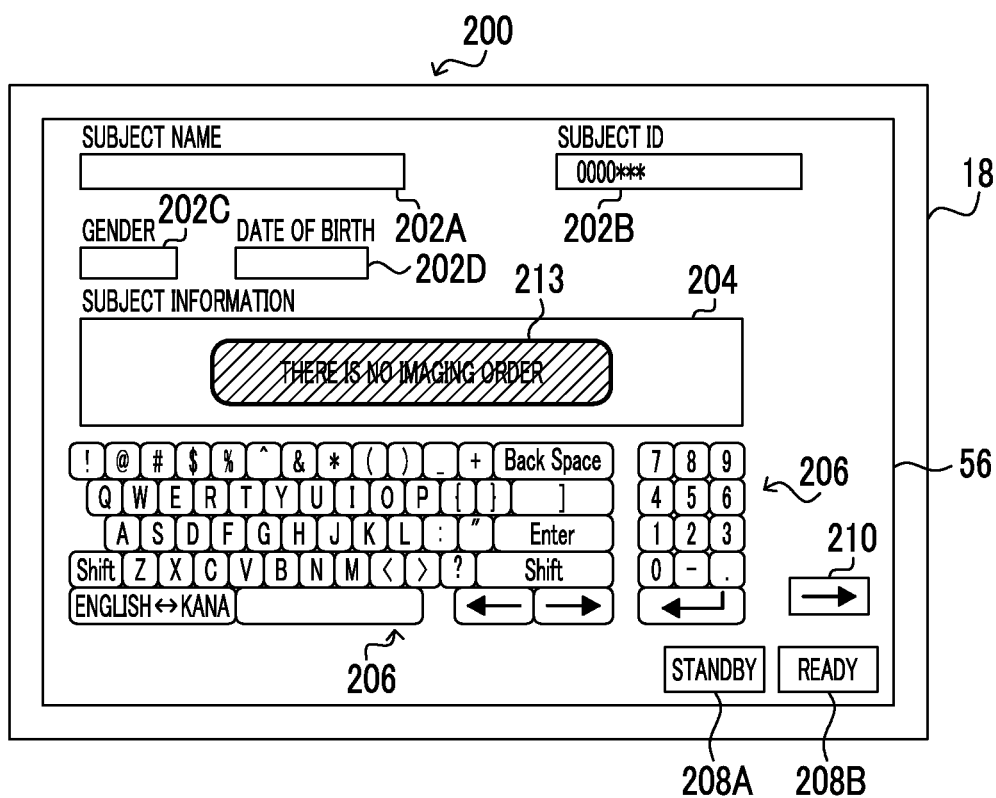
FIG. 46 is a schematic diagram showing a specific example of a state where information indicating that an imaging order is not present is displayed on the subject information registration screen.

In step S606, the control unit 50 updates the display of the subject information registration screen 200, displays information regarding a subject W input through the input unit 206 from a user and information indicating that the imaging order is not present on the subject information registration screen 200, and then, the procedure proceeds to step S610A. For example, in a case where the user inputs a subject ID through the input unit 206, specifically, the control unit 50 displays the subject ID input by the user in the display region 202B on the subject information registration screen 200 as shown in FIG. 46, and displays information 213 indicating that the imaging order is not present on the subject information registration screen 200.

On the other hand, in a case where the imaging order is present, the determination is affirmative in step S604A, and then, the procedure proceeds to step S608. In this case, the control unit 50 acquires order information regarding the imaging order corresponding to the input subject name or subject ID.

Figure 47:
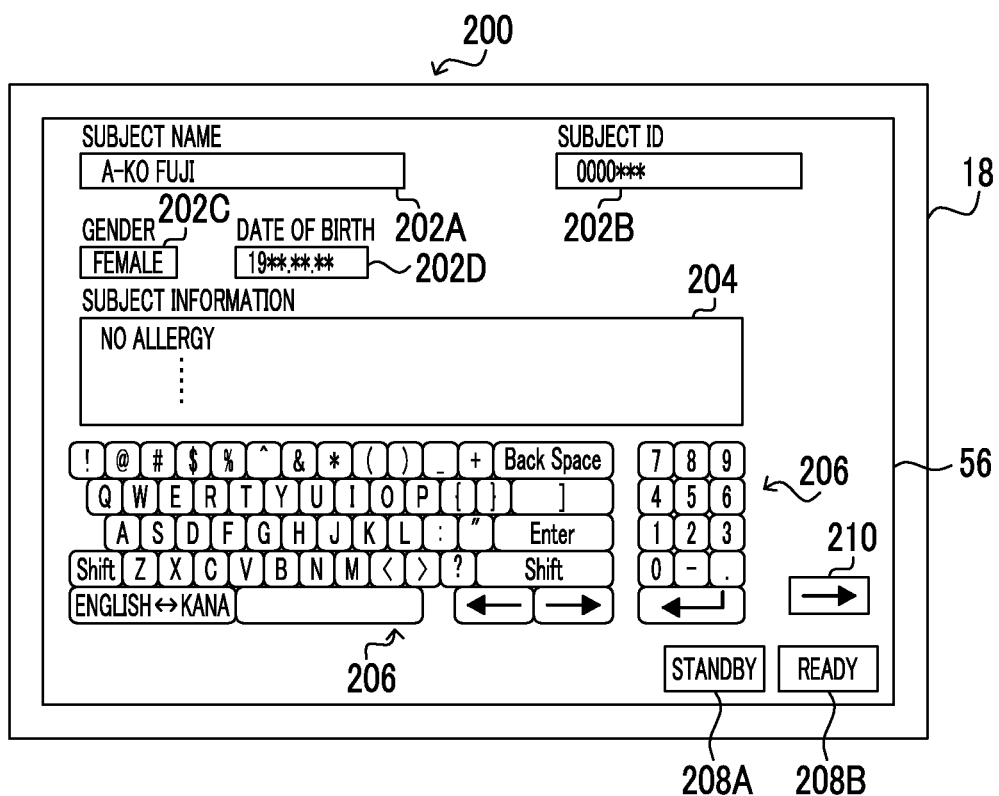
FIG. 47 is a schematic diagram showing a specific example of a state where imaging order information is displayed on the subject information registration screen.

In step S608, the control unit 50 updates the display of the subject information registration screen 200, displays the acquired order information on the subject information registration screen 200, and then, the procedure proceeds to step S610A. Specifically, the control unit 50 displays the subject name in the display region 202A as shown in FIG. 47, displays the subject ID in the display region 202B, displays a gender thereof in the display region 202C, and displays the date of birth thereof in the display region 202D, and then, displays detailed information relating to the subject in the display region 204.

If the display of the subject information registration screen 200 is updated in this way, in step S610A, the control unit 50 determines whether to display the next screen (a menu select screen 220A, see FIG. 48, details of which will be described later). In the console 18 of this embodiment, in a case where registration of the information regarding the subject W is completed, the user operates the instruction button 210 displayed on the subject information registration screen 200. In a case where the instruction button 210 is not operated, the determination is negative, and then, the procedure proceeds to step S612.

In step S612, the control unit 50 determines whether the information regarding the subject W is input, similar to step S602A. For example, in a case where the imaging order is not present, there is a case where a user inputs information regarding a subject W other than the information (in FIG. 47, subject ID) about the subject W which is currently displayed on the subject information registration screen 200 through the input unit 206. Further, for example, even in a case where the imaging order is present, there is a case where the information regarding the subject W that is currently displayed on the subject information registration screen 200 is corrected.

In a case where the information regarding the subject W is input, the determination is affirmative, and then, the procedure proceeds to step S614. In step S614, the control unit 50 updates the display of the subject information registration screen 200 and displays the information regarding the input subject W (input information), and then, the procedure proceeds to step S610A. Similar to step S604A, it is preferable that the presence or absence of the imaging order is determined and the display of the subject information registration screen 200 is updated according to the determination result.

In a case where the information regarding the subject W is not input, the determination is negative, and then, the procedure proceeds to step S616A. In step S616A, the control unit 50 determines whether an instruction for status transition is present. In this embodiment, for example, as shown in FIG. 45, instruction buttons 208A and 208B for instructing the radiographic imaging apparatus 14 to perform the status transition are displayed on the subject information registration screen 200.

The instruction button 208A is a button selected by a user in a case where the user gives an instruction for causing the radiographic imaging apparatus 14 to transition to a standby state. The instruction button 208B is a button selected by a user in a case where the user gives an instruction for causing the radiographic imaging apparatus 14 to transition to a ready state. In a case where the control unit 50 detects that any one of the instruction buttons 208A and 208B is selected for the instruction of the user, the determination is affirmative, and then, the procedure proceeds to step S618.

In step S618, the control unit 50 transmits a status transition instruction to the radiographic imaging apparatus 14 according to the detected instruction button 208A or 208B, and then, the procedure proceeds to step S610A. The terminal control unit 30 of the radiographic imaging apparatus 14 causes the state of the radiographic imaging apparatus 14 to become any one of the standby state and the ready state according to the received status transition instruction. Since the console 18 of this embodiment can recognize the status of the radiographic imaging apparatus 14 in the portable information terminal 16, the status transition instruction is also transmitted to the portable information terminal 16.

On the other hand, in a case where any one of the instruction buttons 208A and 208B is not selected for the instruction of a user, the determination is negative in step S616A, and then, the procedure proceeds to step S610A.

If the determination is affirmative in step S610A, the procedure proceeds to step S620A.

In step S620A, the control unit 50 causes the display 56 to display a menu select screen instead of the subject information registration screen 200. Specifically, the control unit 50 generates a menu select screen using information relating to a menu select screen stored in the storage unit 52, and causes the display 56 to display the generated menu select screen.

Figure 48:
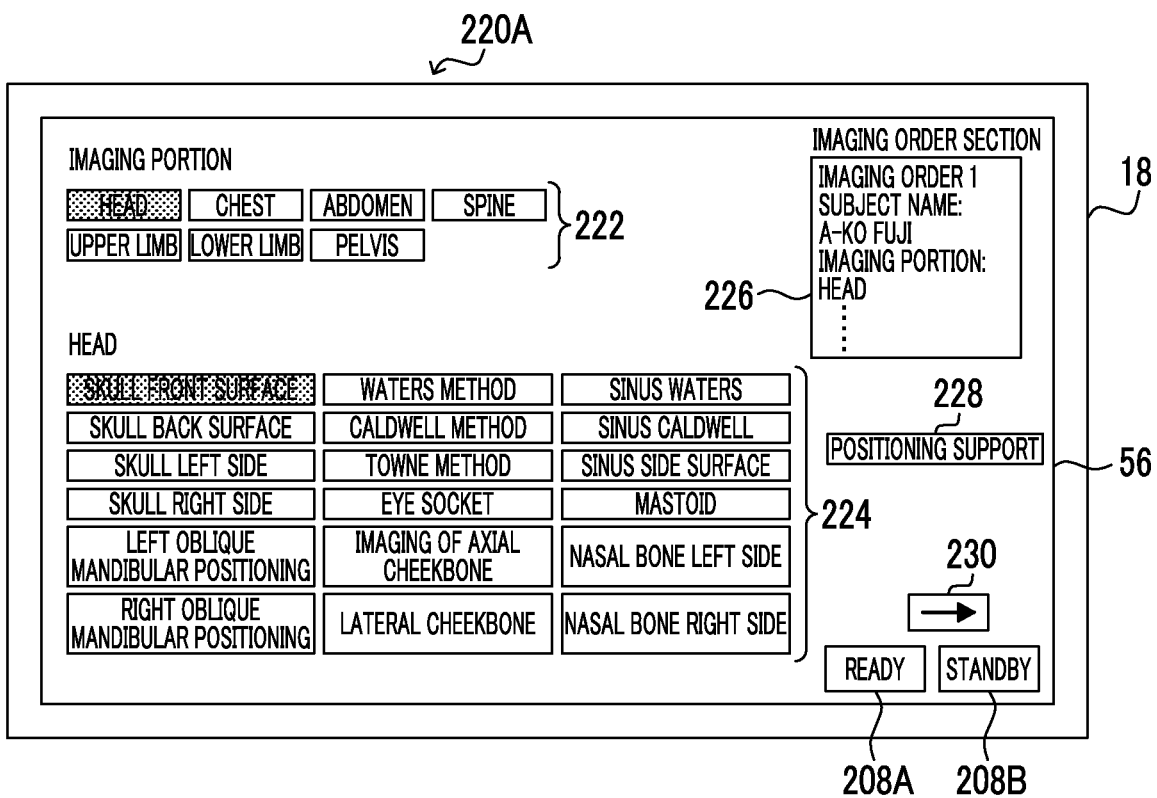
FIG. 48 is a schematic diagram showing a specific example of a state where a menu select screen is displayed on the display of the console.

FIG. 48 is a schematic diagram showing a specific example of a state where a menu select screen 220A is displayed on the display 56 of the console 18. Display for performing selection of an imaging menu of a radiographic image by a user is performed on the menu select screen 220A of this embodiment. In this embodiment, the imaging menu refers to the type of imaging, an imaging method, or the like.

A plurality of select buttons 222 for selecting an imaging portion of a subject W and a plurality of select buttons 224 for selecting an imaging menu according to the imaging portion selected by each select button 222 are displayed on the menu select screen 220A shown in FIG. 48. In a case where the imaging portion is not selected on the menu select screen 220A of this embodiment, the select button 224 is not displayed.

In a case where order information is completely acquired when the menu select screen 220A is displayed in step S620A, specifically, in a case where the process of step S608 is performed, the acquired order information is displayed on the menu select screen 220A. The select button 224 in FIG. 48 shows a display example in which an imaging portion included in the acquired order information corresponds to a "head portion" and an imaging menu corresponds to a "skull front" as a specific example. In the specific example shown in FIG. 48, a color of a select button corresponding to the "head portion" among the select buttons 222 and a color of a select button corresponding to the "skull front" among the select buttons 224 are set to be different from each other.

Further, the imaging order is displayed in a display region 226 of the menu select screen 220A. FIG. 48 shows the acquired imaging order as described above.

In a case where the order information is not acquired when the menu select screen 220A is displayed in step S620A, since the imaging portion is not selected, as described above, the select button 224 is not displayed on the menu select screen 220A, differently from the specific example of FIG. 48. The currently determined imaging order, specifically, information regarding the subject W registered on the subject information registration screen 200 is displayed in the display region 226.

In the next step S622A, the control unit 50 determines whether selection of an imaging menu is completed.

As described above, in a case where the imaging portion and the imaging menu are included in the acquired order information, the control unit 50 determines whether the imaging menu is selected. Further, in a case where the control unit 50 detects that a user selects the imaging menu using the select button 222 and the select button 224, similarly, it is determined that the imaging menu is selected. In cases other these cases, the control unit 50 determines that the imaging menu is not selected. In a case where the imaging menu is not selected, the determination is negative, and then, the procedure proceeds to step S624A.

In step S624A, the control unit 50 determines whether the imaging menu is selected. Specifically, in a case where the control unit 50 detects that the select button 222 and the select button 224 are operated, it is determined that the imaging menu is selected. In a case where the imaging menu is selected, the determination is affirmative, and then, the procedure proceeds to step S626A. In step S626A, the control unit 50 updates the display of the menu select screen 220A and displays the input imaging menu (input information) to be recognizable, and then, the procedure proceeds to step S638A. Further, in a case where the determination is negative in step S624A, similarly, the procedure proceeds to step S638A.

In step S638A, the control unit 50 determines whether an instruction for status transition is present, similar to step S616A. In this embodiment, for example, as shown in FIG. 48, instruction buttons 208A and 208B for instructing the radiographic imaging apparatus 14 to perform the status transition are displayed on the menu select screen 220A, similar to the subject information registration screen 200.

In a case where the control unit 50 detects that any one of the instruction buttons 208A and 208B is used for the instruction of the user, the determination is affirmative, and then, the procedure proceeds to step S640.

In step S640, the control unit 50 transmits a status transition instruction to the radiographic imaging apparatus 14 according to the detected instruction button 208A or 208B, similar to step S618, and then, the procedure returns to step S622. On the other hand, in a case where any one of the instruction buttons 208A and 208B is not used for the instruction of the user, the determination is negative in step S638A, and then, the procedure returns to step S622.

If the imaging menu is selected, the determination is affirmative in step S622, and then, the procedure proceeds to step S628.

In step S628, the control unit 50 determines whether a positioning support button 228 displayed on the menu select screen 220A is designated. In a case where the control unit 50 does not detect that the positioning support button 228 is designated, the determination is negative, and then, the procedure proceeds to step S636A.

On the other hand, in a case where the control unit 50 detects that the positioning support button 228 is designated, the determination is affirmative in step S628, and then, the procedure proceeds to step S630. In a case where the positioning support button 228 is designated, in this embodiment, similar to the positioning related display process (see FIG. 5A and FIG. 17) in step S216 of the console single mode process in the first embodiment, in step S630, the control unit 50 acquires image data of reference views for positioning of a subject W by a user based on acquired order information, from the storage unit 52.

In the next step S632, the control unit 50 causes the display 56 to display a positioning related screen. Specifically, the control unit 50 causes the display 56 to display a positioning related screen 100 shown in FIG. 18.

In the next step S634, the control unit 50 determines whether the complete button 104 is designated, and waits until the control unit 50 detects that the complete button 104 is designated. If the control unit 50 detects that the complete button 104 is designated, the determination is affirmative, and then, the procedure proceeds to step S636A.

In step S636A, the control unit 50 determines whether to display the next screen (imaging confirmation screen 240A, see FIG. 49, details of which will be described later). In the console 18 of this embodiment, in a case where selection of an imaging menu is completed, a user operates an instruction button 230 displayed on the menu select screen 220A. In a case where the instruction button 230 is not operated, the determination is negative, and then, the procedure proceeds to step S638A. On the other hand, in a case where the instruction button 230 is operated, the determination is affirmative, and then, the procedure proceeds to step S642.

In step S642, the control unit 50 sets the imaging order based on the process as an imaging order used for imaging, and then, terminates the imaging preparation display process. Thereafter, the procedure proceeds to step S221A of the console single mode process. Thereafter, imaging of a radiographic image is performed on the basis of the set imaging order in the imaging preparation display process.

In step S221A, the control unit 50 causes the display 56 to display an imaging confirmation screen instead of the menu select screen 220A. Specifically, the control unit 50 generates an imaging confirmation screen using information relating to the imaging confirmation screen stored in the storage unit 52, and causes the display 56 to display the generated imaging confirmation screen.

Figure 49:
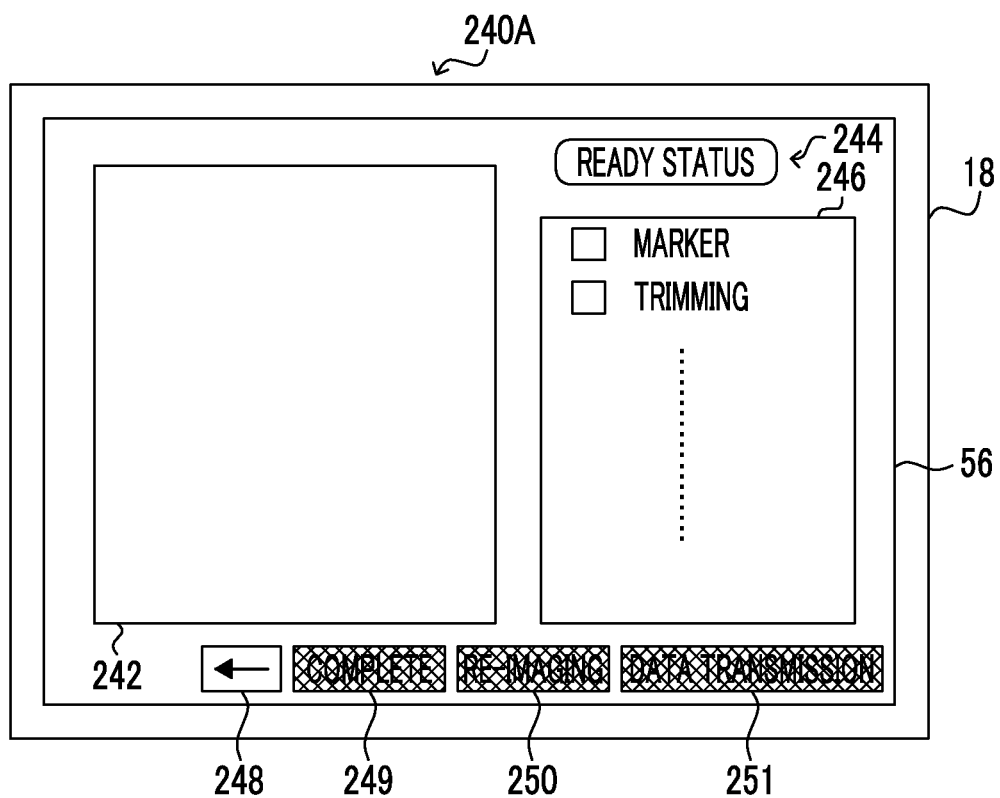
FIG. 49 is a schematic diagram illustrating a specific example of a state where an imaging confirmation screen is displayed on the display of the console.

FIG. 49 is a schematic diagram illustrating a specific example of a state where an imaging confirmation screen 240A is displayed on the display 56 of the console 18. As shown in FIG. 49, a display region 242 for displaying a captured radiographic image is provided on the imaging confirmation screen 240A in this embodiment. Since a radiographic image is not yet captured when the imaging confirmation screen 240A is originally displayed on the display 56, the radiographic image is not yet displayed in the display region 242.

Further, information 244 indicating a current state (status) of the portable information terminal 16, an image treatment process select button 246, an instruction button 248, a complete button 249, a re-imaging button 250, and a data transmission button 251 are displayed on the imaging confirmation screen 240A.

The image treatment process select button 246 is a button for selecting image processing to be performed with respect to a radiographic image. The image processing to be performed with respect to the radiographic image is not particularly limited, and for example, may include a process of writing a mark into a radiographic image (see "mark" in FIG. 49), a trimming process (see "trimming" in FIG. 49), or the like. In this embodiment, if a user selects the image treatment process select button 246 corresponding to a desired treatment process from a plurality of image treatment processes, the control unit 50 performs an image treatment process based on the selection with respect to a radiographic image, and displays the radiographic image after the image treatment process in the display region 242.

The instruction button 248 is a button selected by a user in a case where the user gives an instruction for returning an image to be displayed to the image displayed before the image treatment process. The complete button 249 is a button selected by a user in a case where the user instructs completion of imaging of a radiographic image. Further, the re-imaging button 250 is a button selected by a user in a case where the user executes re-imaging. In addition, the data transmission button 251 is a button selected by a user in a case where the user gives an instruction for transmitting image data of a radiographic image to a predetermined device (for example, an external server, or the like) from the console 18. In this embodiment, since imaging of a radiographic image is not yet performed when the imaging confirmation screen 240A is originally displayed on the display 56, although the complete button 249, the re-imaging button 250, and the data transmission button 251 are displayed on the imaging confirmation screen 240A, an instruction from the user is not possible.

In the next step S225, the control unit 50 determines whether to return a screen to be displayed on the display 56 to the previous screen, that is, the display of the menu select screen 220A. In a case where the control unit 50 detects that the instruction button 248 is used for instruction, the determination is affirmative, and then, the procedure proceeds to step S620A (see FIG. 44) of the above-described imaging preparation display process. On the other hand, in a case where the control unit 50 does not detect that the instruction button 248 is used for instruction, the determination is negative, and then, the procedure proceeds to step S226.

In step S226, the control unit 50 determines whether image data of a radiographic image is received. In a case where the image data is not received, the determination is negative, and then, the procedure returns to step S225. In a case where the image data is received, the procedure proceeds to step S228.

Further, as shown in FIG. 42, the console single mode process of this embodiment is different from the console single mode process (see FIG. 5B) of the first embodiment in that the process of step S231 is executed instead of step S230.

Figure 50:
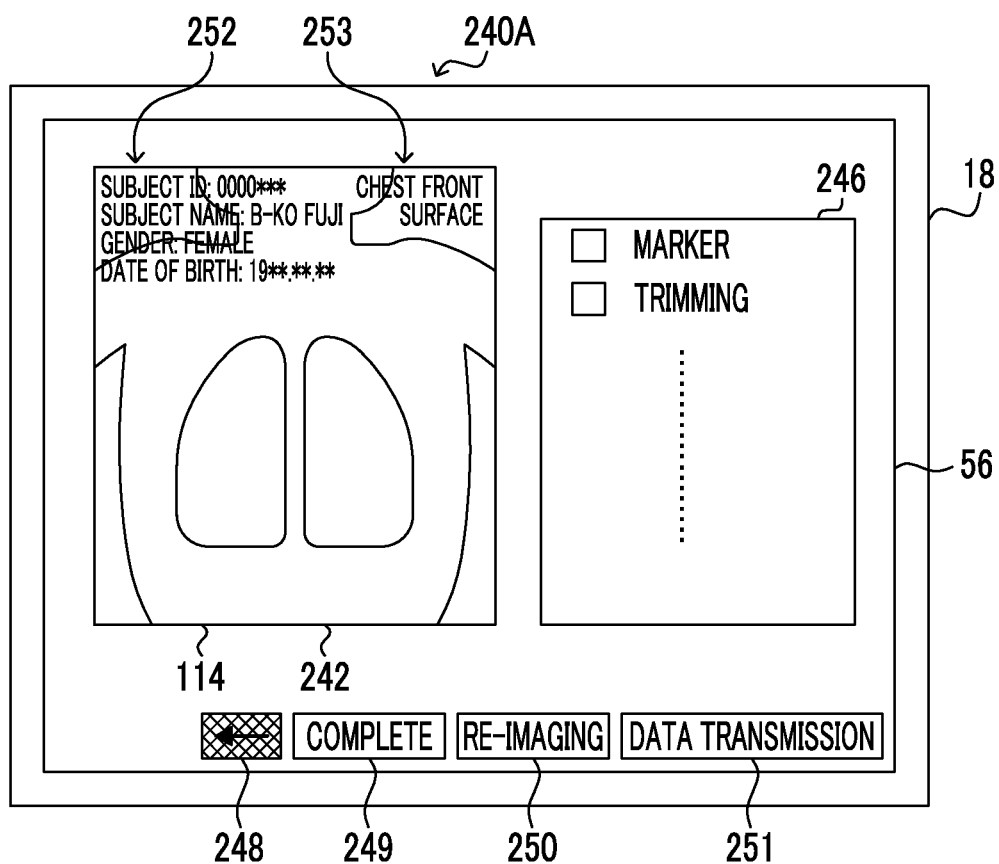
FIG. 50 is a schematic diagram illustrating a specific example of a state of the imaging confirmation screen displayed on the display of the console after imaging of a radiographic image.

In step S231, the control unit 50 updates the imaging confirmation screen 240A displayed on the display 56. In this embodiment, as a specific example, as shown in FIG. 50, the radiographic image 114 for reading generated in step S228 is displayed in the display region 242. Further, information 252 of a subject acquired from order information, information 253 of an imaging menu, or the like, is displayed at a location that does not disturb reading, such as four corners of the radiographic image 114 for reading. In addition, an instruction of the instruction button 248 becomes impossible, and instructions of the complete button 249, the re-imaging button 250, and the data transmission button 251 become possible.

In a case where the image treatment process select button 246 is selected by a user in a state where the radiographic image 114 for reading is displayed, the control unit 50 performs an image treatment process based on the selected button with respect to a radiographic image. Further, the control unit 50 updates the radiographic image 114 for reading displayed in the display region 242.

In addition, as shown in FIG. 42, the console single mode process of this embodiment is different from the console single mode process (see FIG. 5B) of the first embodiment in that processes of steps S235_1 and S235_2 are executed between step S234 and step S236A.

In step S235_1 of the console single mode process of the embodiment, the control unit 50 determines whether to transmit image data of a radiographic image. In a case where the control unit 50 detects that data transmission button 251 is used for instruction, the determination is affirmative, and then, the procedure proceeds to step S235_2. In step S235_2, the control unit 50 transmits the image data of the radiographic image to a predetermined device, and then, the procedure proceeds to step S236A. Further, in a case where the control unit 50 does not detect that the data transmission button 251 is used for instruction, the determination is negative, and then, the procedure proceeds to step S236A.

In step S236A, the control unit 50 determines whether to perform re-imaging. In a case where the control unit 50 detects that the re-imaging button 250 is used for instruction, the determination is affirmative, and then, the procedure proceeds to step S238. On the other hand, in a case where the control unit 50 detects that the complete button 249 is used for instruction, the determination is negative, and then, the procedure proceeds to step S240.

Next, a console combination mode process in step S108 (see FIG. 3) of the console process, executed in the console 18 of this embodiment will be described.

In the console combination mode process of the console 18 of this embodiment, similar to the console combination mode process of the console 18 of the first embodiment, in a case where a user receives a designated content signal indicating content designated on a screen displayed on the display 36 of the portable information terminal 16, the control unit 50 performs the same process as in a case where the user performs designation through the operation unit 60 of the host device.

Figure 51:
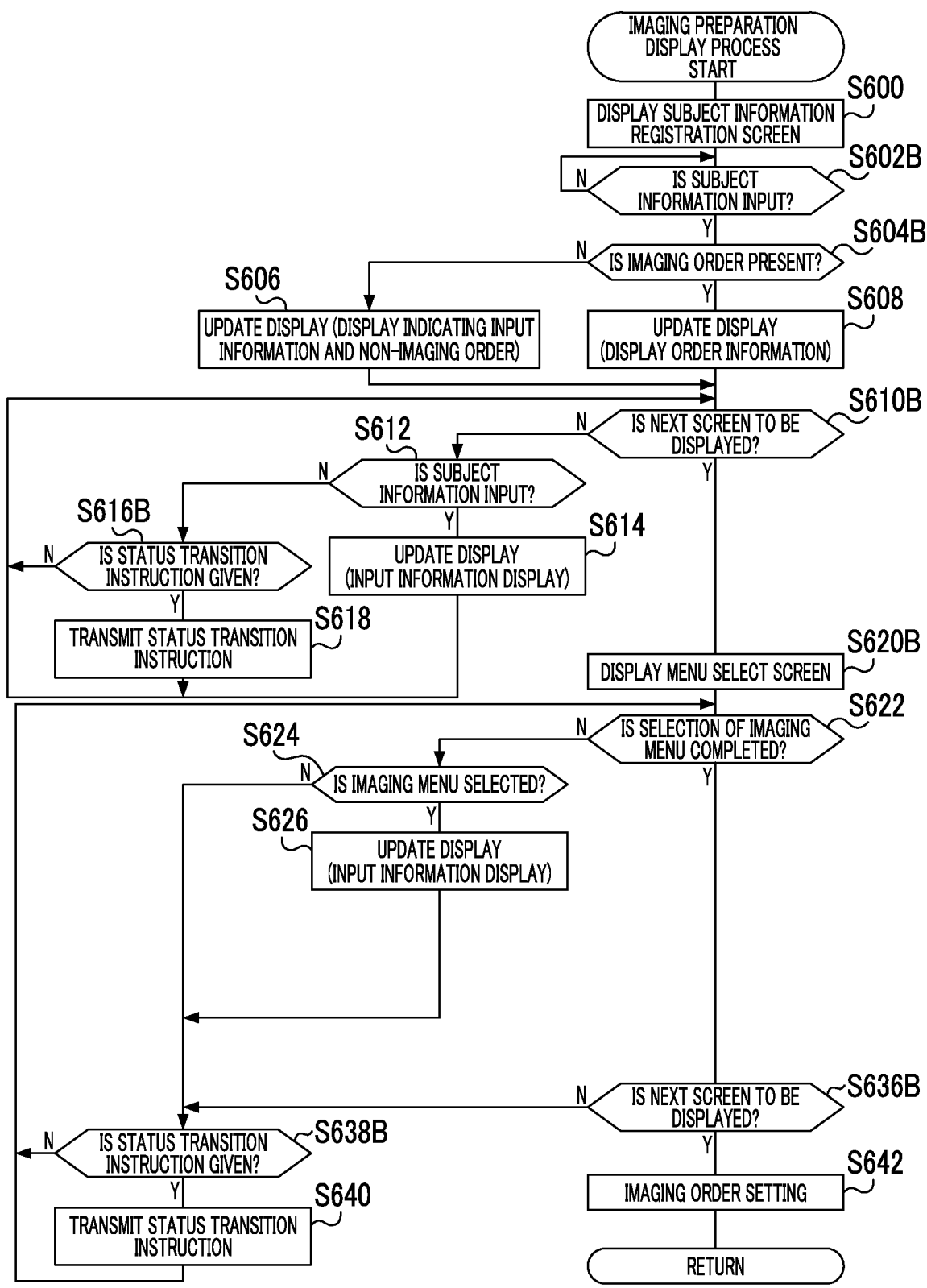
FIG. 51 is a flowchart illustrating an example of a flow of the imaging preparation display process in the console combination mode process executed by the control unit of the console of the second embodiment.

As shown in FIG. 42, in the console combination mode process of this embodiment, step S205B is executed instead of step S205A of the console single mode process. As shown in FIG. 51, the imaging preparation display process of the console combination mode process is partly different from the console single mode process (see FIG. 44).

As shown in FIG. 51, in the imaging preparation process of this embodiment, in step S602B, the control unit 50 determines whether information regarding a subject W is received from the portable information terminal 16 or the information regarding the subject W is input.

In step S604B, the control unit 50 determines whether an imaging order corresponding to a received subject W information or an input subject name or an input subject ID is present. In a case where there is no imaging order, the determination is negative, and then, the procedure proceeds to step S606. Further, the control unit 50 transmits a message indicating that there is no imaging order to the portable information terminal 16. On the other hand, in a case where there is the imaging order, the determination is affirmative in step S604B, and then, the procedure proceeds to step S608. In addition, the control unit 50 transmits the imaging order to the portable information terminal 16.

Further, in step S610B, the control unit 50 determines whether the next screen is to be displayed on the basis of the designated content signal received from the portable information terminal 16 or a detection result of an operation of the instruction button 210 displayed on the subject information registration screen 200. In a case where the operation of the instruction button 210 is detected, the control unit 50 transmits a designated content signal indicating that the next screen is to be displayed to the portable information terminal 16.

Further, in step S616B, the control unit 50 determines whether status transition is instructed, on the basis of the designated content signal received from the portable information terminal 16 or the detection result of the operation of the instruction buttons 208A and 208B displayed on the subject information registration screen 200. In a case where the operation of the instruction button 208A or 208B is detected, the control unit 50 transmits the designated content signal indicating a status based on the operation to the portable information terminal 16.

Figure 52:
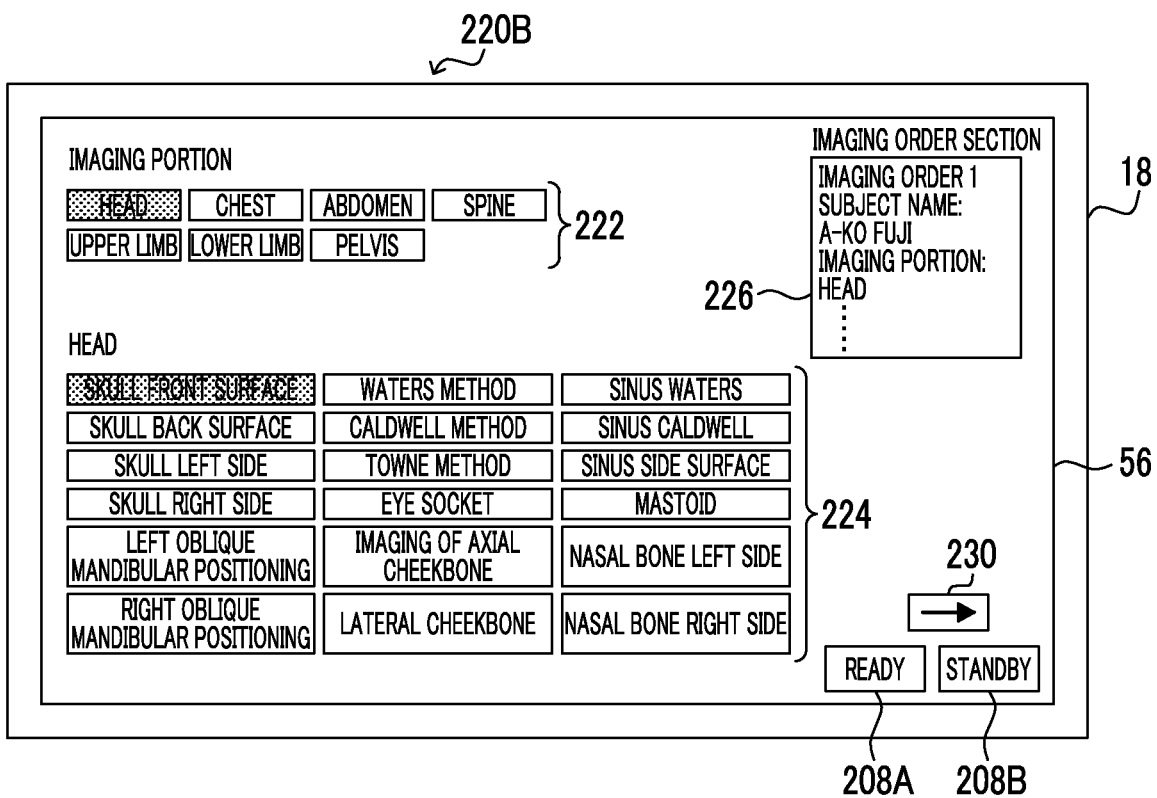
FIG. 52 is a schematic diagram illustrating a specific example of a state where a menu select screen is displayed on the display of the console.

In addition, in step S620B, the control unit 50 causes the display 56 to display a menu select screen 220B shown in FIG. 52, instead of the subject information registration screen 200. In this embodiment, in the case of the console combination mode, the console 18 does not perform display relating to support of positioning. Thus, as shown in FIG. 52, the menu select screen 220B is different from the menu select screen 220A (see FIG. 48) in that the positioning support button 228 is not displayed.

Further, since the display relating to support of positioning is not performed, the processes of steps S628 to S634 of the imaging preparation display process (see FIG. 44) in the console single mode process are not performed, and the determination is affirmative in step S622, the procedure proceeds to step S636B.

In step S636B, the control unit 50 determines whether the next screen is to be displayed on the basis of the designated content signal received from the portable information terminal 16 or a detection result of an operation of the instruction button 230 displayed on the menu select screen 220A. In a case where the operation of the instruction button 230 is detected, the control unit 50 transmits a designated content signal indicating that the next screen is to be displayed to the portable information terminal 16.

Further, in step S638B, the control unit 50 determines whether status transition is instructed, similar to step S616B.

As shown in FIG. 42, in the console combination mode process of this embodiment, step S221B is executed instead of step S221A of the console single mode process.

Figure 53:
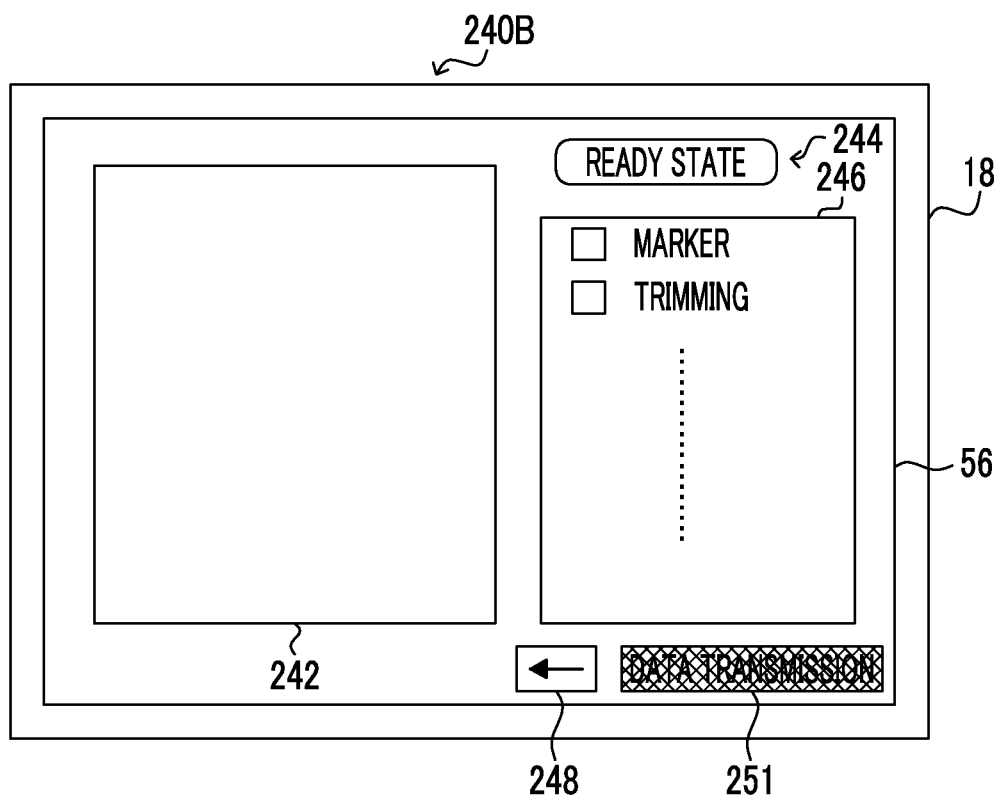
FIG. 53 is a schematic diagram illustrating a specific example of a state where an imaging confirmation screen is displayed on the display of the console.

In step S221B, the control unit 50 causes the display 56 to display an imaging confirmation screen 240B shown in FIG. 53, instead of the imaging confirmation screen 240A. In this embodiment, in the case of the console combination mode, an instruction relating to re-imaging is not performed from the console 18. Thus, as shown in FIG. 53, the imaging confirmation screen 240B is different from the imaging confirmation screen 240A (see FIG. 49) in that the complete button 249 and the re-imaging button 250 are not displayed.

Further, as shown in FIG. 42, in the console combination mode process of this embodiment, step S236B is executed instead of step S236A of the console single mode process.

In step S236B, the control unit 50 determines whether re-imaging is to be performed on the basis of the designated content signal received from the portable information terminal 16.

Next, an operation of the portable information terminal 16 of this embodiment will be described. An overall flow of a terminal process executed by the terminal control unit 30 of the portable information terminal 16 is the same as in the first embodiment (see FIG. 23). In this embodiment, since processing content of the terminal single mode process in step S402 of the terminal process and processing content of the terminal combination mode process in step S408 are different from that of the first embodiment, the respective processes will be described. Various screens displayed on the display 36 of the portable information terminal 16 correspond to various screens having the same names as those displayed on the display 56 of the console 18.

Figure 54:
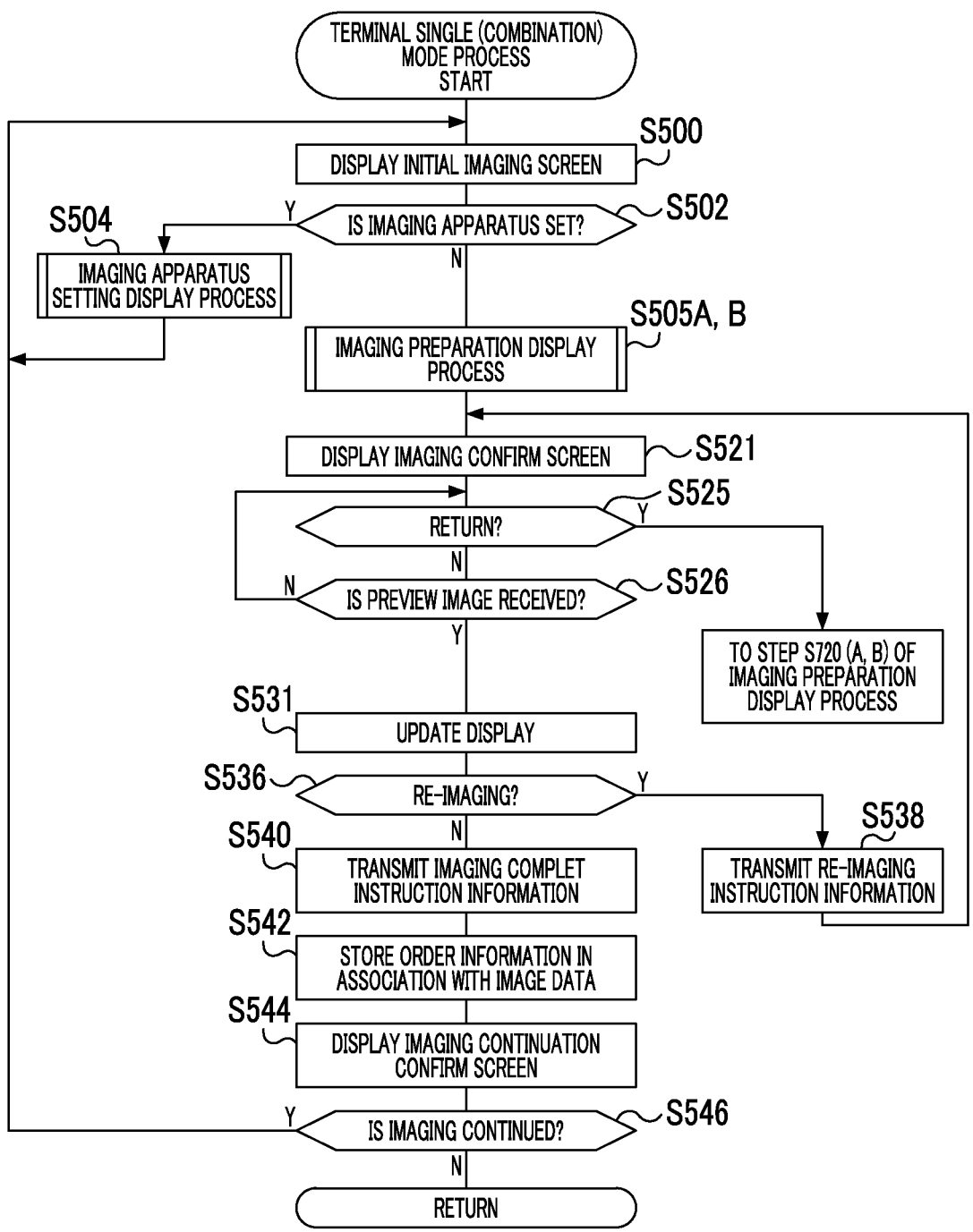
FIG. 54 is a flowchart illustrating an example of a flow of a terminal single mode process executed by a terminal control unit of the portable information terminal of the second embodiment.

The terminal single mode process of this embodiment will be described. FIG. 54 is a flowchart illustrating an example of a flow of a terminal single mode process executed by a terminal control unit 30 of the portable information terminal 16 of this embodiment.

As shown in FIG. 54, the terminal single mode process of this embodiment is different from the terminal single mode process (see FIGS. 25A and 25B) of the first embodiment in that steps S505A, S521, and S525 are executed instead of processes of steps S506 to S524.

In step S500 of the terminal single mode process of this embodiment, the terminal control unit 30 causes the display 36 to display an initial imaging screen.

Figure 55:
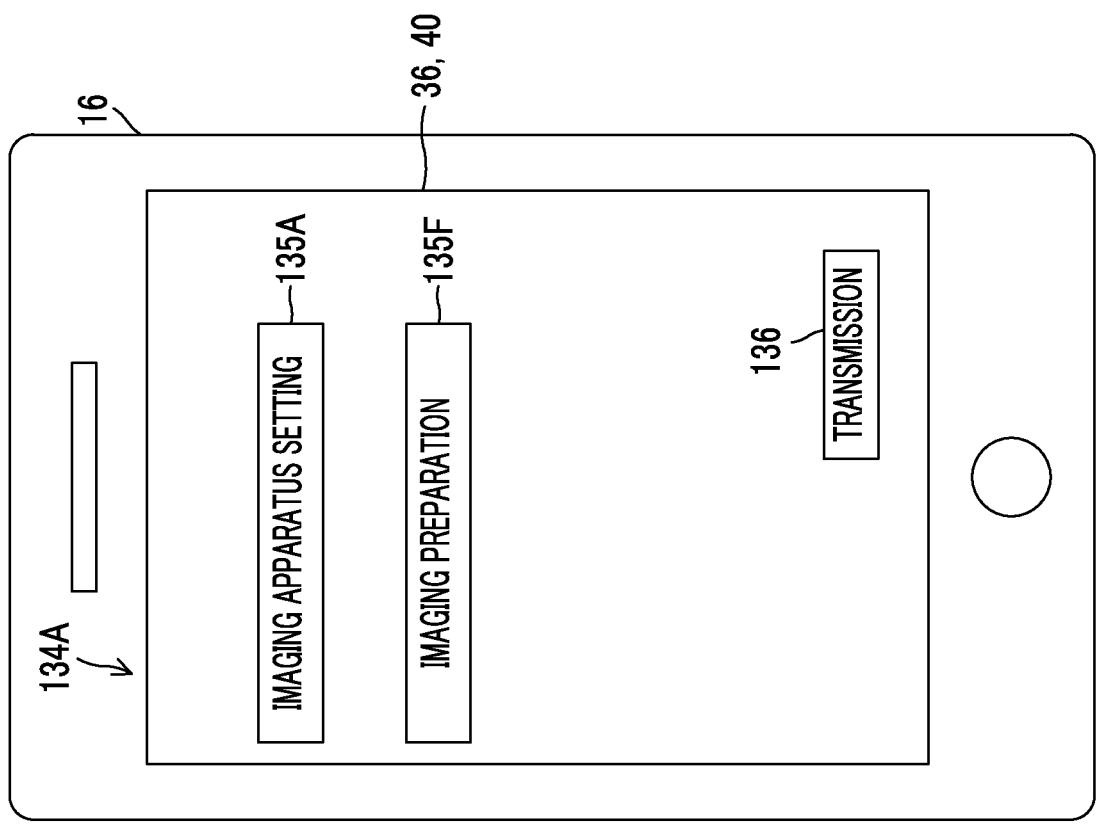
FIG. 55 is a schematic diagram illustrating a specific example of a state where an initial imaging screen is displayed on a display of the portable information terminal.

FIG. 55 is a schematic diagram illustrating a specific example of a state where an initial imaging screen 134A is displayed on the display 36 of the portable information terminal 16 in this embodiment. As shown in FIG. 55, the initial imaging screen 134A in this embodiment is different from the initial imaging screen 134 (see FIG. 26) of the first embodiment in that a select button 135F is displayed instead of the select buttons 135B to 135E.

The select button 135F is a button selected by a user in a case where the user performs imaging preparation. In a case where the terminal control unit 30 detects that the user selects the select button 135F to select the "imaging preparation", the determination is negative in step S502, and then, the procedure proceeds to step S505A.

In the radiographic imaging system 10 of this embodiment, in a case where a user selects the select button 135F, the imaging preparation display process is performed. If the imaging preparation display process is completed, imaging of a radiographic image is continuously performed. Thus, in step S505A, the terminal control unit 30 executes an imaging preparation display process shown in FIG. 56.

In step S700, the control unit 50 causes the display 56 to display a subject information registration screen. Specifically, the control unit 50 generates a subject information registration screen using information relating to the subject information registration screen stored in the storage unit 52, and causes the display 56 to display the generated screen.

Display regions 302A, 302B, 302C, and 302D on a subject information registration screen 300 shown in FIG. 57 respectively correspond to the display regions 202A, 202B, 202C, and 202D on the subject information registration screen 200 (see FIG. 45). Further, a display region 303 and an input unit 306 displayed in the display region 303 respectively correspond to the display region 204 and the input unit 206 on the subject information registration screen 200 (see FIG. 45). If the terminal control unit 30 detects contact of a user to the input unit 306, the terminal control unit 30 enlarges the display of the input unit 306 so that input from the user can be easily performed.

Further, instruction buttons 308A, 308B, and 310 respectively correspond to the instruction buttons 208A, 208B, and 210 of the subject information registration screen 200 (see FIG. 45).

In addition, information 301 for prompting a user to read subject information is displayed on the subject information registration screen 300. In the portable information terminal 16 of this embodiment, in step S702A, the control unit 50 determines whether subject information is input (is read), similar to step S332 (see FIG. 13) of the subject authentication display process of the first embodiment in the portable information terminal 16 of the first embodiment on the basis of the display of the information 301.

In the next step S704A, the terminal control unit 30 determines whether an imaging order corresponding to the read subject information is present, similar to step S334 (see FIG. 13) of the subject authentication display process of the first embodiment.

In a case where there is no imaging order, in step S706, the terminal control unit 30 updates the display of the subject information registration screen 300, displays the read subject information and information indicating that there is no imaging order to the subject information registration screen 300, and then, the procedure proceeds to step S710A. On the other hand, in a case where there is an imaging order, in step S708, the terminal control unit 30 updates the display of the subject information registration screen 300, displays the acquired order information to the subject information registration screen 300, and then, the procedure proceeds to step S710A. Specifically, the terminal control unit 30 displays a subject name in the display region 302A as shown in FIG. 58, displays a subject ID in the display region 302B, displays a gender in the display region 302C, displays the date of birth in the display region 302D, and then, displays detailed information 307 relating to a subject in the display region 303.

In step S710A, the terminal control unit 30 determines whether to display the next screen (menu select screen 320A, see FIG. 59, details of which will be described later). In a case where the next screen is not to be displayed, in step S712, the terminal control unit 30 determines whether to read subject information, similar to step S702A. In a case where the subject information is to be read, in step S714, the terminal control unit 30 updates the display of the subject information registration screen 300, and then, the procedure returns to step S710A. On the other hand, in a case where the subject information is not to be read, in step S716A, the terminal control unit 30 determines whether an instruction for status transition is present. In a case where the instruction for status transition is present through any one of the instruction buttons 308A and 308B, the procedure proceeds to step S718. The terminal control unit 30 transmits the instruction for status transition to the radiographic imaging apparatus 14, and then, the procedure returns to step S710A.

On the other hand, in a case where the next screen is to be displayed, the procedure proceeds to step S720A from step S710A. The terminal control unit 30 causes the display 36 to display the menu select screen 320 displayed in FIG. 59, instead of the subject information registration screen 300.

Figure 59:
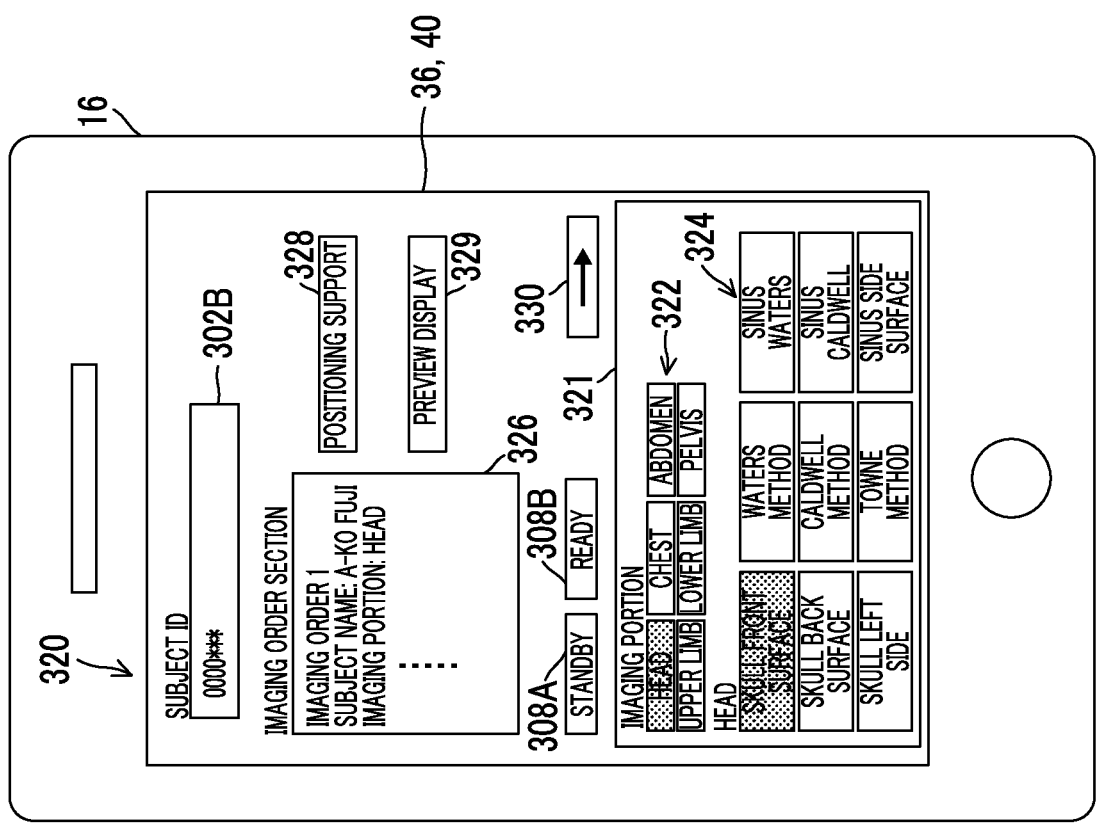
FIG. 59 is a schematic diagram showing a specific example of a state where a menu select screen in the terminal single mode process is displayed on the display of the portable information terminal.

A display region 326 on the menu select screen 320 shown in FIG. 59 corresponds to the display region 226 on the menu select screen 220 (see FIG. 48). Further, instruction buttons 308A and 308B, a positioning support button 328, and an instruction button 330 respectively correspond to the instruction buttons 208A and 208B, the positioning support button 228, and the instruction button 230 on the menu select screen 220 (see FIG. 48).

Further, select buttons 322 and 324 displayed in the display region 321 on the menu select screen 320 correspond to the select buttons 222 and 224 on the menu select screen 220 (see FIG. 48). If the terminal control unit 30 detects contact of a user to the select button 322 or the select button 324, the terminal control unit 30 enlarges the display of the select button 322 or the select button 324 so that input from the user can be easily performed.

In addition, a subject ID of a subject W is displayed in the display region 302B of the menu select screen 320. Further, an instruction button 329 for causing a user to instruct display of a preview image for positioning is displayed on the menu select screen 320.

In the next step S722, the terminal control unit 30 determines whether selection of an imaging menu is completed. In a case where the selection of the imaging menu is not completed, in step S724, the terminal control unit 30 determines whether an imaging menu is selected. Specifically, the terminal control unit 30 determines that the imaging menu is selected in a case where it is detected that the select button 322 and the select button 324 which are enlarged and displayed are operated. Further, in a case where the imaging menu is selected, in step S726, the terminal control unit 30 updates the display of the menu select screen 320 and displays the input imaging menu (input information) to be recognizable, and then, the procedure proceeds to step S738A. Further, even in a case where the imaging menu is not selected, the procedure proceeds to step S738A.

In step S738A, the terminal control unit 30 determines whether an instruction for status transition is present through any one of the instruction buttons 308A and 308B, similar to step S716A. In a case where the instruction for status transition is present, in step S640, the terminal control unit 30 transmits the instruction for status transition to the radiographic imaging apparatus 14, similar to step S718, and then, the procedure returns to step S722. On the other hand, in a case where the instruction for status transition is not present, the procedure proceeds to step S722.

In a case where the selection of the imaging menu is completed, the procedure proceeds to step S728 to step S722. In step S728, the terminal control unit 30 determines whether the positioning support button 328 displayed on the menu select screen 320A is designated.

In a case where the positioning support button 328 is designated, the procedure proceeds to step S730.

In step S730, the terminal control unit 30 causes the user to acquire image data of a reference view for positioning of the subject W from the storage unit 32 on the basis of the acquired order information.

Figure 60:
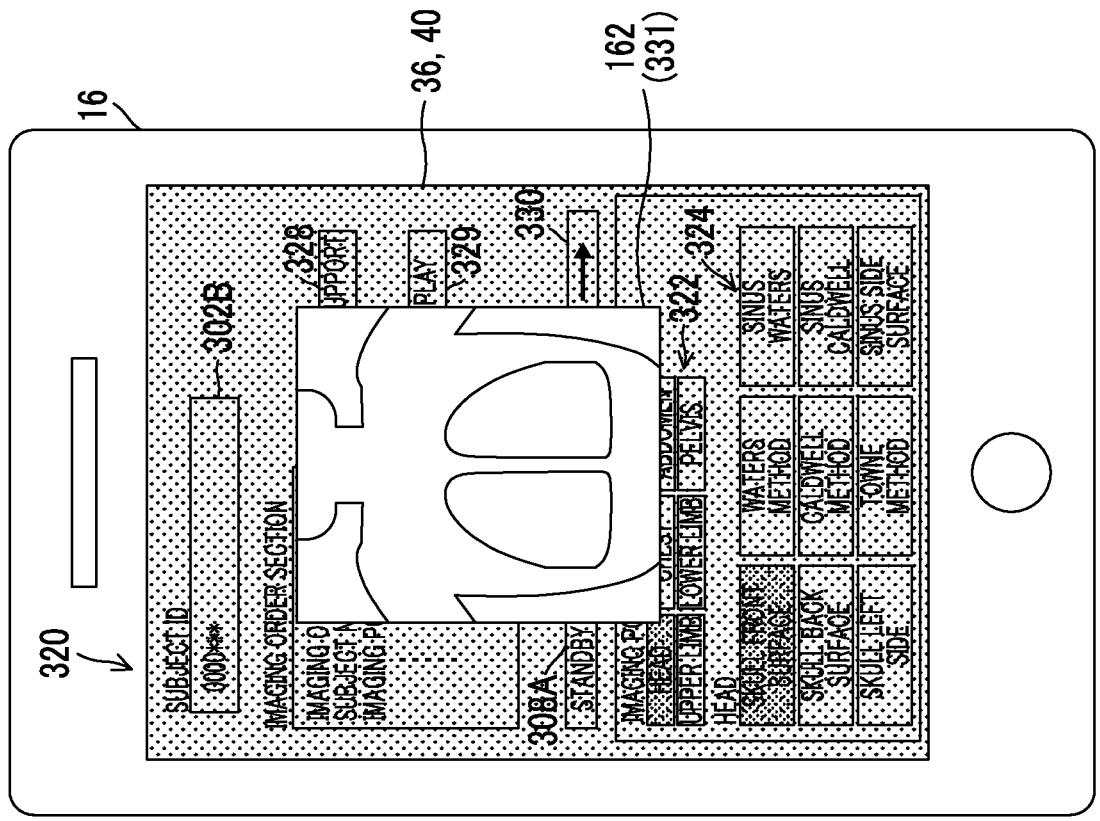
FIG. 60 is a schematic diagram illustrating a specific example of a state where a reference view is displayed on the menu select screen in an overlapping manner.

In step S732, the terminal control unit 30 displays a reference view 162 on the menu select screen 320 of the display 36 in an overlapping manner as shown in FIG. 60, and then, the procedure proceeds to step S736A. In this embodiment, for example, the entire menu select screen 320 is darkened so that the reference view 162 can be displayed in an easily visible state. The terminal control unit 30 displays the reference view 162 for a predetermined time, or until the user performs a predetermined operation such as a tap operation with respect to the display 36.

On the other hand, in a case where the positioning support button 328 is not designated, the procedure proceeds to step S734 from step S728. In step S734, the terminal control unit 30 determines whether to display a preview image. In a case where it is detected that the instruction button 329 is operated, the terminal control unit 30 determines that the preview image is to be displayed. In a case where the preview image is to be displayed, the determination is affirmative, and then, the procedure proceeds to step S735.

In step S735, the terminal control unit 30 causes the display 36 to display a preview image 331 received from the radiographic imaging apparatus 14 for a predetermined time, as shown in FIG. 60, and then, the procedure proceeds to step S736A. The user confirms the positioning of the subject W with reference to the preview image 331. The image quality of the preview image 331 to be displayed for confirming the positioning may be lower than the image quality of a preview image 172 to be displayed on an imaging confirmation screen 340 (see FIG. 61, details of which will be described later).

The preview image 331 is a radiographic image captured by the radiographic imaging apparatus 14 using irradiation of radiation R from the radiation irradiator 12 to the subject W. Thus, when displaying the preview image 331, the user instructs the irradiation of the radiation R using the irradiation switch 19. It is preferable that the state of the radiographic imaging apparatus 14 enters a ready state before the irradiation of the radiation R is instructed. Accordingly, in a case where it is detected that the operation of the preview display button 329 is detected, and in a case where the status of the radiographic imaging apparatus 14 is not in the ready state, it is preferable that the terminal control unit 30 causes the display 36 to display information indicating the non-ready state or transmits a signal for instructing the radiographic imaging apparatus 14 to transition to the ready state.

In step S736A, the terminal control unit 30 determines whether to display the next screen (an imaging confirmation screen 340, see FIG. 61, details of which will be described later) according to whether it is detected that the instruction button 330 is operated. In a case where the next screen is not to be displayed, the procedure proceeds to the above-described step S738A. On the other hand, in a case where the next screen is to be displayed, the procedure proceeds to step S742. Then, the terminal control unit 30 sets an imaging order based on the process as an imaging order used for imaging, and then, terminates the imaging preparation display process. Thereafter, the procedure proceeds to step S521 of the terminal single mode process.

In step S521, the terminal control unit 30 causes the display 36 to display the imaging confirmation screen 340 shown in FIG. 61, instead of the menu select screen 320.

As shown in FIG. 61, a display region 342 for displaying a preview image (preview image 172, see FIG. 61) is provided on the imaging confirmation screen 340 of this embodiment. Since a radiographic image is not yet captured and the preview image 172 is not generated when the imaging confirmation screen 340 is originally displayed on the display 36, the preview image 172 is not yet displayed in the display region 342.

Information 344, an instruction button 348, a complete button 349, and a re-imaging button 350 on the imaging confirmation screen 340 shown in FIG. 61 respectively correspond to the information 244, the instruction button 248, the complete button 249, and the re-imaging button 250 on the imaging confirmation screen 240 (see FIG. 49). Since imaging of a radiographic image is not yet performed when the imaging confirmation screen 340 is originally displayed on the display 36, although the complete button 349 and the re-imaging button 350 are displayed on the imaging confirmation screen 340, an instruction from the user is not possible.

In the next step S525, the terminal control unit 30 determines whether to return a screen to be displayed on the display 36 to the previous screen, that is, the menu select screen 320, according to whether the instruction button 348 is used for instruction. In a case where the previous screen is to be displayed, the procedure returns to step S720A (see FIG. 56) of the above-described imaging preparation display process. On the other hand, in a case where the previous screen is not to be displayed, in step S526, the terminal control unit 30 determines whether the preview image is received. In a case where the image data is not received, the procedure returns to step S525, and in a case where the image data is received, the procedure proceeds to step S531.

Further, as shown in FIG. 54, the console single mode process of this embodiment is different from the console single mode process (see FIG. 25B) of the first embodiment in that the process of step S531 is executed instead of step S530.

In step S531, the terminal control unit 30 updates the imaging confirmation screen 340 displayed on the display 36. In this embodiment, as a specific example, as shown in FIG. 62, the preview image 172 received in step S526 is displayed in the display region 342. Further, information 352 of a subject acquired from order information, information 353 of an imaging menu, information 354 indicating imaging date and time, an image ID given to a radiographic image by the radiographic imaging apparatus 14, or the like, is displayed at a location that does not disturb confirmation of the user, such as four corners of the preview image 172 for reading. In addition, an instruction of the instruction button 348 becomes impossible, and instructions of the complete button 349 and the re-imaging button 350 becomes possible.

Next, a terminal combination mode process in step S408 (see FIG. 23) of the terminal process, executed in the portable information terminal 16 of this embodiment will be described.

Figure 56:
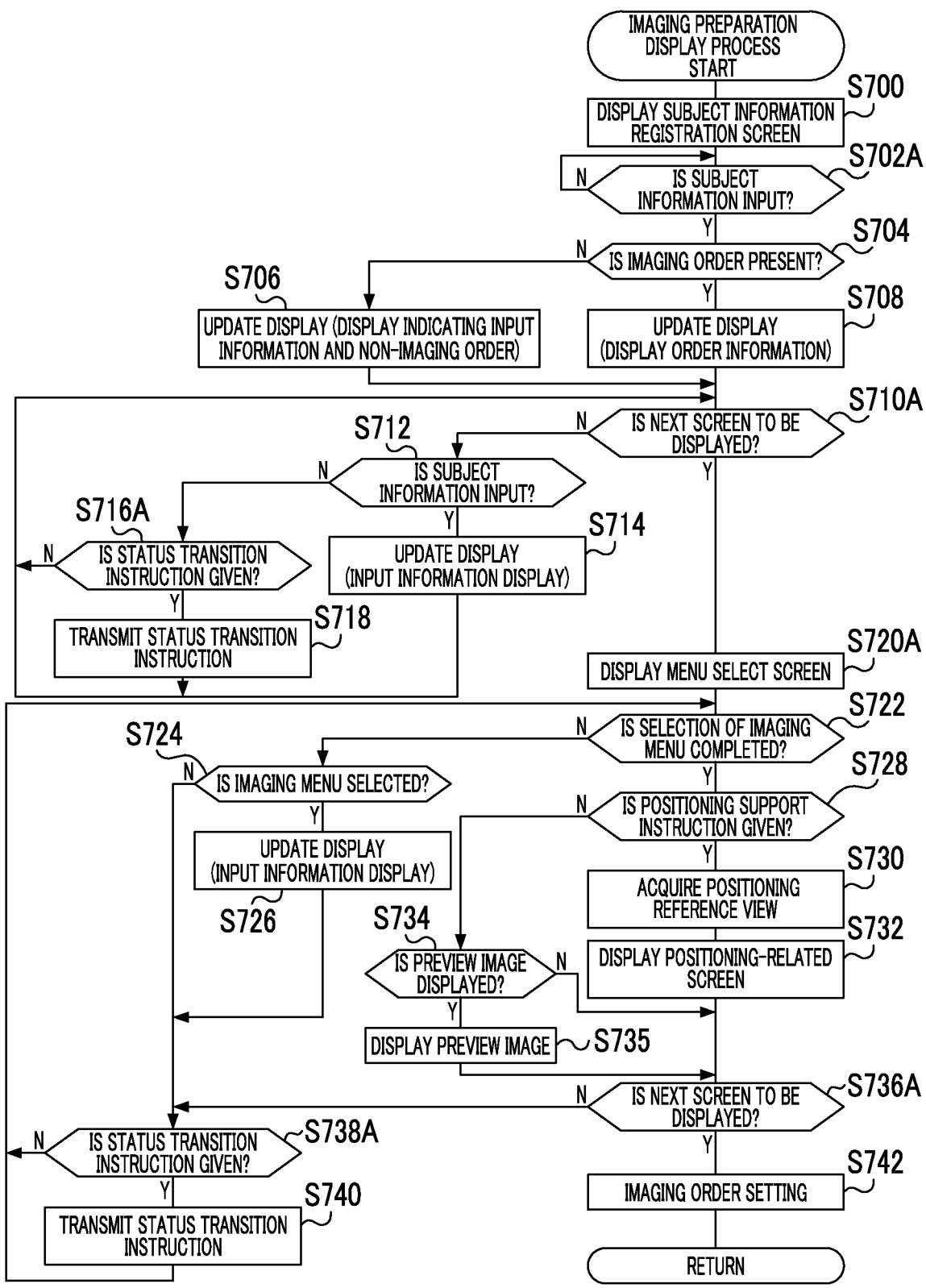
FIG. 56 is a flowchart illustrating an example of a flow of an imaging preparation display process executed by the terminal control unit of the portable information terminal of the second embodiment.

As shown in FIG. 54, the terminal combination mode process of this embodiment executes step S505B instead of step S505A of the terminal single mode process, and executes the terminal combination mode process shown in FIG. 56. As shown in FIG. 56, an imaging preparation display process of the terminal combination mode process is partly different from the console single mode process (see FIG. 44).

In the terminal combination mode process of this embodiment, steps S702B, S704B, S710B, S716B, S720B, S736B, and S738B are executed instead of steps S702A, S704A, S710A, S716A, S720A, S736A, and S738A of the terminal single mode process. In these processes, similar to the terminal combination mode process of the portable information terminal 16 of the first embodiment, in a case where a user receives a designated content signal indicating content designated on a screen displayed on the display 56 of the console 18, the terminal control unit 30 performs the same process as in a case where the user performs designation through the operation unit 40 of the host device.

Further, in the terminal combination mode process of this embodiment, step S708B is executed instead of step S708A of the terminal single mode process. Specifically, the display content to be updated in step S708B is different from that of the terminal single mode process. In the terminal combination mode process, as shown in FIG. 63, the portable information terminal 16 displays information 311 for prompting confirmation of detailed information relating to subject information, instead of the detailed information 307 relating to the subject, in the display region 303 on the subject information registration screen 300. A user confirms subject information through the subject information registration screen 200 (see FIG. 47) displayed on the display 56 of the console 18.

Further, in the terminal combination mode process of this embodiment, step S720B is executed instead of step S720A of the terminal single mode process. Specifically, display content of the menu select screen 320 to be displayed in step S720B is different from that of the terminal single mode process. As shown in FIG. 64, information 333 for prompting selection of an imaging menu is displayed in the display region 321 on the menu select screen 320, instead of the select buttons 322 and 324. A user performs selection of an imaging menu using the select buttons 222 and 224 of the menu select screen 220B (see FIG. 52) displayed on the display 56 of the console 18.

In this way, in the terminal combination mode process of this embodiment, in a case where the amount of display content, specifically, the number of pieces of information is large, the portable information terminal 16 displays information for prompting a user to perform confirmation through the console 18, without displaying display content thereof (information) on the display 36.

As described above, the radiographic imaging system according to each embodiment includes the portable information terminal 16 and the console 18 which are plural control devices of which each one performs a control relating to imaging of a radiographic image and of which at least one is selectively used; and the terminal control unit 30 of the portable information terminal 16 and the control unit 50 of the console 18 that respectively function as a setting unit that sets, with respect to usage control devices which are control devices to be selectively used, control content based on one usage control device in a case where one usage control device is used, and sets control content based on a combination of plural usage control devices in a case where plural usage control devices are used.

Further, the radiographic imaging system 10 according to each embodiment includes plural control devices of which each one performs a control relating to imaging of a radiographic image and of which at least one is selectively used, and the plural control devices include the portable information terminal 16 provided with the display 36 and the console 18 provided with the display 56; and the terminal control unit 30 and the control unit 50 that set, with respect to usage control devices which are control devices to be selectively used, display content to be displayed on the display 36 and the display 56 of the usage control devices on the basis of whether a usage control device is a portable one or a non-portable one, and whether the number of usage control devices is one or plural.

In addition, the radiographic imaging system 10 according to each embodiment includes the console 18 that is provided with the display 56 that displays information relating to imaging of a radiographic image, in which first display content is displayed on the display 56 in a case where a control relating to imaging of a radiographic image is independently performed and second display content having a smaller amount of information than that of the first display content is displayed on the display 56 in a case where a control relating to imaging of a radiographic image is performed in combination with a different control device; and the portable information terminal 16 that is provided with the display 36 having a display capability lower than that of the display 56, for displaying information relating to imaging of a radiographic image, in which third display content having a smaller amount of information than that of the first display content is displayed on the display 36 in a case where a control relating to imaging of a radiographic image is independently performed and fourth display content having a smaller amount of information than those of both the second display content and the third display content is displayed on the display 36 in a case where a control relating to imaging of a radiographic image is performed in combination with a different control device.

In this embodiment, the "amount of information" represents the amount of data and/or the amount of types of data. The amount of data represents the size of information (data). For example, in image data, image data for reading has a large amount of information (amount of data), and image data of a preview image has a small amount of information. Further, the amount of types of data represents which types of data are included in information concerned. For example, in data of information regarding a subject W, data only about a name and an age relates to a small amount of types of data, and thus, has a small amount of information (the amount of types of data), whereas data including a name, an age, a gender, a height, and a weight relates to a large amount of types of data, and thus, has a large amount of information. In a case where the "amount of information" is the amount of data and the amount of types of data, the "small amount of information" represents that at least one of the amount of data or the amount of types of data is small.

Thus, in the portable information terminal 16, since display content in a case where an operation is performed in the combination mode can be reduced compared with in a case where an operation is performed in the single mode, the display content is easily viewed in the combination mode, compared with the single mode.

Accordingly, it is possible to enhance the usability of the radiographic imaging system 10 for a user.

Further, in the radiographic imaging system 10 according to each embodiment, the amount of information of display content to be displayed on the portable information terminal 16 which is frequently used in a location other than a specific location such as an imaging room is set to be smaller than the amount of display content to be displayed in the console 18. For example, in the second embodiment, on the portable information terminal 16, detailed information 307 relating to a subject W is not displayed as it is, or information having a smaller amount of information than that of the detailed information relating to the subject W to be displayed in the display region 204 of the console 18 is displayed. Thus, it is possible to prevent information leakage of individual information or the like.

In each of the embodiments, as a specific example, a case where one portable information terminal 16 is provided as a portable control device provided in the radiographic imaging system 10 has been described, but a plurality of portable control devices may be provided as described above. For example, the radiographic imaging system 10 may include a tablet-type portable information terminal 16A and a smartphone-type portable information terminal 16B, as shown in FIG. 65. A display 36A of the portable information terminal 16A has a high display capability and at least a large display region, compared with a display 36B of the portable information terminal 16B. In this case, the amount of information of display content to be displayed on the portable information terminal 16A may be set to be larger than the amount of information of display content to be displayed on the portable information terminal 16B. For example, the display of the reference view 162 for positioning may be performed on the portable information terminal 16A, but may not be performed on the portable information terminal 16B. In this way, according to the display capability of the display 36 (36A, 36B) provided in the portable information terminal 16 (16A, 16B), the amount of information of display content may be set to become smaller as the display capability becomes lower.

In each of the above-described embodiments, a case where the portable information terminal 16 and the console 18 include the function of the setting unit of the invention has been described, but the invention is not limited thereto, and only any one of the portable information terminal 16 and the console 18 may have the function of the setting unit. In this case, an instruction for setting a control mode may be performed from a control device that includes the setting unit to a control device that does not include the setting unit.

Figure 66:
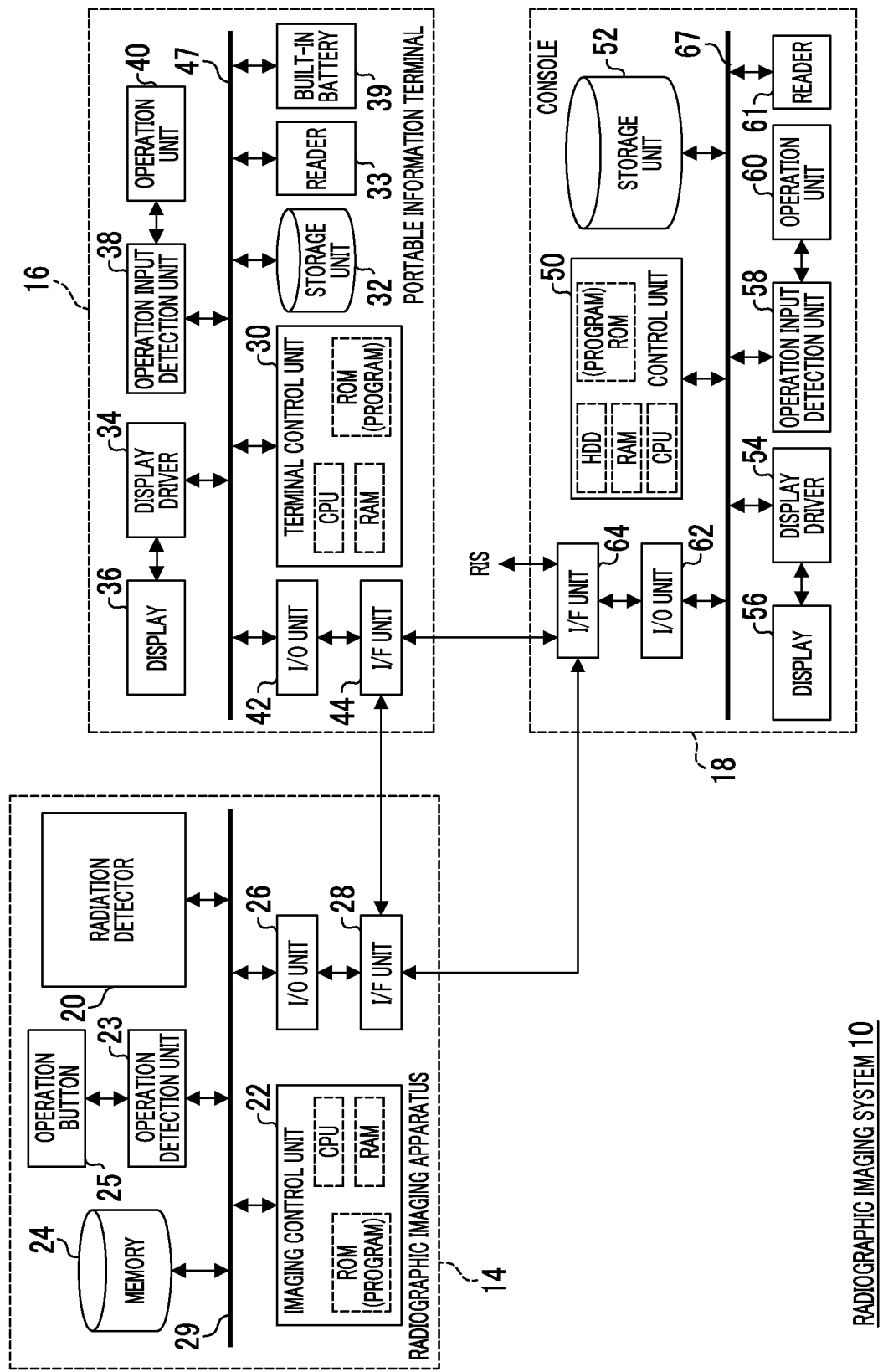
FIG. 66 is a block diagram illustrating another example of a schematic configuration of a radiographic imaging apparatus, a portable information terminal, and a console.

Further, it is sufficient if the function of the setting unit is provided in the radiographic imaging system 10. For example, the function of the setting unit may be provided in the radiographic imaging apparatus 14. FIG. 66 is a block diagram illustrating another example of a schematic configuration of a radiographic imaging apparatus, a portable information terminal, and a console of the radiographic imaging system 10 in this case. The radiographic imaging apparatus 14 includes the operation detection unit 23 and the operation button 25, and may transmit, in a case where an instruction of a control mode is received from a user, the instructed control mode to a corresponding control device. Further, in this case, for example, in a case where the above-described memory mode is set as an imaging mode, the radiographic imaging apparatus 14 may transmit an instruction for setting the imaging mode to the single mode in which the portable information terminal 16 is used to the portable information terminal 16.

Figure 67:
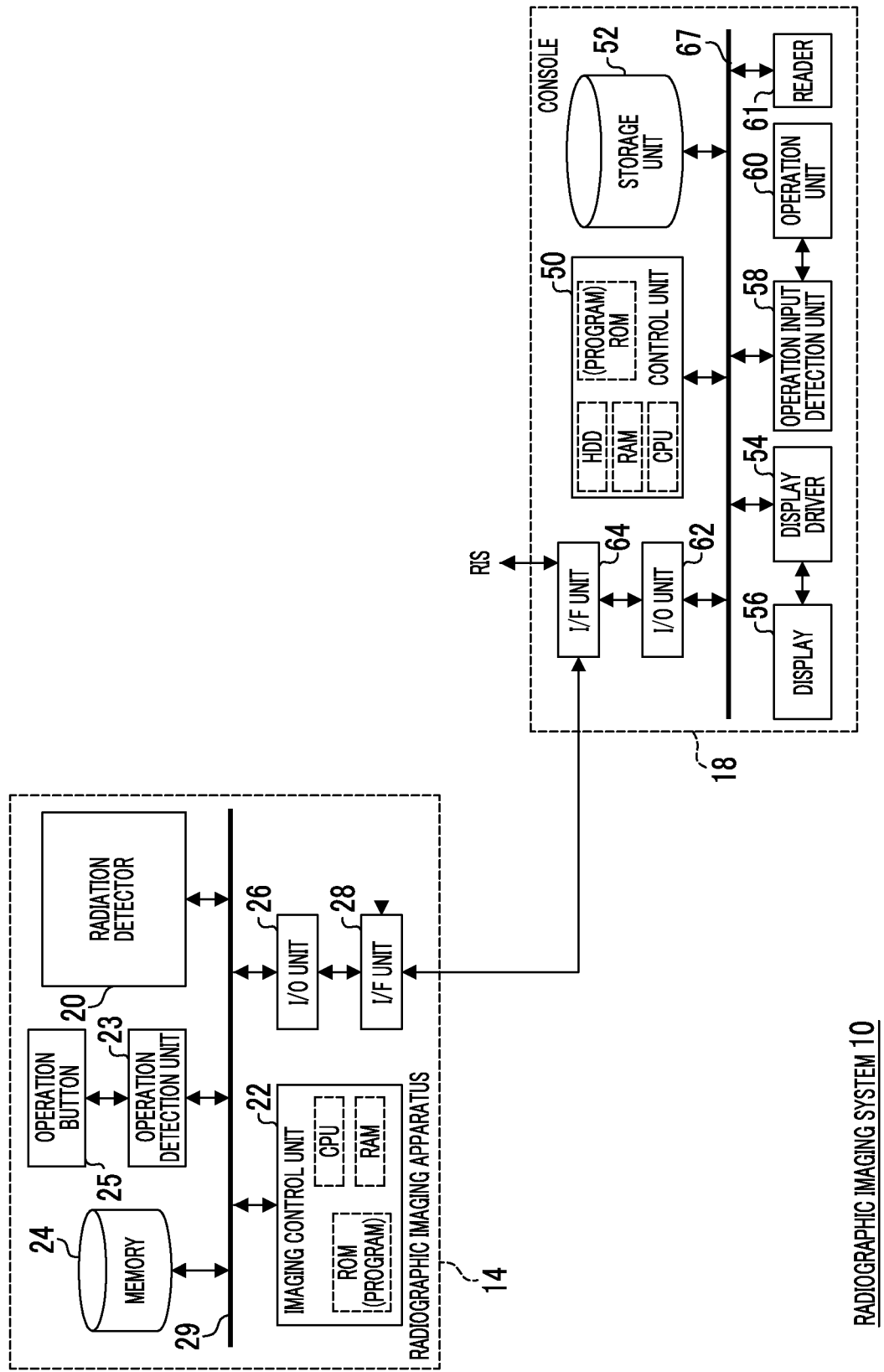
FIG. 67 is a block diagram illustrating still another example of a schematic configuration of a radiographic imaging apparatus, a portable information terminal, and a console.

In addition, even in a case where one control device has a plurality of control functions and executes different control contents, the invention may be applied. FIG. 67 is a block diagram illustrating still another example of a schematic configuration of a radiographic imaging apparatus of the radiographic imaging system 10 that includes only a console 18, and the console, as a specific example in this case. In a case where the console 18 shown in FIG. 67 has the same control function as that of the above-described portable information terminal 16 and the same control function as that of the above-described console 18, as described above, the single mode and the combination mode may be applied to the respective control functions.

Further, the control content is not limited to a control relating to a display method for display content to be displayed on the display 36 of the portable information terminal 16 and the display 56 of the console 18 as described above, and may be a control relating to imaging of another radiographic image.

In addition, in the combination mode, display content to be displayed on the display 56 of the console 18 is not limited to the above description. For example, display content that overlaps display content to be displayed on the display 36 of the portable information terminal 16 may not be displayed on the display 56 of the console 18. In this case, the above-described various screens may not be displayed on the display 56 of the console 18 as they are. Generally, a user does not perform a control relating to imaging based on display content that is not currently displayed on a display (display unit) of a control device. Thus, by setting overlapped display content so as not to be displayed, it is possible to prevent discrepancies from occurring when controls from a plurality of control devices are performed with respect to the radiographic imaging apparatus 14.

Further, for example, even in the same types of screens, in a case where a different piece of display content (display item) is included, only the different piece of display content may be displayed on the display 56 of the console 18. Specifically, for example, when comparing the positioning related screen 100 (see FIG. 18) displayed on the display 56 of the console 18 with the positioning related screen 160 (see FIG. 34) displayed on the display 36 of the portable information terminal 16, the positioning related screen 100 has a different point in that the information 103 indicating an imaging portion is displayed on the positioning related screen 100. Thus, only the information 103 indicating the imaging portion may be displayed on the display 56 of the console 18. In a case where display content is overlapped between the display 56 of the console 18 and the display 36 of the portable information terminal 16, the overlapped display content displayed on the display 56 of the console 18 may be displayed so as not to be noticeable compared with other display content. For example, the brightness may be set to be darker, or for example, the size of characters or an image may be set to be smaller.

Further, in the combination mode, display content to be displayed on the display 36 of the portable information terminal 16 is not limited to the above description. For example, as described above, in a case where the portable information terminal 16 is used in an imaging room where a subject W is present, only display content (screens and display items) based on a control or the like relating to imaging performed in the imaging room may be displayed on the display 36 of the portable information terminal 16.

For example, there is a case a user performs positioning of a subject W using the portable information terminal 16 in an imaging room, and then, instructs the start of irradiation of radiation R from the radiographic imaging apparatus 14 using the console 18 in a console room outside the imaging room. A door that divides the imaging room and the console room uses a saturnine door for prevention of leakage of the radiation R, and generally, the irradiation of the radiation R is performed in a state where the door is closed. Thus, in a case where the radiographic imaging apparatus 14 and the portable information terminal 16 use short-range wireless communication as described above, communication may be interrupted.

Accordingly, it is preferable that display content based on a control or the like relating to imaging performed in the console room is displayed on the display 56 of the console 18, and the display content may not be displayed on the display 36 of the portable information terminal 16. Further, in a case where display content is displayed on both display 56 of the console 18 and the display 36 of the portable information terminal 16, controls are performed with respect to the radiographic imaging apparatus 14 from the plurality of control devices, and thus, there is a concern that discrepancies occur. On the other hand, in a case where display content is displayed on only one control device, generally, since a control is performed with respect to the radiographic imaging apparatus 14 from a control device in which the display content is displayed, it is possible to prevent the occurrence of discrepancies.

Further, in the combination mode, settings with respect to display content (screens and display items) to be displayed on the display 36 of the portable information terminal 16 and the display 56 of the console 18 may be received from the user, and the display content may be customized according to the received settings. In this case, the types of screens to be displayed may be set by the user, and display content (display items) on one screen may be set by the user. For example, in a case where a setting of an imaging apparatus is not performed in the portable information terminal 16, a setting may be performed so that the display of the select button 135A for selecting the "imaging apparatus setting" in the initial imaging screen 134 (see FIG. 26) displayed on the display 36 of the portable information terminal 16 is not to be displayed. In this way, in a case where a part of display items displayed on one screen is set to non-display, it is preferable that a layout of the remaining display items to be displayed is arranged again. The remaining display items may be displayed to be large, compared with a case where all display items are displayed.

Further, in the single mode and the combination mode, content corresponding to a part or all of the above-described display content (screens and display items) to be displayed on the display 36 of the portable information terminal 16 may be presented to a user using a method other than display. For example, a speaker for outputting sound or the like may be provided in the portable information terminal 16, and sound may be presented by a voice guide.

In addition, display content (display items) on the above-described one screen may be divided to be respectively displayed on the portable information terminal 16 and the console 18.

Furthermore, the subject W may not be a human, and may be creatures such as animals or plants other than humans, or other objects.

Further, the radiation R used for imaging of a radiographic image is not particularly limited, and X-rays, y rays, or the like, may be applied.

The configurations and the operations of the radiographic imaging apparatus 14, the portable information terminal 16, the console 18, and the like described in each embodiment are examples, and may be modified according to situations within a range without departing from the concept of the invention.

EXPLANATION OF REFERENCES

10 radiographic imaging system
14 radiographic imaging apparatus
16, 16A, 16B portable information terminal
18 console
30 terminal control unit
36, 36A, 36B display
50 control unit
56 display

What is claimed is:

1. A radiographic imaging system comprising:
a plurality of control devices of which each one includes a display unit and performs a control relating to imaging of a radiographic image and of which at least one is selectively used;
a radiographic imaging apparatus that captures the radiographic image in one imaging mode selected from a plurality of imaging modes which are determined in advance in relation to imaging of the radiographic image and include a memory mode in which image data of a plurality of radiographic images obtained through imaging is stored in a storage unit which is integrally formed with the radiographic imaging apparatus; and
a setting unit that sets a usage control device, which is a control device to be selectively used, as one portable control device and sets a control content for displaying a second display content having a relatively larger amount of information than that of a first display content to the portable control device, in a case where the imaging mode of the radiographic imaging apparatus is the memory mode,
wherein the first display content is a content to be displayed on the display unit provided in the portable control device in a case where the usage control device includes a plurality of control devices including the portable control device.

2. The radiographic imaging system according to claim 1,
wherein the plurality of control devices include display units having different display capabilities respectively, and
wherein in a case where the number of usage control devices is plural, the setting unit sets a control content so that a display content displayed on the display unit of a usage control device provided with the display unit having a relatively low display capability among the plurality of usage control devices is smaller than a display content displayed on the display unit in a case where the number of usage control device is one.

3. The radiographic imaging system according to claim 2, further comprising:
a control unit that controls, in a case where the number of usage control devices is plural, so that a display content which is predetermined to be displayed on the display unit of a usage control device and which overlaps a display content displayed on the display unit of a different usage control device is not to be noticeable compared with other of the display content.

4. The radiographic imaging system according to claim 3, wherein in a case where the number of usage control devices is plural, the setting unit sets to a usage control device used in an imaging room in which imaging of a radiographic image is performed among the plurality of usage control devices, a display content that is determined in advance to be displayed in the imaging room.

5. The radiographic imaging system according to claim 3, further comprising:
a display content reception unit that receives, in a case where the number of usage control devices is plural, an instruction for a display content to be displayed on a display unit of at least one usage control device among the plurality of usage control devices,
wherein the setting unit sets to the at least one usage control device the display content received by the display content reception unit.

6. The radiographic imaging system according to claim 2, wherein in a case where the number of usage control devices is plural, the setting unit sets to a usage control device used in an imaging room in which imaging of a radiographic image is performed among the plurality of usage control devices, a display content that is determined in advance to be displayed in the imaging room.

7. The radiographic imaging system according to claim 2, further comprising:
a display content reception unit that receives, in a case where the number of usage control devices is plural, an instruction for a display content to be displayed on a display unit of at least one usage control device among the plurality of usage control devices,
wherein the setting unit sets to the at least one usage control device the display content received by the display content reception unit.

8. The radiographic imaging system according to claim 1, further comprising:
a control unit that controls, in a case where the number of usage control devices is plural, so that a display content which is predetermined to be displayed on the display unit of a usage control device and which overlaps a display content displayed on the display unit of a different usage control device is not to be noticeable compared with other of the display content.

9. The radiographic imaging system according to claim 8, wherein in a case where the number of usage control devices is plural, the setting unit sets to a usage control device used in an imaging room in which imaging of a radiographic image is performed among the plurality of usage control devices, a display content that is determined in advance to be displayed in the imaging room.

10. The radiographic imaging system according to claim 8, further comprising:
a display content reception unit that receives, in a case where the number of usage control devices is plural, an instruction for a display content to be displayed on a display unit of at least one usage control device among the plurality of usage control devices,
wherein the setting unit sets to the at least one usage control device the display content received by the display content reception unit.

11. The radiographic imaging system according to claim 1,
wherein in a case where the number of usage control devices is plural, the setting unit sets to a usage control device used in an imaging room in which imaging of a radiographic image is performed among the plurality of usage control devices, a display content that is determined in advance to be displayed in the imaging room.

12. The radiographic imaging system according to claim 11,
wherein in a case where the number of usage control devices is plural, the setting unit sets to a usage control device used in an imaging room in which imaging of a radiographic image is performed among the plurality of usage control devices, a display content that is determined in advance to be displayed in the imaging room.

13. The radiographic imaging system according to claim 11, further comprising:
a display content reception unit that receives, in a case where the number of usage control devices is plural, an instruction for a display content to be displayed on a display unit of at least one usage control device among the plurality of usage control devices,
wherein the setting unit sets to the at least one usage control device the display content received by the display content reception unit.

14. The radiographic imaging system according to claim 1, further comprising:
a display content reception unit that receives, in a case where the number of usage control devices is plural, an instruction for a display content to be displayed on a display unit of at least one usage control device among the plurality of usage control devices,
wherein the setting unit sets to the at least one usage control device the display content received by the display content reception unit.

15. The radiographic imaging system according to claim 1,
wherein in a case where the usage control devices are a plurality of control devices between which communication is possible, the setting unit sets to each of the usage control devices a control content based on a combination of the usage control devices.

16. The radiographic imaging system according to claim 1, further comprising:
a control content reception unit that receives the control content,
wherein the setting unit sets to the usage control device the control content received by the control content reception unit.

17. The radiographic imaging system according to claim 1,
wherein in a case where the number of usage control devices is plural, the setting unit is provided in at least one usage control device among the plurality of usage control devices.

18. The radiographic imaging system according to claim 1,
wherein the portable control device includes a battery for supplying power used for driving of the host device.

19. A control method for a radiographic imaging system including a radiographic imaging apparatus that captures a radiographic image in one imaging mode selected from a plurality of imaging modes which are determined in advance in relation to imaging of the radiographic image and include a memory mode in which image data of a plurality of radiographic images obtained through imaging is stored in a storage unit which is integrally formed with the radiographic imaging apparatus, and a plurality of control devices of which each one includes a display unit and performs a control relating to imaging of the radiographic image and of which at least one is selectively used, the method causing a computer to execute processes comprising:

setting a usage control device, which is a control device to be selectively used, as one portable control device, and a control content for displaying a second display content having a relatively larger amount of information than that of a first display content to the portable control device, in a case where the imaging mode of the radiographic imaging apparatus is the memory mode, wherein the first display content is a content to be displayed on the display unit provided in the portable control device in a case where the usage control device includes a plurality of control devices including the portable control device.

20. A non-transitory computer readable medium storing a control program for a radiographic imaging system including a radiographic imaging apparatus that captures a radiographic image in one imaging mode selected from a plurality of imaging modes which are determined in advance in relation to imaging of the radiographic image and include a memory mode in which image data of a plurality of radiographic images obtained through imaging is stored in a storage unit which is integrally formed with the radiographic imaging apparatus, and a plurality of control devices of which each one includes a display unit and performs a control relating to imaging of the radiographic image and of which at least one is selectively used, the program causing a computer to execute processes comprising:

setting a usage control device, which is a control device to be selectively used, as one portable control device, and a control content for displaying a second display content having a relatively larger amount of information than that of a first display content to the portable control device, in a case where the imaging mode of the radiographic imaging apparatus is the memory mode, wherein the first display content is a content to be displayed on the display unit provided in the portable control device in a case where the usage control device includes a plurality of control devices including the portable control device.

* * * * *